US010280211B2

(12) United States Patent
Braz Goncalves et al.

(10) Patent No.: US 10,280,211 B2
(45) Date of Patent: May 7, 2019

(54) ENGINEERED RABBIT ANTIBODY VARIABLE DOMAINS AND USES THEREOF

(75) Inventors: João Manuel Braz Goncalves, Montijo (PT); Frederico Nuno Castanheira Aires Da Silva, Lisbon (PT)

(73) Assignee: TECHNOPHAGE, INVESTIGAÇÃO E DESENVOLVIMENTO EM BIOTECNOLOGIA, SA, Lisbon (PT)

( * ) Notice: Subject to any disclaimer, the term of this patent is extended or adjusted under 35 U.S.C. 154(b) by 0 days.

(21) Appl. No.: 12/598,170

(22) PCT Filed: Apr. 30, 2008

(86) PCT No.: PCT/PT2008/000018
§ 371 (c)(1),
(2), (4) Date: Oct. 29, 2009

(87) PCT Pub. No.: WO2008/136694
PCT Pub. Date: Nov. 13, 2008

(65) Prior Publication Data
US 2010/0136627 A1 Jun. 3, 2010

Related U.S. Application Data

(60) Provisional application No. 60/916,226, filed on May 4, 2007.

(51) Int. Cl.
*C07K 16/00* (2006.01)
(52) U.S. Cl.
CPC ........ *C07K 16/00* (2013.01); *C07K 2317/567* (2013.01)
(58) Field of Classification Search
CPC .................... C07K 16/00; C07K 2317/567
USPC ................ 435/69.6; 530/387.1, 387.3, 391.7
See application file for complete search history.

(56) References Cited

U.S. PATENT DOCUMENTS

| 5,093,241 A | 3/1992 | Bennett et al. |
| 2005/0048578 A1 | 3/2005 | Zhang |
| 2006/0216293 A1 | 9/2006 | Couto et al. |

FOREIGN PATENT DOCUMENTS

| WO | WO 2001/030393 | 5/2001 |
| WO | WO 2001/031065 | 5/2001 |
| WO | WO 2004/016740 | 2/2004 |
| WO | WO 2004/003019 | * 6/2004 |
| WO | WO 2004/091543 | 10/2004 |
| WO | WO 2005/016950 | 2/2005 |
| WO | WO 2006/073748 | 7/2006 |
| WO | WO 2008/004834 | 1/2008 |

OTHER PUBLICATIONS

Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Esteves e t al., Allelic Variation at the $V_H$a Locus in Natural Populations of Rabbit (*Oryctolagus cuniculus*, L.)[1], Journal of Immunology, Jan. 15, 2004, vol. 172, No. 2, pp. 1044-1053.
Marchesini et al., "N-Terminal-Capturing Screening System for the Isolation of *Brucella abortus* Genes Encoding Surface Exposed and Secreted Proteins," Microbial Pathogenesis, Aug. 2004, vol. 37, No. 2, pp. 95-105.
Pospisil et al., "B-Cell Superantigens May Play a Role in B-Cell Development and Selection in the Young Rabbit Appendix," Cellular Immunology, May 1, 1998, vol. 185, No. 2, pp. 93-100.
Rader et al., "The Rabbit Antibody Repertoire As a Novel Source for the Generation of Therapeutic Human Antibodies," Journal of Biological Chemistry, May 5, 2000, vol. 275, No. 18, pp. 13668-13676.
Robben et al., "An *Escherichia coli* Plasmid Vector System for High-Level Production and Purification of Heterologous Peptides Fused to Active Chloramphenicol Acetyltransferase," Gene, Jan. 1, 1993, vol. 126, No. 1, pp. 109-113.
Da Silva et al., "Camelized Rabbit-Derived VH Single-Domain Intrabodies Against Vif Strongly Neutralize HIV-1 Infectivity," Journal of Molecular Biology, Jul. 9, 2004, vol. 340, No. 3, pp. 525-542.
Mage "B cell and antibody repertoire development in rabbits: the requirement of gut-associated lymphoid tissues." Dev Comp Immunol. 2006;30(1-2):137-53.
Maxwell et al., "A Simple in vivo Assay for Increased Protein Solubility," Protein Science, 8, pp. 1908-1911, 1999.
Rader C. "Antibody libraries in drug and target discovery," Drug Discov Today. Jan. 1, 2001;6(1):36-43.
Steinberger et al., "Generation and Characterization of a Recombinant Human CCR5-Specific Antibody," The Journal of Biological Chemistry, vol. 275, No. 46, pp. 36073-36078, 2000.
Technophage, Investigação Desenvolvimento Em Biotecnologia, SA, Search Report issued in Singapore Patent Application No. 2013071972, 4 pages, dated Oct. 4, 2017.

* cited by examiner

*Primary Examiner* — Lynn A Bristol
(74) *Attorney, Agent, or Firm* — Margaret B. Brivanlou; Nicole Fortune; King & Spalding LLP

(57) ABSTRACT

The present invention relates to methods for screening and producing polypeptides that immunospecifically bind to an antigen, which: polypeptides comprise binding domains that are derived from rabbit immunoglobulin. Using rabbit antibody heavy-chain or light-chain scaffolds, the methods of the invention allow identification of novel CDR loops and framework regions that confer enhanced stability and/or affinity to isolated immunoglobulin variable domains, in particular, relative to those derived from rodent antibodies. The enhanced stability and/or affinity of the variable domains of the invention permit their use in the production research tools or therapeutic immunospecific polypeptides, including single domain immunospecific polypeptides, i.e., comprising one of a $V_H$ or $V_L$ domain.

18 Claims, 6 Drawing Sheets

Figure 1:
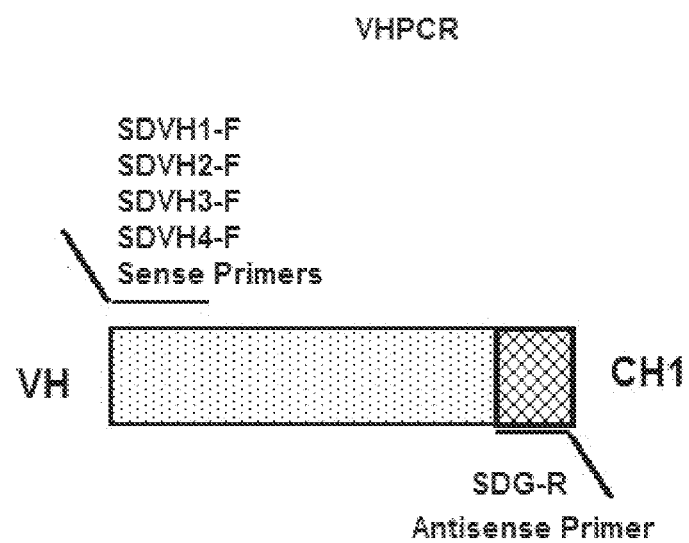

Specification includes a Sequence Listing.

|  | VH FR1 | VH CDR1 | VH FR2 | VH CDR2 | VH FR3 | VH CDR3 | VH FR4 |
|---|---|---|---|---|---|---|---|
|  | 1 | 31 | 45 | 58 59 | 70 | 110 111 | 126 136 |
| (SEQ ID NO:1) | QQQLV--ESGGR----LVKPDETLTITCTVS | GIDL-SSNAMN-- | WVRQAPGEGLEWIG | TIS--TGGSTY | YASWAKGRFTIS-KTS-TTVDLKITSP--FTEDTATYFCAR | ALYAGST-TGSPFNL | WGQGTLVTVSS |
| (SEQ ID NO:2) | --QSVE-ESRGR----LVTPGTFLTLRCTAS | GFSLNSGYMETI- | WVRQAPGKGLEYIG | IIX--TGDSAS | YASWAKGRFTIS-KTSSTTVDLKITSP--FTEDTATYFCAR | RG---YNSGWGAENL | WGQSTLVTVSS |
| (SEQ ID NO:3) | QEQLMETESGGGAEGGLVKPGGSLELCCKAS | GFSLSINYWI--C | WVRQAFGKGLEWIG | CVYT-DQGSTY | YATWVNGRFTLSRDIDQSTGCLQLNSL--TAADFATYFCAR | KE-----YVISTYNF | WGQGTLVTVSS |
| (SEQ ID NO:4) | QEQLVE--SGGGL----VKPEGSLTLPCKAS | GIDFS-NYGIS-- | WVRQAPGKGLEWVA | YIYP-DYGTTD | YANWVNGRFTISLDNAQNTVFLQMTSL--TAADFATYFCAR | DGGYDDYNDWGYENL | WGPSTLVTVSS |
| (SEQ ID NO:5) | --QSLE-ESGGG----LVQPEGSLTLRCTAS | GFTISNSYYMETC | WVRQAPGKGLEWIG | CKYAGSSGIGY | YASWAEGRFSIS-KASSTTVLQMETTSLRAADTATYFCAR | FV-----GYGGFWDL | WGPGTLVTVSS |

FIG. 3

```
            VL FR1                23       VL CDR1           38      VL FR2         52 53 VL CDR2 60         VL FR3                            91 92   VL CDR3           106     VL FR4      116B
            1                                                                                                                                                                                
(SEQ ID NO:6) ELVLTQTPPSLSASVGETVRIRC LASEDIYSG---IS WYQKPEKPPTLLIS GASNLEA GVPPRFSGSGSGTDYLTIGGVQAEDVATYYC LGSYSGSAD----- F--GAGTMVEIK-
(SEQ ID NO:7) ELVLTQSPSSKSVPVGDTVTINC QASESVAGG-NRLS WYQQKPGQPPRLLIY RASNLAS GVPSRFKGSGSGTQFLTISDLECDDAATYYC QGGYDCSSADCS-A P--GGGTQLTVTG
(SEQ ID NO:8) ELVLTQTPSPVSAAVGGTVTISC QSSESVYNNNQ LS WFQQKPGQPPKLLIY EASKLAS GVPSERFKGSGSGTQFTLTISDLECDDAATYYC QGAY---SHVH--A P--GGGTELEIL-
(SEQ ID NO:9) ELVLTQSPS--VSGAVGGTVIINC QTSESISN--W-LA WYQQKPGQPPKLLIY DASKLAS GVPSRFKGSGSGTQFTLTISGVQCDDAATYYC QGGYS-GATNN--A F--GGGTQLTVTG
```

FIG. 4

ENGINEERED RABBIT ANTIBODY VARIABLE DOMAINS AND USES THEREOF

1. FIELD OF THE INVENTION

The present invention relates to methods for screening and producing polypeptides that immunospecifically bind to an antigen, which polypeptides comprise binding domains that are derived from rabbit immunoglobulin. Using rabbit antibody heavy-chain or light-chain scaffolds, the methods of the invention allow identification of novel CDR loops and framework regions that confer enhanced stability and/or affinity to isolated immunoglobulin variable domains, in particular, relative to those derived from rodent antibodies. The enhanced stability and/or affinity of the variable domains of the invention permit their use in the production of research tools and therapeutic polypeptides that exhibit immunospecificity for an antigen of interest, including single binding-domain polypeptides, i.e., single domain antibodies comprising one of a $V_H$ or $V_L$ domain.

2. BACKGROUND

Antibodies are composed of two chains termed light and heavy chains. The light chain contains an amino-terminal variable domain (VL domain) and a carboxy-terminal constant domain (CL). The heavy chain is composed of an amino-terminal variable domain (VH) and three constant domains (CH1, CH2, CH3). The antibody binding site is located in the VL and VH domains and is made up by six hypervariable loops that represent the Complementarity-Determining Regions (CDRs). Both VL and VH regions contain three CDR loops (CDR1, CDR2 and CDR3), which are connected to a structurally conserved beta.-sheet framework.

With the development of hybridoma technology, it became possible to produce a single population of antibodies, or monoclonal antibodies (mAbs), that specifically targeted a single epitope opening a revolution in the drug discovery field. However, problems with antibody production and in vivo responses, including immunogenicity and cytokine-associated side-effects, have lead to the investigation of altering antibody structure and/or function while still retaining immunospecific binding. Studies have attempted to reduce the antibody to its smallest functional form, without significantly changing the antigen recognition and affinity. The identification of the smallest antibody fragment that is capable of binding to antigen has evolved from full antibody molecules or IgG to Fab and recombinant single chain Fv fragments.

Due to the progress in gene recombination in the 80's, the rapid and easy generation of recombinant variable domains was possible. Using the polymerase chain reaction, diverse repertoires of genes encoding VH and VL domains were cloned from the genomic DNA of immunized animals, allowing the characterization of multiple binding activities and functionalities against several antigens. Nevertheless, the variable domain fragments initially isolated were scarcely soluble and difficult to produce.

Problems in production were addressed with the characterization of camelid antibodies, which are dimeric molecules that comprise only heavy chains. Not only did the discovery of the dimeric molecule address many issues with respect to recombinant antibody production, but the molecule also highlighted the possibility that the heavy chain of immunoglobulin molecules could direct immunospecific binding in the absence of a light chain. It is now widely accepted that Ig heavy chains may retain significant antigen binding ability in the absence of a light chain. There is also evidence from structural studies that the CDR3 region of the $V_H$ domain is the most significant of the CDR domains with respect to immunospecificity. This is based on the findings that the HCDR3 amino acid residues provide most of the surface contact area and are crucial in the molecular interaction with the antigen. Accordingly, further reduction of antigen binding protein size to single domain binding proteins may be possible based upon immunoglobulin VH domains.

2.1 Rabbit Antibodies

The rabbit antibody repertoire, which in the form of polyclonal antibodies has been utilized for decades, is an outstanding source for antibodies that feature strong affinity and high specificity (Mage et al., 2006). In addition, rabbits, which belong to the order Lagomorpha, are evolutionarily distant from mice and rats, which belong to the order Rodentia. As a consequence, epitopes conserved between rodent and human antigens that are invisible to rodent mAbs (and also human mAbs generated from transgenic mice with human immunoglobulin genes) can often be recognized by rabbit polyclonal antibodies.

Rabbit mAbs generated by phage display offer additional advantages due to the fact that phenotype and genotype are selected at the same time. Knowledge of the rabbit mAb sequence allows the ready generation of a variety of mAb formats, including single-domain antibodies, scFv, Fab, and IgG, and, importantly, humanization and affinity maturation (Rader et al., 2000; Steinberger et al., 2000; Rader, 2001). Consequently, rabbit mAbs generated by phage display have become promising reagents for therapeutic applications in humans.

In normal rabbits, 70-90% of Ig molecules and B cells carry the VHa allotypes due to the use of the D-proximal VH gene segment, VH1, in VDJ gene rearrangements. Rearrangements of a variety of Vk and Vl gene segments appear to occur in rabbits, since a variety of different VL sequences have been found among expressed cDNA sequences.

The B cell repertoire that develops in rabbit bone marrow is limited by the small number of VH gene segments used in VDJ gene rearrangements. Whereas multiple Vk gene segments are rearranged in bone marrow B lineage cells, most B lineage cells rearrange the same VH gene, VH1, which encodes the VHa allotypic sequences. The repertoire is also limited by the usage of a small number of JH and D gene segments in VDJ rearrangements. JH4 is found in 80% of the VDJ gene rearrangements and JH2 in the other 20%; the other three functional JH gene segments are used rarely. Also, from the total of 12 D gene segments, most VDJ gene rearrangements use D2a (D9), D2b (Df), D3 or D5; D4 and D6 are rarely utilized. While limited usage of VH, D and JH gene segments would result in a limited VDJ repertoire, N nucleotides are found in essentially all VD and DJ junctions from the earliest rearrangements during cellular differentiation. The high diversity of N regions among VDJ gene rearrangements results in a much larger repertoire than expected from rearrangement of a limited number of V, D and J gene segments. The size of this repertoire has not been estimated. However, given that essentially all VDJ genes are somatically diversified in periphery after B cells leave the bone marrow and other primary sites of B lymphopoiesis, it is conceivable that the repertoire that develops in the primary sites of B cell development is functionally insufficient.

After B-cell Ig gene rearrangements occur in sites such as bone marrow of young rabbits, immature IgM B cells undergo further Ig repertoire diversification in appendix and other gut-associated lymphoid tissues. These sites appear to foster development of a primary preimmune repertoire.

Gene conversion of rearranged heavy and light chain sequences is found in rabbit appendix by 3-4 weeks of age. Somatic hypermutation occurs in the D and J regions, which lack known gene conversion donors. The JH region is also diversified by somatic hypermutation and it is therefore likely that somatic hypermutation also occurs in the rearranged VH gene segments.

Gene conversion and somatic hypermutation occur not only in germinal-centers of the young rabbit appendix, but are also used for diversification during immune responses in secondary lymphoid tissues such as spleen and lymph nodes.

When sequences of rearranged heavy and light chain genes in clones from developing appendix and from spleen during specific immune responses are compared, the diversification patterns in the clones from appendix are strikingly different from those found in spleen, where an immunizing antigen was driving the expansion and selection process toward high affinity. Clonally related appendix B cells developed different amino acid sequences in each complementarity-determining region (CDR), including CDR3, whereas dominant clones from spleen underwent few changes in CDR3.

The data also indicate a higher rate of hypermutation in rabbit during immune responses in splenic germinal centers, such that the balance between hypermutation and selection tends more towards mutation and less towards selection in rabbit compared to mouse. Germinal centers (GCs) in secondary lymphoid organs are specialized structures within which somatic diversification of rearranged V genes occurs that lead to affinity maturation of Abs in immune responses to T-dependent Ags.

Unlike mice and humans, rabbits rearrange only a few heavy chain V region (VH) genes, so that the diversity generated by combinatorial mechanisms is limited. The overall pattern is one of splenic precursor cells whose germline or near germline sequences changed both by gene conversion and point mutations during early divisions and largely by point mutations during later divisions. It is possible that within the same expanding clonal populations, considerable diversification of light chain sequences occurred in parallel with the changes in the VH sequences, these events may produce the diverse sequences that serve as substrates for further affinity maturation by selection either within GCs or later among emigrant cells in sites such as bone marrow.

The limited heavy chain VHDHJH repertoire due to preferential usage of the VH1 gene segment is compensated by a diverse light chain VkJk repertoire in B cells developed in the bone marrow. This repertoire is greatly expanded both in GALT by gene conversion and somatic hypermutation, and later, in germinal centers of spleen and lymph nodes following immunization.

As discussed above, rabbit antibodies are subject to evolving maturation by somatic hypermutation, and are not dependent on gene conversion for increasing its affinity and binding towards a given antigen. In addition to recognition, another important property of isolated single-domain antibodies is its inherent structure stability. Because rabbit antibodies evolve by somatic hypermutation, VH and VL stability of rabbit antibodies is not dependent on inherent properties of a single VH or VL family but a property that can be subject to evolution. Antibody stability is important not only for promoting a good conformation of CDRs for antigen recognition, but also for downstream applications such as production and serum half-life. Moreover, since the present invention isolates VH and VL protein domains, it is conceivable that the hydrophobic interface can promote protein aggregation. For that reason, then present method of selecting isolated VH and VL domains that are inherently stable provide the possibility of identifying novel small-domain antibodies with original and different properties than those presently existent.

The present method encompasses the identification of distinctive rabbit single-domain antibodies, with unique properties compared to human, mouse and camel antibodies, and presenting high affinity, specificity and stability.

3. SUMMARY OF THE INVENTION

The present invention relates to methods of production of immunospecific polypeptides comprising sequences derived from rabbit immunoglobulin variable domains, to polypeptides comprising such sequences, and to polypeptides produced by such methods. In particular, the invention encompasses methods for the isolation and use of rabbit $V_H$ and/or $V_L$ domains and/or novel CDR and framework regions derived therefrom. The invention further provides for the identification of novel amino acid sequences (including novel amino acid residues at defined positions) within isolated rabbit $V_H$ and $V_L$ domains for use as "scaffold" or structural sequences in the context of CDR loops and/or framework regions in recombinant immunospecific polypeptides. The rabbit scaffold sequences (including scaffold residues) or novel CDR/framework sequences of the invention enhance the stability and/or affinity of the variable domain(s) and/or immunospecific polypeptides (e.g., antibodies) that contain them, in particular, relative to rodent antibodies, enabling the production and/or use of highly specific, single domain immunopeptides, e.g., single domain antibodies.

The present invention encompasses the production of novel rabbit $V_H$ or $V_L$ domains with specificity for a given antigen, or epitope thereof. In particular, the invention provides for a method of producing rabbit $V_H$ or $V_L$ domains said method comprising: (a) selecting from a phage expression library a set of DNA sequences that encode rabbit $V_H$ or $V_L$ domains that immunospecifically bind to a desired antigen or epitope thereof (also known as phage "panning") and (b) expressing the set of sequences, or a subset thereof, in bacteria as a fusion protein with chloramphenicol acetyltransferase ("CAT") and selecting bacteria that have chloramphenicol resistance by virtue of CAT expression. In alternate embodiments, the present invention provides for a method of producing rabbit $V_H$ or $V_L$ domains, said method comprising (a) expressing sequences of DNA or cDNA encoding $V_H$ or $V_L$ domains of rabbit immunoglobulins in bacteria as a fusion protein with CAT, (b) selecting bacteria that have chloramphenicol resistance by virtue of CAT expression and obtaining the set of DNA sequences encoding the rabbit $V_H$ or $V_L$ domains from the selected bacteria, and (c) preparing a phage expression library from the set of DNA sequences obtained in step (b) and selecting DNA sequences that encode $V_H$ or $V_L$ domains that immunospecifically bind to a desired antigen or epitope thereof (i.e., panning the library for immunospecific binding to the antigen or epitope). In certain embodiments, the present invention encompasses methods for the production of a rabbit $V_H$ or $V_L$ domain wherein the phage panning step is repeated one or more times. In related embodiments, the phage panning step may or may not be repeated sequentially. The phage expression library for use in accordance with the present invention may be obtained commercially or prepared by any method described herein and/or known in the art. Expression of DNA or cDNA sequences in bacteria as fusion proteins is well known and may be performed by any method described herein or known in the art, e.g., cloning the DNA or cDNA sequence encoding the $V_H$ or $V_L$ domain into an expression vector that comprises a nucleotide sequence encoding CAT and a promoter sequence that drives fusion protein expression. Expression of CAT in bacteria as a fusion protein with insoluble peptides confers significantly lower chloramphenicol resistance than does expression as a fusion protein with a soluble peptide (e.g., a peptide that is at least partially folded and not aggregated when expressed in bacteria). Accordingly, selection for chloramphenicol resistance in bacteria transformed with nucleotide sequences encoding fusion proteins comprising $V_H$ or $V_L$ domains and CAT will select those sequences that are capable of being recombinantly expressed as properly folded and/or in non-aggregative forms. In certain embodiments, the present invention encompasses methods comprising culturing said transformed bacteria on selective media comprising at least 0.1 mM, at least 0.2 mM, at least 0.4 mM, at least 0.6 mM, at least 0.8 mM, at least 1.0 mM, at least 1.2 mM, at least 1.4 mM, at least 1.6 mM, at least 1.8 mM, at least 2.0 mM, at least 2.5 mM, at least 3.0 mM, at least 5.0 mM, at least 10 mM, at least 15 mM, or at least 20 mM chloramphenicol. Selection of sequences encoding $V_H$ or $V_L$ domains by the CAT-fusion assay described herein selects for protein stability. The invention further encompasses the use of any other method known in the art or described herein for assessing the $V_H$ or $V_L$ domains of the invention, including assays of thermal and/or kinetic stability (e.g., determinations of protein melting temperature ("Tm") or Gibbs free energy of folding ($\Delta G_{N-U}$)). In certain embodiments, the $V_H$ or $V_L$ domains of the invention have a melting temperature of at least about 40° C., at least about 45° C., at least about 50° C., at least about 54° C., or about 55° C. or greater.

The invention relates to polypeptides comprising $V_H$ or $V_L$ domains, or amino acid sequences or residues, derived from and/or identified in rabbit immunoglobulins, which polypeptides immunospecifically bind desired antigens, or epitopes thereof, as determined by any standard method known in the art for assessing antigen/binding-protein specificities. Assays to determine the binding specificity of an immunospecific polypeptide, e.g., an antibody or antigen binding fragment thereof, for an antigen or epitope include, but are not limited to ELISA, western blot, surface plasmon resonance (e.g., BIAcore) and radioimmunoassay. Any method known in the art for assessing binding polypeptide specificity may be used to identify polypeptides of the invention that exhibit a Kd of greater than 0.001 nM but not greater than 5 nM, not greater than 10 nM, not greater than 15 nM, not greater than 20 nM, not greater than 25 nM, not greater than 30 nM, not greater than 35 nM, not greater than 40 nM, not greater than 45 nM, or not greater than 50 nM. In certain embodiments, the isolated $V_H$ or $V_L$ domains of the invention exhibit a Kd of no greater than 5 nM, no greater than 10 nM, no greater than 15 nM, no greater than 20 nM, no greater than 25 nM, no greater than 30 nM, no greater than 35 nM, no greater than 40 nM, no greater than 45 nM, or no greater than 50 nM as determined by BIAcore assay.

The nucleotide sequences encoding immunoglobulin $V_H$ or $V_L$ domains may be obtained from naïve rabbits or rabbits that have been previously immunized with an antigen. Immunization of rabbits and isolation of nucleotide sequences (e.g., cDNA) encoding rabbit $V_H$ or $V_L$ domains may be done by any method known in the art or described herein. In certain embodiments, nucleotide sequences encoding $V_H$ or $V_L$ domains may be obtained from any tissue of the naïve or immunized rabbit, but is preferably obtained from a tissue source rich in plasma cells, e.g., B cells. In certain embodiments, the rabbit tissue comprising nucleotide sequences encoding $V_H$ or $V_L$ domains is bone marrow. In other embodiments, the rabbit tissue comprising nucleotide sequences encoding $V_H$ or $V_L$ domains is appendix tissue. In yet other embodiments, the rabbit tissue comprising nucleotide sequences encoding $V_H$ or $V_L$ domains is lymphoid tissue; in a specific example in accordance with this embodiment the lymphoid tissue is spleen or lymph node tissue.

The present invention further encompasses immunospecific polypeptides, e.g., antibodies, or antigen binding fragments thereof, comprising the $V_H$ or $V_L$ domains isolated, identified or constructed by the methods described herein. In alternate embodiments, the invention encompasses immunospecific polypeptides, e.g., antibodies, comprising novel (relative to the amino acid sequences of immunoglobulins of species other than rabbit) scaffold amino acid sequences, novel amino acid residues at certain positions in the $V_H$ or $V_L$ domain (e.g., as determined according the position in the rabbit $V_H$ and $V_L$ alignment sequence presented in FIG. 3A and FIG. 4, respectively), or novel sequences of CDR loops identified by the methods of the invention. In certain embodiments, the immunospecific polypeptides of the invention are monoclonal antibodies, multispecific antibodies, humanized antibodies, synthetic antibodies, chimeric antibodies, polyclonal antibodies, single-chain Fvs (scFv), single chain antibodies, anti-idiotypic (anti-Id) antibodies (including, e.g., anti-Id and anti-anti-Id antibodies to antibodies of the invention), diabodies, minibodies, nanobodies, or antigen binding fragments of any of the above, including, but not limited to, Fab fragments, F(ab') fragments, disulfide-linked bispecific Fvs (sdFv), and intrabodies. In certain embodiments the immunospecific polypeptides of the invention are bispecific or multispecific. Bi- or multi-specific molecules of the invention may be formed using methods well known in the art, e.g., chemical conjugation of one or more molecule of the invention to each other and/or to differing epitope binding polypeptides, wherein the binding domains of the bi- or multi-specific molecule exhibit affinity for at least two differein antigens. For example, the immunospecific polypeptide of the invention may comprise a first and a second $V_L$ domain, or a first and second $V_H$ domain, wherein said first and second domain have differing binding specificities (i.e., bind to differeing antigens). In other embodiments, the immunospecific polypeptides of the invention comprise one $V_L$, or one $V_H$ domain, and one antigen binding polypeptide, wherein the $V_L$ domain, or $V_H$ domain, and said polypeptide exhibit differing binding specificities. In certain embodiments of the invention, at least one antigen binding domain of the bi- or multispecific molecule of the invention immunospecifically binds to albumin. In other embodiments of the invention, at least one antigen binding domain of the bi- or multispecific molecule of the invention immunospecifically binds to fibronectin.

In certain embodiments, the immunospecific polypeptides of the invention, or antigen binding fragments thereof, do not comprise a $CH_1$ domain. In other embodiments, the immunospecific polypeptides of the invention, or epitope binding fragments thereof, do not comprise one or more of a $CH_1$ domain, $CH_2$ domain, $C_L$ domain, $CH_3$ domain, or H domain, or do not comprise any of a $CH_1$ domain, $CH_2$ domain, $C_L$ domain, $CH_3$ domain, or H domain. In still other embodiments, the immunospecific polypoeptides of the invention, or epitope binding fragments thereof, comprise one of a $CH_1$ domain, H domain, $CH_2$ domain, $C_L$ domain, or $CH_3$ domain, and do not comprise any other constant domain or hinge region derived from an immunoglobulin (for example, in certain embodiments, the immunospecific polypeptide of the invention or fragment thereof comprises a $CH_1$ domain, but does not comprise any of a(n) H domain, a $CH_2$ domain, or a $CH_3$ domain; or comprises a $CH_2$ domain, but does not comprise any of a $CH_1$ domain, H domain, or a $CH_3$ domain, etc.).

In certain embodiments, the immunospecific polypeptide of the invention comprises one or more of a $V_H$ CDR1 domain, a $V_H$ CDR2 domain, a $V_H$ CDR3 domain, a $V_L$ CDR1 domain, a $V_L$ CDR2 domain, and/or a $V_L$ CDR3 domain. In certain embodiments, the immunospecific polypeptide of the invention comprises each of a $V_H$ CDR1 domain, a $V_H$ CDR2 domain, a $V_H$ CDR3 domain, a $V_L$ CDR1 domain, a $V_L$ CDR2 domain, and/or a $V_L$ CDR3 domain.

In certain embodiments, the immunospecific polypeptide of the invention comprises one of a $V_H$ CDR1 domain, $V_H$ CDR2 domain, $V_H$ CDR3 domain, $V_L$ CDR1 domain, $V_L$ CDR2 domain, or $V_L$ CDR3 domain, but does not comprise any other CDR domain, wherein said CDR domains have been isolated and/or identified by the methods of the invention, wherein said CDR domains have been isolated and/or identified by the methods of the invention (for example, in certain embodiments, the immunospecific polypeptide of the invention comprises a $V_H$ CDR1 domain, but does not comprise a $V_H$ CDR2 domain, a $V_H$ CDR3 domain, a $V_L$ CDR1 domain, a $V_L$ CDR2 domain, or a $V_L$ CDR3 domain; or comprises a $V_H$ CDR2 domain, but does not comprise a $V_H$ CDR1 domain, a $V_H$ CDR3 domain, a $V_L$ CDR1 domain, a $V_L$ CDR2 domain, or a $V_L$ CDR3 domain; or comprises a $V_H$ CDR3 domain, but does not comprise a $V_H$ CDR1 domain, a $V_H$ CDR2 domain, a $V_L$ CDR1 domain, a $V_L$ CDR2 domain, or a $V_L$ CDR3 domain; or comprises a $V_L$ CDR1 domain, but does not comprise a $V_H$ CDR1 domain, a $V_H$ CDR2 domain, a $V_H$ CDR3 domain, a $V_L$ CDR2 domain, or a $V_L$ CDR3 domain; or comprises a $V_L$ CDR2 domain, but does not comprise a $V_H$ CDR1 domain, a $V_H$ CDR2 domain, a $V_H$ CDR3 domain, a $V_L$ CDR1 domain, or a $V_L$ CDR3 domain; or comprises a $V_L$ CDR3 domain, but does not comprise a $V_H$ CDR1 domain, a $V_H$ CDR2 domain, a $V_H$ CDR3 domain, a $V_L$ CDR1 domain, or a $V_L$ CDR2 domain).

In certain embodiments, the immunospecific polypeptide of the invention comprises any two of a $V_H$ CDR1 domain, $V_H$ CDR2 domain, $V_H$ CDR3 domain, $V_L$ CDR1 domains, $V_L$ CDR2 domain, or $V_L$ CDR3 domain, but does not comprise any other CDR domain, wherein said CDR domains have been isolated and/or identified by the methods of the invention, wherein said CDR domains have been isolated and/or identified by the methods of the invention (for example, in certain embodiments, the immunospecific polypeptide of the invention comprises a $V_H$ CDR1 domain and a $V_H$ CDR2 domain, but does not comprise a $V_H$ CDR3 domain, a $V_L$ CDR1 domain, a $V_L$ CDR2 domain, or a $V_L$ CDR3 domain; or comprises a $V_H$ CDR2 domain and, a $V_H$ CDR3 domain, but does not comprise a $V_H$ CDR1 domain, a $V_L$ CDR1 domain, a $V_L$ CDR2 domain, or a $V_L$ CDR3 domain; or comprises a $V_H$ CDR1 domain and a $V_H$ CDR3 domain, but does not comprise a $V_H$ CDR2 domain, a $V_L$ CDR1 domain, a $V_L$ CDR2 domain, or a $V_L$ CDR3 domain; or comprises a $V_L$ CDR1 domain and a $V_L$ CDR2 domain, but does not comprise a $V_H$ CDR1 domain, a $V_H$ CDR2 domain, a $V_H$ CDR3 domain, or a $V_L$ CDR3 domain; or comprises a $V_L$ CDR1 domain and a $V_L$ CDR3 domain, but does not comprise a $V_H$ CDR1 domain, a $V_H$ CDR2 domain, a $V_H$ CDR3 domain, or a $V_L$ CDR2 domain; or comprises a $V_L$ CDR2 domain and a $V_L$ CDR3 domain; but does not comprise a $V_H$ CDR1 domain, a $V_H$ CDR2 domain, a $V_H$ CDR3 domain, or a $V_L$ CDR1 domain; or comprises a $V_H$ CDR1 domain and a $V_L$ CDR1 domain, but does not comprise a $V_H$ CDR2 domain, a $V_H$ CDR3 domain, a $V_L$ CDR2 domain, or a $V_L$ CDR3 domain; or comprises a $V_H$ CDR1 domain and a $V_L$ CDR2 domain, but does not comprise a $V_H$ CDR2 domain, a $V_H$ CDR3 domain, a $V_L$ CDR1 domain, or a $V_L$ CDR3 domain; or comprises a $V_H$ CDR1 domain and a $V_L$ CDR3 domain, but does not comprise a $V_H$ CDR2 domain, a $V_H$ CDR3 domain, a $V_L$ CDR1 domain, or a $V_L$ CDR2 domain; or comprises a $V_H$ CDR2 domain and a $V_L$ CDR1 domain, but does not comprise a $V_H$ CDR1 domain, a $V_H$ CDR3 domain, a $V_L$ CDR2 domain, or a $V_L$ CDR3 domain; or comprises a $V_H$ CDR2 domain and a $V_L$ CDR2 domain, but does not comprise a $V_H$ CDR1 domain, a $V_H$ CDR3 domain, a $V_L$ CDR1 domain, or a $V_L$ CDR3 domain; or comprises a $V_H$ CDR2 domain and a $V_L$ CDR3 domain, but does not comprise a $V_H$ CDR1 domain, a $V_H$ CDR3 domain, a $V_L$ CDR1 domain, or a $V_L$ CDR2 domain; or comprises a $V_H$ CDR3 domain and a $V_L$ CDR1 domain, but does not comprise a $V_H$ CDR1 domain, a $V_H$ CDR2 domain, a $V_L$ CDR2 domain, or a $V_L$ CDR3 domain; or comprises a $V_H$ CDR3 domain and a $V_L$ CDR2 domain, but does not comprise a $V_H$ CDR1 domain, a $V_H$ CDR2 domain, a $V_L$ CDR1 domain, or a $V_L$ CDR3 domain; or comprises a $V_H$ CDR3 domain and a $V_L$ CDR3 domain, but does not comprise a $V_H$ CDR1 domain, a $V_H$ CDR2 domain, a $V_L$ CDR1 domain, ma $V_L$ CDR2 domain; or comprises two $V_H$ CDR3 domains, but does not comprise a $V_H$ CDR1 domain, a $V_H$ CDR2 domain, a $V_L$ CDR1 domain, a $V_L$ CDR2 domain or a $V_L$ CDR3 domain, or comprises; or comprises two $V_L$ CDR3 domains, but does not comprise a $V_H$ CDR1 domain, a $V_H$ CDR2 domain, a $V_H$ CDR3 domain, a $V_L$ CDR1 domain or a $V_L$ CDR2 domain, etc.).

In certain embodiments, the immunospecific polypeptide of the invention comprises any three of a $V_H$ CDR1 domain, $V_H$ CDR2 domain, $V_H$ CDR3 domain, $V_L$ CDR1 domain, $V_L$ CDR2 domain, or $V_L$ CDR3 domain, but does not comprise any other CDR domains, wherein said CDR domains have been isolated and/or identified by the methods of the invention, wherein said CDR domains have been isolated and/or identified by the methods of the invention (for example, in certain embodiments, the immunospecific polypeptide of the invention comprises a $V_H$ CDR1 domain, a $V_H$ CDR2 domain, and $V_H$ CDR3 domain, but does not comprise a $V_L$ CDR1 domain, a $V_L$ CDR2 domain, or a $V_L$ CDR3 domain; or comprises a $V_L$ CDR1 domain, a $V_L$ CDR2 domain, and $V_L$ CDR3 domain, but does not comprise a $V_H$ CDR1 domain, a $V_H$ CDR2 domain, or a $V_H$ CDR3 domain; or comprises a $V_H$ CDR1 domain, a $V_H$ CDR2 domain, and $V_L$ CDR1 domain, but does not comprise a $V_H$ CDR3 domain, a $V_L$ CDR2 domain, or a $V_L$ CDR3 domain; or comprises a $V_H$ CDR1 domain, a $V_L$ CDR1 domain, and $V_H$ CDR3 domain, but does not comprise a $V_H$ CDR2 domain, a $V_L$ CDR2 domain, or a $V_L$ CDR3 domain; or comprises two $V_H$ CDR3 domains, and $V_L$ CDR1 domain, but does not comprise a $V_H$ CDR1 domain, a $V_H$ CDR2 domain, a $V_L$ CDR2 domain or a $V_L$ CDR3 domain; etc.).

In certain embodiments, the immunospecific polypeptide of the invention comprises any four of a $V_H$ CDR1 domain, V$_H$CDR2 domain, V$_H$CDR3 domain, V$_L$ CDR1 domain, V$_L$ CDR2 domain, or V$_L$ CDR3 domain, but does not comprise any other CDR domains, wherein said CDR domains have been isolated and/or identified by the methods of the invention, wherein said CDR domains have been isolated and/or identified by the methods of the invention (for example, in certain embodiments, the immunospecific polypeptide of the invention comprises a V$_H$ CDR1 domain, a V$_H$ CDR2 domain, a V$_H$ CDR3 domain, and a V$_L$ CDR1 domain, but does not comprise a V$_L$ CDR2 domain, or a V$_L$ CDR3 domain; or comprises a V$_H$ CDR1 domain, a V$_H$ CDR2 domain, a V$_H$ CDR3 domain, and a V$_L$ CDR3 domain, but does not comprise a V$_L$ CDR1 domain, or a V$_L$ CDR32 domain; or comprises a V$_H$ CDR1 domain, a V$_H$ CDR2 domain, a V$_L$ CDR1 domain, and a V$_L$ CDR2 domain, but does not comprise a V$_H$ CDR3 domain, or a V$_L$ CDR3 domain; or comprises a V$_H$ CDR2 domain, a V$_H$ CDR3 domain, a V$_L$ CDR2 domain, and a V$_L$ CDR3 domain, but does not comprise a V$_H$ CDR1 domain, or a V$_L$ CDR1 domain; or comprises two V$_H$ CDR3 domains, and two V$_L$ CDR3 domains, but does not comprise a V$_H$ CDR1 domain, a V$_H$ CDR2 domain, a V$_H$ CDR1 domain, or a V$_L$ CDR2 domain; etc.).

In certain embodiments, the immunospecific polypeptide of the invention comprises any five of a V$_H$ CDR1 domain, V$_H$ CDR2 domain, V$_H$ CDR3 domain, V$_L$ CDR1 domain, V$_L$ CDR2 domain, or V$_L$ CDR3 domain, but does not comprise any other CDR domains, wherein said CDR domains have been isolated and/or identified by the methods of the invention, wherein said CDR domains have been isolated and/or identified by the methods of the invention (for example, in certain embodiments, the immunospecific polypeptide of the invention comprises a V$_H$ CDR1 domain, a V$_H$ CDR2 domain, a V$_H$ CDR3 domain, a V$_L$ CDR1 domain and a V$_L$ CDR2 domain, but does not comprise a V$_L$ CDR3 domain; or comprises a V$_L$ CDR1 domain, a V$_L$ CDR2 domain, a V$_L$ CDR3 domain, a V$_H$ CDR2 domain and a V$_H$ CDR3 domain, but does not comprise a V$_B$ CDR1 domain; etc.).

In certain embodiments, the immunospecific polypeptide of the invention comprises one or more of the framework domains isolated and/or identified by the methods of the invention. In specific embodiments, the immunospecific polypeptide of the present invention comprises the framework domains identified herein with heterologous CDR sequences grafted therein.

The polypeptides of the invention include immunoglobulin molecules that may derived from any species (e.g., rabbit, mouse, rat), but are preferably human immunoglobulin molecules that can be of any type (e.g., IgG, IgE, IgM, IgD, IgA and IgY), or class (e.g., IgG$_1$, IgG$_2$, IgG$_3$, IgG$_4$, IgA$_1$, and IgA$_2$) or subclass. The immunospecific polypeptides, e.g., antibodies, of the invention, or antigen binding fragments thereof, can be produced by any method known in the art, for example, chemical synthesis or recombinant techniques.

In certain embodiments, the immunospecific polypeptide of the invention does not comprise a V$_H$ domain, e.g., a rabbit V$_H$ domain, and/or does not comprise a V$_H$ domain derived from any species other than rabbit. In other embodiments, the immunospecific polypeptide of the invention does not comprise a V$_L$ domain and/or does not comprise a V$_L$ domain derived from any species other than rabbit. In preferred embodiments, the immunospecific polypeptide of the invention comprises a V$_H$ domain, and does not comprise a V$_L$ domain. In other embodiments, the immunospecific polypeptide of the invention comprises a V$_L$ domain, and does not comprise a V$_H$ domain. In specific embodiments, the immunospecific polypeptides of the invention, e.g., antibodies, comprise one or more of a V$_H$ FR1 domain having the amino acid sequence QEQLMETESGGGAEG-GLVKPGASLTLTCTAS (SEQ ID NO:57); a V$_H$ FR2 domain having the amino acid sequence WVRQAPGK-GLEWIG (SEQ ID NO:69); a V$_H$ FR3 domain having the amino acid sequence YATWVNGRFTLSRDIDQSTG-CLQLNSLTAADTATYYCAR (SEQ ID NO:95); a V$_H$ FR4 domain having the amino acid sequence WGQGTLVTVSS (SEQ ID NO:139); a V$_L$ FR1 domain having the amino acid sequence ELVLTQTPPSLSASVGETVRIRC (SEQ ID NO:150) or ELVLTQTPSSVSAAVGGTVTINC (SEQ ID NO:155); a V$_L$ FR2 domain having the amino acid sequence WYQQKPEKPPTLLIS (SEQ ID NO:174) or WYQQK-PGQRPKLLIY (SEQ ID NO:181); a V$_L$ FR3 domain having the amino acid sequence GVPPRFSGSGSGTDYTLTIG-GVQAEDVATYYC (SEQ ID NO:183) or GVSSRFK-GSGSGTQFTLTISGVQCADAATYYC (SEQ ID NO:205); or a V$_L$ FR4 domain having the amino acid sequence FGAGTNVEIK (SEQ ID NO:206) or FAFGGGTELEIL (SEQ ID NO:210). In other embodiments, the immunospecific polypeptides of the invention, e.g., antibodies or antigen binding fragments thereof (e.g., single variable domains), comprise one or more of a V$_H$ FR1 domain from Table 3, a V$_H$ FR2 domain from Table 4, V$_H$ FR3 domain from Table 5 at, a V$_H$ FR4 domain from Table 6, a V$_L$ FR1 domain from Table 7, a V$_L$ FR2 domain from Table 8, a V$_L$ FR3 domain from Table 9, or a V$_L$ FR4 domain from Table 10 in Section 6.1.2.

In further specific embodiments, the immunospecific polypeptides of the invention, e.g., antibodies, comprise one or more scaffold residues that improve stability and/or antigen binding affinity of the peptides. In certain embodiments the immunospecific polypeptides of the invention comprise one or more of a phenylalanine at position 46 in the V$_H$ FR2 domain; a glutamic acid at position 53 in the V$_H$ FR2 domain; an arginine at position 54 in the V$_H$ FR2 domain; a glycine at position 56 in the V$_H$ FR2 domain; an alanine at position 58 in the V$_H$ FR2 domain; a cysteine at position 44 in the V$_H$ CDR1 domain; a cysteine at position 59 in the V$_H$ CDR2 domain; an arginine at position 126 in the V$_H$ FR4 domain; a phenylalanine or a tyrosine at position 39 in the V$_L$ FR2 domain; a lysine at position 45 in the V$_L$ FR2 domain; or a cysteine at position 91 in the V$_L$ FR3 domain, wherein said positions are according to the V$_H$ or V$_L$ domain amino acid sequence alignments presented in FIGS. 3 and 4, respectively.

The present invention also encompasses the use of immunospecific polypeptides or fragments thereof comprising the amino acid sequence of any of the variable domains, CDRs, amino acid scaffold sequences (e.g., framework domains such as those listed in Tables 3-10 in Section 6.1.2), or amino acid scaffold residues of the invention with mutations (e.g., one or more amino acid substitutions) in any of the above. In specific examples in accordance with this embodiment, the present invention encompasses immunospecific polypeptides comprising one or more amino acid substitutions, wherein said substitutions result in one or more of, at position 46 in the V$_H$ FR2 domain, a phenylalanine; at position 53 in the V$_H$ FR2 domain, a glutamic acid; at position 54 in the V$_H$ FR2 domain, an arginine; at position 56 in the V$_H$ FR2 domain, a glycine; at position 58 in the V$_H$ FR2 domain, an alanine; at position 44 in the V$_H$ CDR1 domain, a cysteine; at position 59 in the V$_H$ CDR1 domain, a cysteine; at position 126 in the V$_H$ FR4 domain, a cysteine; at position 39 in the V$_L$ FR2 domain, a phenylalanine or a tyrosine; at position 45 in the V$_L$ FR2 domain, a lysine; or at position 91 in the $V_L$ FR3 domain, a cysteine. Preferably, mutations in these regions, domains or residues maintain or enhance the avidity and/or affinity of the immunospecific polypeptide for the antigen, i.e. epitope, to which they immunospecifically bind. The recited positions are according to the $V_H$ or $V_L$ domain amino acid sequence alignments presented in FIGS. 3 and 4, respectively.

In certain embodiments, the polypeptides of the invention, or antigen binding fragments thereof immunospecifically bind an epitope of an antigen which is immuno-neutral or non-immunogenic in mice and/or rats.

The present invention also encompasses immunospecific polypeptides of the invention that have been modified by any method known in the art and/or described herein known to increase or improve the serum half-life of therapeutic polypeptides. Non-limiting examples of such modifications include pegylation, acetylation and the use of non-natural amino acids. In certain embodiments the serum half-life of the immunospecific polypeptide may be increased or improved by including in the polypeptide an additional antigen binding domain, which domain immunospecifically binds to albumin or fibronectin.

The methods of the invention also encompass polynucleotides that encode the immunospecific polypeptides of the invention. In one embodiment, the invention provides an isolated nucleic acid sequence encoding a $V_H$ or $V_L$ domain identified or constructed by the methods described herein. The invention further encompasses polynucleotides that encode immunospecific polypeptides, e.g., antibodies or antigen binding fragments thereof, comprising novel (relative to the amino acid sequences of immunoglobulins of species other than rabbit) scaffold amino acid sequences, novel amino acid residues at particular positions of the $V_H$ or $V_L$ amino acid sequence, or novel amino acid sequences of CDR loops identified by the methods described herein. The invention further relates to a vector comprising said nucleic acid. In specific embodiments wherein the immunospecific polypeptide of the invention comprises both a $V_H$ and a $V_L$ domain identified, isolated or constructed by the methods of the invention, the invention provides a vector comprising a first nucleic acid molecule encoding said $V_H$ domain and a second nucleic acid molecule encoding said $V_L$ domain, said $V_H$ and $V_L$ domains independently or concomitantly selected for immunospecific binding to the same antigen and/or epitope. In one specific embodiment, said vector is an expression vector. The invention further provides host cells containing the vectors of polynucleotides encoding the polypeptides of the invention.

The present invention encompasses immunospecific polypeptides, e.g., antibodies, recombinantly fused or chemically conjugated (including both covalently and non-covalently conjugations) to therapeutic agents or additional antigen binding domains, e.g., heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences or through chemical conjugation. The immunospecific polypeptides of the invention may be used for example to target the therapeutic agent to particular cell types, either in vitro or in vivo, by fusing or conjugating the agent to the immunospecific polypeptides of the present invention that are specific, for particular cell surface receptors. In other embodiments, the additional antigen binding domains may be used to bind the immunospecific polypeptides of the invention to albumin or fibronectin, thereby improving serum half-life (see, e.g., Holt et al., 2008, Protein Eng Des Sel 21:283-288 and Stork et al., 2007, Protein Eng Des Sci 20:569-576, each of which is hereby incorporated by reference herein in its entirety). The therapeutic-agent/immunospecific polypeptide fusions of the invention may also be used in in vitro immunoassays and purification methods using methods known in the art. See e.g., PCT publication Number WO 93/21232; EP 439,095; Naramura et al., Immunol. Lett., 39:91-99, 1994; U.S. Pat. No. 5,474,981; Gillies et al., PNAS, 89:1428-1432, 1992; and Fell et al., J. Immunol., 146:2446-2452, 1991, which are incorporated herein by reference in their entireties. Therapeutic agents for use in accordance with the methods of the invention are not to be construed as limited to classical chemical therapeutic agents (e.g., chemotherapeutics), but may include peptides that may or may not modify or alter biological responses, drug moieties, radioactive materials, macrocyclic chelators, and siRNA. In non-limiting examples, such polypeptides as therapeutic agents may include albumin, protamine, albumin interacting proteins (e.g., gp60, gp30, gp18), protein A, a G protein, protein transduction domains (see e.g., Bogoyevitch et al., 2002, DNA Cell Biol 12:879-894, hereby incorporated by reference in its entirety), toxins, cytotoxins, or portions of antibody molecules (e.g., Fc domain, $CH_1$ domain, $CH_1$ domain, $CH_1$ domain, CL domain, etc.); such radionuclides may include radionuclides (e.g., alpha-, beta-, gamma-emitters, etc.) known in the art for labeling (i.e., producing a detectable signal in vivo or in vitro) and/or producing a therapeutic effect (e.g., $^{125}I$, $^{131}I$, $^{14}C$, etc.); such macrocyclic chelators include those known in the art for conjugating radiometal ions (e.g., DOTA).

In a certain embodiments, the CDR and/or framework regions of the immunospecific polypeptides of the invention are derived from rabbit $V_H$ or $V_L$ regions identified or isolated by the methods described herein. In other embodiments, the CDR and/or framework regions of the immunospecific polypeptides of the invention are not derived from rabbit $V_H$ or $V_L$ regions identified or isolated by the methods described herein, but comprise novel scaffold amino acid sequences and/or novel amino acid residues at certain positions of the amino acid sequence of the $V_H$ or $V_L$ domains identified by the methods of the invention. In some embodiments, the immunospecific polypeptides of the invention described herein comprise additional alterations, including, but not limited to, amino acid deletions, insertions, and modifications, of the $V_H$ and/or $V_L$ sequences isolated and identified herein.

Preferably, the immunospecific polypeptides, e.g. antibodies, of the invention, or antigen binding fragments thereof, are monoclonal (i.e., bind the same epitope of an antigen), and in certain embodiments may be humanized.

The invention further provides a pharmaceutical composition comprising (i), and (ii) a pharmaceutically acceptable carrier In certain embodiments of the invention, pharmaceutical compositions are provided for use in accordance with the methods of the invention, said pharmaceutical compositions comprising a therapeutically effective amount of an immunospecific polypeptide of the invention, or antigen binding fragment thereof, and a pharmaceutically acceptable carrier.

3.1 Definitions

As used herein, the term "analog" in the context of proteinaceous agents (e.g., proteins, polypeptides, and antibodies) refers to a proteinaceous agent that possesses a similar or identical function as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous, amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a polypeptide can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence; see, e.g. FIGS. 3-4). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous agent refers to a second organic or inorganic molecule which possess a similar or identical function as a first organic or inorganic molecule and is structurally similar to the first organic or inorganic molecule.

As used herein, the term "derivative" in the context of polypeptides or proteins, including immunospecific polypeptides (e.g., antibodies), refers to a polypeptide or protein that comprises an amino acid sequence which has been altered by the introduction of amino acid residue substitutions, deletions or additions. The term "derivative" as used herein also refers to a polypeptide or protein which has been modified, i.e., by the covalent attachment of any type of molecule to the polypeptide or protein. For example, but not by way of limitation, an immunospecific polypeptide of the invention may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

As used herein, the term "epitope" refers to a region on an antigen molecule to which an antibody specifically binds. Antigen molecules can comprise single or multiple epitopes.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide. Preferably, fragments of the immunospecific polypeptides of the invention are antigen binding fragments (in particular, epitope binding fragments).

As used herein, the terms "heavy chain," "light chain," "variable region," "framework region," "constant domain," and the like, have their ordinary meaning in the immunology art and refer to domains in naturally occurring immunoglobulins and the corresponding domains of synthetic (e.g., recombinant) binding proteins (e.g., humanized antibodies, single chain antibodies, chimeric antibodies, etc.). The basic structural unit of naturally occurring immunoglobulins (e.g., IgG) is a tetramer having two light chains and two heavy chains, usually expressed as a glycoprotein of about 150,000 Da. The amino-terminal ("N") portion of each chain includes a variable region of about 100 to 110 or more amino acids primarily responsible for antigen recognition. The carboxy-terminal ("C") portion of each chain defines a constant region, with light chains having a single constant domain and heavy chains usually having three constant domains and a hinge region. Thus, the structure of the light chains of an immunoglobulin molecule, e.g., IgG, is n-$V_L$--$C_L$-c and the structure of heavy chains of an immunoglobulin molecule, e.g., IgG, is n-$V_H$--$C_{H1}$--H--$C_{H2}$--$C_{H3}$-c (where H is the hinge region). The variable regions of the immunospecific polypeptides of the invention, e.g., antibodies, consist of the complementarity determining regions (CDRs), which contain the residues in contact with antigen and non-CDR segments, referred to as framework segments, which in general maintain the structure and determine the positioning of the CDR loops (although certain framework residues may also contact antigen). Thus, the $V_L$ and $V_H$ domains have the structure n-FR1, CDR1, FR2, CDR2, FR3, CDR3, FR4-c.

As used herein, the terms "humanized antibody" or "humanized immunospecific polypeptide" refer to a polypeptide comprising at least one immunoglobulin variable comprising a human framework region and one or more CDRs identified by the methods of the invention. In some embodiments, the immunospecific polypeptide of the invention does not comprise an entire immunoglobulin, or may comprise a single immunoglobulin variable domain (e.g., a $V_H$ or $V_L$ domain) and but not comprise any other immunoglobulin domain or region (e.g., Fc, $CH_1$, $CH_2$, $CH_3$, CL, etc.). The immunospecific polypeptide (e.g., antibody or variable domain) providing the CDRs is called the "donor" and the human immunoglobulin, or fragment thereof (e.g., variable domain) providing the framework is called the "acceptor". Constant regions need not be present, but if they are, they must be substantially identical to human immunoglobulin constant regions, i.e., at least about 85-90%, preferably about 95% or more identical. Hence, in accordance with embodiments wherein the immunospecific polypeptide of the invention comprises a humanized immunoglobulin, all parts of a said immunoglobulin, except possibly the CDRs, are substantially identical to corresponding parts of natural human immunoglobulin sequences. In the context of immunospecific polypeptides as used herein, i.e., polypeptides comprising at least a variable domain (or epitope binding fragment thereof), humanized molecules of the invention, e.g., antibodies, do not encompass chimeric molecules of the invention because, e.g., the entire variable region of the chimeric molecule would non-human. One says that the donor molecule has been "humanized", by the process of "humanization", because the resultant humanized molecule is expected to bind to the same antigen as the donor antibody that provides the CDRs. Generally, humanized immunospecific molecules are human immunoglobulins (or variable domains and/or fragments thereof), the recipient molecule, in which hypervariable region residues of the recipient are replaced by hypervariable region residues from a non-human species (donor antibody; e.g., donor CDRs from a rabbit $V_H$ or $V_L$ domain) having the desired specificity, affinity, and capacity. In some instances, Framework Region (FR) residues of the human immunoglobulin, or fragment thereof, are replaced by corresponding non-human residues. Furthermore, humanized molecules may comprise residues which are not found in the recipient antibody or in the donor antibody. These modifications are made to further refine functionality, e.g., immunospecificity. In general, the humanized molecule, e.g., antibody, will comprise substantially all of at least one, and typically two, variable domains, in which all or substantially all of the hypervariable regions correspond to those of a non-human immunoglobulin or variable domain and all or substantially all of the FRs are those of a human immunoglobulin sequence. The humanized molecule optionally also will comprise at a CL and/or a $CH_1$ domain and/or least a portion of an immunoglobulin constant region (Fc). In some embodiments, a humanized molecule of the invention is a derivative. Such a humanized molecule comprises amino acid residue substitutions, deletions or additions in one or more of the non-human, e.g., rabbit, CDRs. The derivative of the humanized molecule of the invention may have substantially the same binding, better binding, or worse binding when compared to a non-derivative humanized molecule of the invention. In specific embodiments, one, two, three, four, or five amino acid residues of the CDRs identified and/or constructed in accordance with the methods of the invention have been substituted, deleted or added (i.e., mutated). For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565, 332, 5,585,089, 5,766,886, and 6,407,213; and Padlan, 1991, Molecular Immunology 28(4/5):489-498; Studnicka et al., 1994, Protein Engineering 7(6):805-814; Roguska et al., 1994, Proc Natl Acad Sci USA 91:969-973; Tan et al., 2002, J. Immunol. 169:1119-25; Caldas et al., 2000, Protein Eng. 13:353-60; Morea et al., 2000, Methods 20:267-79; Baca et al., 1997, J. Biol. Chem. 272:10678-84; Roguska et al., 1996, Protein Eng. 9:895-904; Couto et al., 1995, Cancer Res. 55 (23 Supp):5973s-5977s; Couto et al., 1995, Cancer Res. 55:1717-22; Sandhu, 1994, Gene 150:409-10; Pedersen et al., 1994, J. Mol. Biol. 235:959-73; Jones et al., 1986, Nature 321:522-525; Reichmann et al., 1988, Nature 332: 323-329; and Presta, 1992, Curr. Op. Struct. Biol. 2:593-596 (each of which is hereby incorporated by reference herein in its entirety). The term "humanization" also includes methods of protein and/or antibody resurfacing such as those disclosed in U.S. Pat. Nos. 5,770,196; 5,776,866; 5,821,123; and 5,896,619, each to Studnicka et al. (each of which is incorporated herein by reference in its entirety).

As used herein, the terms "immunospecifically binds," "immunospecifically recognizes," "specifically binds," "specifically recognizes" and analogous terms refer to molecules that specifically bind to an antigen (e.g., epitope or immune complex) and do not specifically bind to another molecule. A molecule that specifically binds to an antigen may bind to other peptides or polypeptides with lower affinity as determined by, e.g., immunoassays, BIAcore, or other assays known in the art. Preferably, molecules that specifically bind an antigen do not cross-react with other proteins. Molecules that specifically bind an antigen can be identified, for example, by immunoassays, BIAcore or other techniques known to those of skill in the art.

As used herein, the terms "immunospecific polypeptides" and "immunospecific polypeptide" refer to polypeptides, peptides, and/or proteins that comprise at least one of a $V_H$ or a $V_L$ domain and exhibit immunospecific binding as determined by any method known in the art for assessing antigen/antibody specificity (e.g., BIAcore). The terms may refer to polyclonal antibodies, monoclonal antibodies, multispecific antibodies, humanized antibodies, synthetic antibodies, chimeric antibodies, polyclonal antibodies, single-chain Fvs (scFv), single chain antibodies, anti-idiotypic (anti-Id) antibodies (including, e.g., anti-Id and anti-anti-Id antibodies to antibodies of the invention), diabodies (see e.g., U.S. Patent Application Publication Nos. 2007/0004909 and 2006/0210564, each of which is hereby incorporated by reference herein in its entirety), minibodies (see, e.g., U.S. Pat. No. 5,837,821 and U.S. Patent Application Publication No. 2007/0003556, each of which is hereby incorporated by reference herein in its entirety), nanobodies (see, e.g., Revets et al., 2005, Expert Opin Biol Ther 5:111-124, hereby incorporated by reference in its entirety), or antigen binding fragments of any of the above, including, but not limited to, Fab fragments, F(ab') fragments, disulfide-linked bispecific Fvs (sdFv), and intrabodies. The terms also include immunoglobulin molecules and immunologically active fragments of immunoglobulin molecules, i.e., molecules that contain an antigen binding site, and may be of any type (e.g., IgG, IgE, IgM, IgD, IgA and IgY), class (e.g., $IgG_1$, $IgG_2$, $IgG_3$, $IgG_4$, $IgA_1$, and $IgA_2$) or subclass. The terms may also refer to bispecific or multispecific molecules comprising two or more antigen binding molecules, at least one of which is a $V_H$ or a $V_L$ domain determined by the methods of the invention, or at least one of which comprises a variable domain framework region determined by the methods of the invention.

When referring to immunospecific polypeptides of the invention, e.g., antibodies, (as broadly defined herein), the assignment of amino acids to each domain is in accordance with methods well known in the art for the characterization of antibody variable domains, including, e.g., variable domains of human, murine and rabbit variable domains. Amino acids from the rabbit variable domain of mature heavy and light chains as isolated and identified by the methods of the present invention are designated by their position in the alignment sequences presented in FIG. 3 for the $V_H$ domain and in FIG. 4 for the $V_L$ domain. For example, the FR1 domain of a rabbit $V_H$ domain isolated and/or identified by the methods of the invention typically comprises from 24 to 31 amino acid residues, each of which is designated by their position in an alignment sequence based on the longest amino acid sequence for each domain (see, e.g., FIG. 4). Accordingly, a specific variable domain may or may not comprise a residue at a particular position of the alignment sequence. The alignments presented in FIGS. 3-4 and specific domain determinations of the polypeptides of the invention were determined according to methods known in the art for characterizing and aligning sequences based on immunoglobulin molecules (e.g., aligned according to Kabat *Sequences of Proteins of Immunological Interest*, 5$^{th}$ Ed. Public Health Service, NH1, MD (1991), expressly incorporated herein by references). Thus, as presented in FIG. 3, in the alignment sequence of the $V_H$ domain, the FR1 consists of positions 1-31, the CDR1 of positions 32-44, the FR2 of positions 45-58, the CDR2 of positions 59-69, the FR3 of positions 70-110, the CDR3 of positions 111-125, and the FR4 of positions 126-136; and as presented in FIG. 4, in the alignment sequence of the $V_L$ domain the FR1 consists of positions 1 to 23, the CDR1 of positions 24 to 37, the FR2 of positions 38-52, the CDR2 of positions 53 to 59, the FR3 of positions 60 to 91, the FR4 of positions 92-105, and the FR4 of positions 106-116B.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the terms "prophylactic agent" and "prophylactic agents" refer to any agent(s) which can be used in the prevention of a disorder, or prevention of recurrence or spread of a disorder. A prophylactically effective amount may refer to the amount of prophylactic agent sufficient to prevent the recurrence or spread of a disease, the recurrence or exacerbation of symptoms of a disease, or the occurrence of such in a subject. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease.

As used herein, the terms "single-chain Fv" or "scFv" refer to antibody fragments that comprise the VH and VL domains of antibody, wherein these domains are present in a single polypeptide chain. Generally, the Fv polypeptide further comprises a polypeptide linker between the VH and VL domains which enables the scFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994). In specific embodiments, scFvs include bi-specific scFvs and humanized scFvs.

As used herein, the term "stable" in the context of a formulation comprising an immunospecific polypeptide of the invention refers to a formulation in which the protein therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993) (each of which is hereby incorporated by reference in its entirety). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation following lyophilization and storage can be used as an indicator of protein stability. For example, a "stable" formulation may be one wherein less than about 10% and preferably less than about 5% of the protein is present as an aggregate in the formulation. In other embodiments, any increase in aggregate formation following lyophilization and storage of the lyophilized formulation can be determined. For example, a "stable" lyophilized formulation may be one wherein the increase in aggregate in the lyophilized formulation is less than about 5% and preferably less than about 3%, when the lyophilized formulation is stored at 2-8° C. for at least one year. In other embodiments, stability of the protein formulation may be measured using a biological activity assay.

As used herein, the term "stable" in the context of an immunospecific polypeptide of the invention may refer to the kinetic stability of a protein, or the resistance of a protein to unfolding. Kinetic stability can be best explained by illustrating the unfolding process as a simple equilibrium reaction between two protein conformations, the native folded state (N) and the unfolded state (U), which is normally separated by a higher energy transition state (TS). Since the height of the TS barrier determines the rate of folding and unfolding, kinetically stable proteins possess an unusually high energy TS, which results in extremely slow unfolding rates that virtually trap the protein in its native state. Even though the overall change in Gibbs free energy ($\Delta G$) may be favorable for unfolding under extreme solvent conditions, such as high concentrations of denaturant, the high activation energy of the TS significantly slows the unfolding rate of kinetically stable proteins. Methods to asses the stability of polypeptides are well known in the art and include, e.g., single molecule force spectroscopy, assessment of thermal denaturation, e.g., monitored by dynamic light scattering ("DLS"), and resistance to SDS denaturation (see, e.g., U.S. Patent Application publication 2006/0099647, hereby incorporated by reference in its entirety). Stability may also be assessed by the characteristics of protein expression in recombinant expression systems. Polypeptides that readily fold, and which are resistant to unfolding, will be expressed as soluble protein in such systems, while improperly or only partially folded proteins interact via their hydrophobic regions to form inclusion bodies. The inventors have additionally implemented a stability assay based on the solubility of recombinant protein, wherein said protein is expressed as a fusion with CAT and the CAT activity of the fusion is evaluated (see, infra).

As used herein, the terms "subject" and "patient" are used interchangeably. As used herein, a subject is preferably a mammal such as a non-primate (e.g., cows, pigs, horses, cats, dogs, rats etc.) or a primate (e.g., monkey and human), most preferably a human. As used herein, a "therapeutically effective amount" refers to that amount of the therapeutic agent of the invention sufficient to treat or manage a disease or disorder. A therapeutically effective amount may refer to the amount of therapeutic agent sufficient to delay or minimize the onset of disease. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of an amount of therapeutic agent of the invention sufficient to treat or manage a disease.

4. BRIEF DESCRIPTION OF THE FIGURES

Figures 2A, 2B:
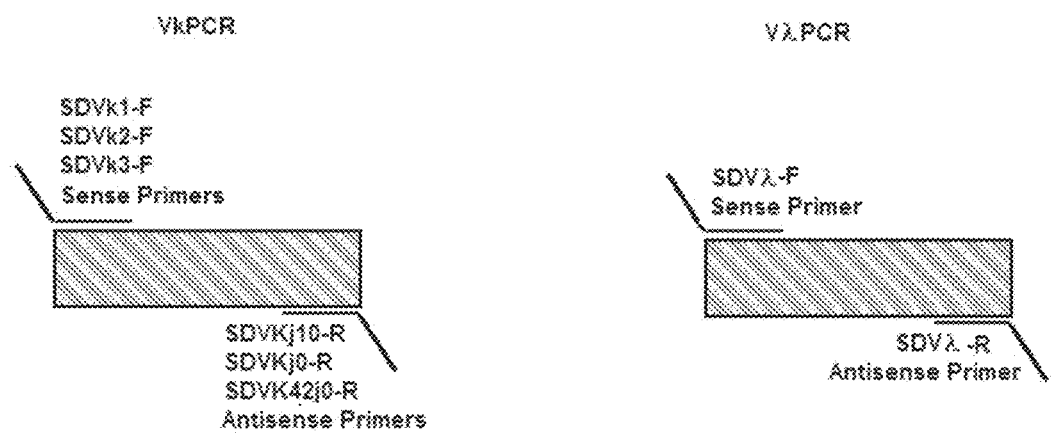

FIG. 1 Schematic representation of primer position in the nucleotide sequence of the heavy chain variable domain FIG. 2A-2B Schematic representation of primer position in the nucleotide sequence of the light chain variable domain; (A) κ chain; (B) λ chain.

FIG. 3 Exemplary alignment of amino acid sequences of heavy chain variable domains ($V_H$ domains) selected by the methods of the invention.

FIG. 4 Exemplary alignment of amino acid sequences of light chain variable domains ($V_L$ domains) selected by methods of the invention.

Figure 5:
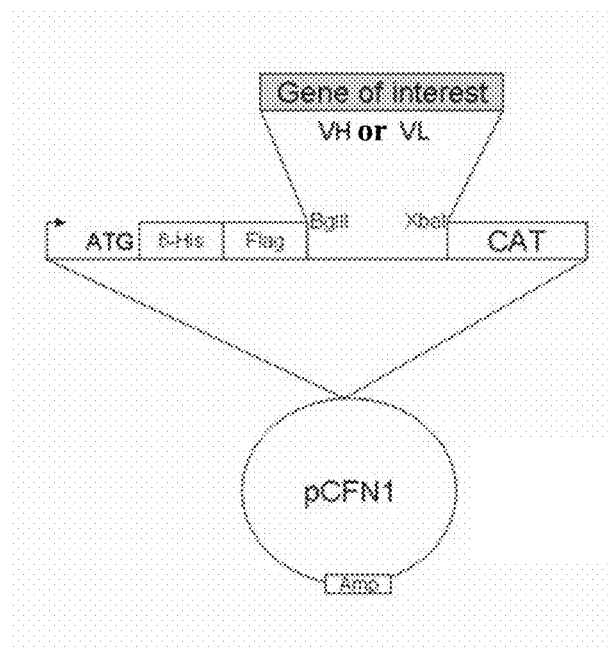

FIG. 5 Schematic representation of expression vector allowing expression of SDVL and/or SDVH domains as fusion proteins with CAT.

Figure 6A:
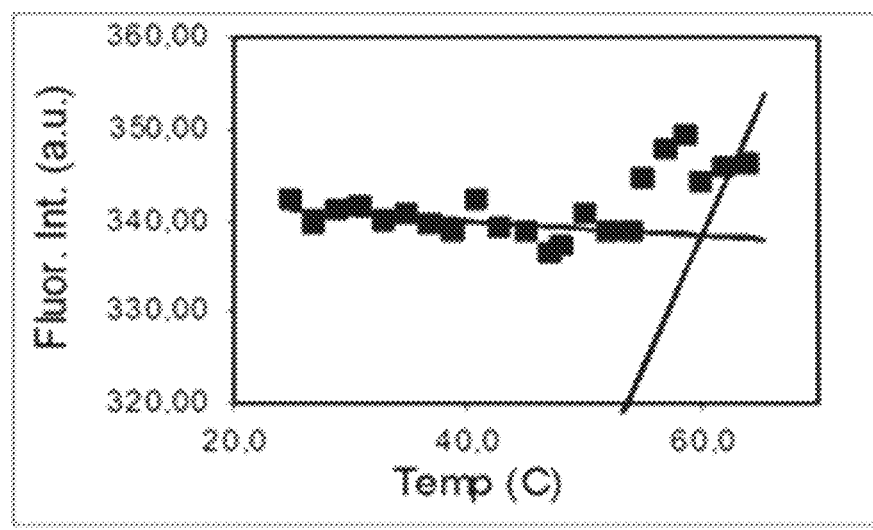
Figure 6B:
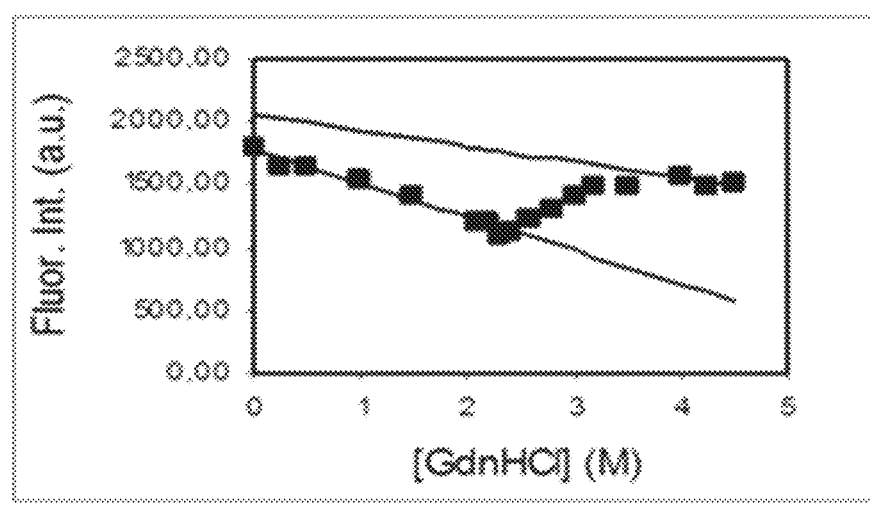

FIG. 6A-B Intrinsic fluorescence of the unfolding transition curves of a representative SDVL domain of the invention. (A) Heat induced unfolding; (B) GdmCl induced unfolding.

5. DETAILED DESCRIPTION

5.1 Immunospecific Polypeptides

The present invention relates to modified, engineered immunospecific polypeptides, e.g., antibodies, having $V_H$ and or $V_L$ domains, or portions thereof (e.g., CDR domains, framework domains, etc.) derived from rabbits. In preferred embodiments, the present invention encompasses single domain antibodies derived from rabbit immunoglobulin variable domains and/or epitope binding fragments thereof. The present inventors have discovered that rabbit variable domains maintain unique stability, and retain high binding affinity when recombinantly expressed as single domains.

The present invention encompasses methods for the isolation and use of rabbit $V_H$ and/or $V_L$ domains and/or novel CDR and framework regions derived therefrom. The invention further provides for the identification of novel amino acid sequences (including novel amino acid residues at defined positions) within isolated rabbit $V_H$ and $V_L$ domains for use as "scaffold" or structural sequences in the context of CDR loops and/or framework regions in recombinant immunospecific polypeptides. The rabbit scaffold sequences (including scaffold residues) or novel CDR/framework sequences of the invention enhance the stability and/or affinity of the variable domain(s) and/or immunospecific polypeptides (e.g., antibodies) that contain them, in particular, relative to rodent antibodies, enabling the production and/or use of highly specific, single domain immunopeptides, e.g., single domain antibodies.

The present invention encompasses the production of novel rabbit $V_H$ or $V_L$ domains with specificity for a given antigen, or epitope thereof. In particular, the invention provides for a method of producing rabbit $V_H$ or $V_L$ domains said method comprising: (a) selecting from a phage expression library a set of DNA sequences that encode rabbit $V_H$ or $V_L$ domains that immunospecifically bind to a desired antigen or epitope thereof (also known as phage "panning") and (b) expressing the set of sequences, or a subset thereof, in bacteria as a fusion protein with chloramphenicol acetyltransferase ("CAT") and selecting bacteria that have chloramphenicol resistance by virtue of CAT expression. In alternate embodiments, the present invention provides for a method of producing rabbit $V_H$ or $V_L$ domains, said method comprising (a) expressing sequences of DNA or cDNA encoding $V_H$ or $V_L$ domains of rabbit immunoglobulins in bacteria as a fusion protein with CAT, (b) selecting bacteria that have chloramphenicol resistance by virtue of CAT expression and obtaining the set of DNA sequences encoding the rabbit $V_H$ or $V_L$ domains from the selected bacteria, and (c) preparing a phage expression library from the set of DNA sequences obtained in step (b) and selecting DNA sequences that encode $V_H$ or $V_L$ domains that immunospecifically bind to a desired antigen or epitope thereof (i.e., panning the library for immunospecific binding to the antigen or epitope). In certain embodiments, the present invention encompasses methods for the production of a rabbit $V_H$ or $V_L$ domain wherein the phage panning step is repeated one or more times. In related embodiments, the phage palming step may or may not be repeated sequentially. The phage expression library for use in accordance with the present invention may be obtained commercially or prepared by any method described herein and/or known in the art. Expression of DNA or cDNA sequences in bacteria as fusion proteins is well known and may be performed by any method described herein or known in the art, e.g., cloning the DNA or cDNA sequence encoding the $V_H$ or $V_L$ domain into an expression vector that comprises a nucleotide sequence encoding CAT and a promoter sequence that drives fusion protein expression. The invention further encompasses the $V_H$ and/or $V_L$ domain, or fragments thereof, produced by the methods described herein. The invention also encompasses the novel scaffold amino acid sequences or scaffold amino acid residues (at defined positions of the variable domain of the invention) isolated and/or identified by these methods.

In one embodiment, the present invention provides single domain antibodies comprising two $V_H$ domains. In another embodiment, the present invention provides a fragment of a single domain antibody comprising one VH domain. In still other embodiments, the invention provides an immunospecific polypeptide comprising a single $V_H$ or $V_L$ domain and not comprising any other immunoglobulin derived domain (e.g., CL domain, $CH_1$ domain, $CH_2$ domain, $CH_3$ domain, Fc domain, etc.). Prior to the instant invention, single domain antibodies were based primarily on the antibodies of the genus *Camelus*, i.e., camelized single domain antibodies (See e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231:25; International Publication Nos. WO 94/04678 and WO 94/25591; U.S. Pat. No. 6,005,079; which are incorporated herein by reference in their entireties). In certain embodiments the immunospecific polypeptides of the invention are bispecific or multispecific. Bi- or multi-specific molecules of the invention may be formed using any method known in the art and/or described herein, e.g., formed by the creation of a fusion or conjugate peptide. The bispecific or multispecifc molecules of the invention comprise at least one $V_H$ or $V_L$ domain, or at least one framework region of a variable domain, identified, isolated or constructed according to the methods of the invention. In certain embodiments, a certain embodiments, the bispecific or multispecific molecule of the invention comprises more than one $V_L$ and/or more than one $V_L$ domain, which domains were isolated, identified and/or constructed by the methods of the invention.

Immunospecific polypeptides, e.g., antibodies, of the invention include, but are not limited to single domain antibodies, monoclonal antibodies, multispecific antibodies, humanized antibodies, synthetic antibodies, chimeric antibodies, polyclonal antibodies, single-chain Fvs (scFv), single chain antibodies, anti-idiotypic (anti-Id) antibodies (including, e.g., anti-Id and anti-anti-Id antibodies to antibodies of the invention), diabodies, minibodies, nanobodies, or antigen binding fragments of any of the above, including, but not limited to, Fab fragments, F(ab') fragments, disulfide-linked bispecific Fvs (sdFv), and intrabodies, and epitope binding fragments thereof. In particular, the immunospecific polypeptides, e.g., antibodies, of the present invention include single domain antibodies or immunoglobulin molecules and immunologically active portions of immunoglobulin molecules.

The CDRs, scaffold amino acid sequences and/or scaffold amino acid residues of the immunospecific polypeptides, e.g., antibodies, of the present invention may be derived from any member of the Leporidae family (e.g., rabbits and hares) and are preferably derived from rabbits (e.g., New Zealand White rabbits). In certain embodiments, the polypeptides of the invention are humanized monoclonal antibodies.

The present invention also encompasses immunospecific polypeptides or fragments thereof comprising an amino acid sequence of a framework domain that is at least 45%, at least 50%, at least 55%, at least 60%, at least 65%, at least 70%, at least 75%, at least 80%, at least 85%, at least 90%, at least 95%, or at least 99% identical to the amino acid sequence of a framework domain of the invention. In certain embodiments, the invention encompasses framework domains that comprise 1, 2, 3, 4, 5, 6, 7, 8, 9, or 10 amino acid modifications (e.g., insertion, substitution, deletion, etc.) relative to a framework domain of the invention. The present invention further encompasses immunospecific polypeptides or fragments thereof comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the invention. In certain embodiments, the invention encompasses CDRs that comprise 1, 2, 3, 4, or 5 amino acid modifications (e.g., insertion, substitution, deletion, etc.) relative to a CDR of the invention. The determination of percent identity of two amino acid sequences can be determined by any method known to one skilled in the art.

The present invention also encompasses the use of immunospecific polypeptides or fragments thereof comprising the amino acid sequence of any of the variable domains, CDRs, amino acid scaffold sequences, or amino acid scaffold residues (e.g., in the heavy chain variable domain FR2 positions 46, 53, 54, 56 and 58, in the heavy chain domain CDR1 positions 44 and 59, in the heavy chain variable domain FR4 position 126, in the light chain variable domain FR2 positions 39 and 45, and in the light chain variable domain FR3 position 91) of the invention with mutations (e.g., one or more amino acid substitutions) in any of the above. In specific examples in accordance with this embodiment, the present invention encompasses immunospecific polypeptides comprising one or more amino acid substitutions, wherein said substations result in one or more of, at position 46 in the $V_H$ FR2 domain, a phenylalanine; at position 53 in the $V_H$ FR2 domain, a glutamic acid; at position 54 in the $V_H$ FR2 domain, an arginine; at position 46 in the $V_H$ FR2 domain, a glycine; at position 58 in the $V_H$ FR2 domain, an alanine; at position 44 in the $V_H$ CDR1 domain, a cysteine; at position 59 in the $V_H$ CDR1 domain, a cysteine; at position 126 in the $V_H$ FR4 domain, a cysteine; at position 39 in the $V_L$ FR2 domain, a phenylalanine or a tyrosine; at position 45 in the $V_L$ FR2 domain, a lysine; or at position 91 of the $V_L$ FR3 domain, a cysteine. Preferably, mutations in these regions, domains or residues maintain or enhance the avidity and/or affinity of the immunospecific polypeptide for the antigen, i.e. epitope, to which they immunospecifically bind. Standard techniques known to those skilled in the art (e.g., immunoassays) can be used to assay the affinity of an immunospecific polypeptide, e.g., antibody, for a particular antigen.

In other embodiments, the present invention encompasses the use of immunospecific polypeptides or fragments thereof comprising amino acid sequences of any of the variable domains, CDRs, amino acid scaffold sequences, or comprising the amino acid scaffold residues (e.g., in the heavy chain variable domain FR2 positions 46, 53, 54, 56 and 58, in the heavy chain domain CDR1 positions 44 and 59, in the heavy chain variable domain FR4 position 126, in the light chain variable domain FR2 positions 39 and 45, and in the light chain variable domain FR3 position 91) identified herein. In certain embodiments, the present invention encompasses Immunospecific polypeptides having one or more of, at position 46 in the $V_H$ FR2 domain, a phenylalanine; at position 53 in the $V_H$ FR2 domain, a glutamic acid; at position 54 in the $V_H$ FR2 domain, an arginine; at position 46 in the $V_H$ FR2 domain, a glycine; at position 58 in the $V_H$ FR2 domain, an alanine; at position 44 in the $V_H$ CDR1 domain, a cysteine; at position 59 in the $V_H$ CDR1 domain, a cysteine; at position 126 in the $V_H$ FR4 domain, a cysteine; at position 39 in the $V_L$ FR2 domain, a phenylalanine or a tyrosine; at position 45 in the $V_L$ FR2 domain, a lysine; or at position 91 of the $V_L$ FR3 domain, a cysteine. The scaffold residues identified herein may maintain pr enhance the avidity and/or affinity of the immunospecific polypeptide for the antigen, i.e. epitope, to which they immunospecifically bind, in particular, for embodiments of the invention comprising single domain binding proteins, i.e., a polypeptide comprising only a single $V_L$ or $V_H$ domain and not comprising any other immunoglobulin variable domain. Standard techniques known to those skilled in the art (e.g., immunoassays) can be used to assay the affinity of an immunospecific polypeptide, e.g., antibody, for a particular antigen.

The polypeptides used in the methods of the invention include derivatives that are modified, i.e., by the covalent attachment of any type of molecule to the immunospecific polypeptide of the present invention. For example, but not by way of limitation, derivatives include immunospecific polypeptides that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

In certain embodiments, the immunospecific molecules of the invention are modified to increase serum half-life in vivo. Methods well known in the art to increase serum half-life include conjugation or fusion to antibody constant regions including, but not limited to, antibody constant regions including Fc and/or hinge regions (see for example, U.S. Pat. Nos. 5,565,335, and 6,277,375, each hereby incorporated by reference in its entirety, including all references cited therein), and/or other known elements such as interferon and/or thymosin targeting peptides, and permeability increasing proteins (see, e.g., U.S. Pat. Nos. 6,319,691 and 5,643,570, respectively, each of which is incorporated herein by reference in its entirety, including all references cited within each respective patent). Where the immunospecific molecule of the invention comprises an IgG constant domain, such modifications can also include introduction of one or more amino acid modifications (i.e., substitutions, insertions or deletions) into said constant domain, or, preferably into an FcRn binding fragment thereof (preferably a Fc or hinge-Fc domain fragment). See, e.g., International Publication No. WO 98/23289; International Publication No. WO 97/34631; and U.S. Pat. No. 6,277,375, each of which is incorporated herein by reference in its entirety. Other modifications known in the art to extend the life of the molecules of the invention, include the use non-natural amino acids, for example in the D form, or, alternatively or additionally, the use of amino acid analogs, such as sulfur-containing forms of amino acids. Alternatively, the polynucleotides and genes of the invention can be recombinantly fused to elements that are useful in the preparation of immunogenic constructs for the purposes of vaccine formulation or elements useful for the isolation of the polypeptides provided.

The molecules of the invention may contain modifications to the C- and/or N-terminus which include, but are not limited to amidation or acetylation. In certain embodiments, the amino acid residues contain reactive side chains, for example carboxy side chain in glutamic acid, that can be capped by capping groups known in the art. Acetylation refers to the introduction of a $COCH_3$ group either at the amino terminus or on the side chain(s) of at least one lysine in the peptide(s) or peptide fragment(s). Importantly, acetylation can regulate protein stability. For example, analysis of in vivo acetylated E2F1 shows that the acetylated version has a longer half-life (Martinez-Balbás et al., (2000) *EMBO J.* 19(4):662-71; see also Takemura et al. (1992) *J Cell Sci.* 103 (Pt 4):953-64; each of which reference is hereby incorporated in its entirety). Accordingly, in certain embodiments, the amino-terminal of the immunospecific molecules of the invention are modified by acetylation. In certain embodiments, a lysine side chain in the immunospecific molecule is modified. In yet other embodiments, the immunospecific molecule of the invention is acetylated both at the amino terminus and on a lysine side chain.

The present invention also encompasses the use of immunospecific polypeptides comprising the amino acid sequence of any of the immunospecific polypeptides of the invention with mutations (e.g., one or more amino acid substitutions) in the framework or variable regions. Preferably, mutations in these regions maintain or enhance the avidity and/or affinity of the antibodies for the particular antigen(s), and/or epitope, to which they immunospecifically bind. Standard techniques known to those skilled in the art (e.g., immunoassays) can be used to assay the affinity of an antibody for a particular antigen.

Standard techniques known to those skilled in the art can be used to introduce mutations in the nucleotide sequence encoding an immunospecific polypeptide of the invention, or fragment thereof, including, e.g., site-directed mutagenesis and PCR-mediated mutagenesis, which results in amino acid substitutions. In certain embodiments, the derivatives have conservative amino acid substitutions made at one or more predicted non-essential amino acid residues.

The present invention also encompasses the use of immunospecific polypoeptides comprising the amino acid sequence of any of the immunospecific polypeptides of the invention with mutations (e.g., one or more amino acid substitutions) in the framework or variable regions. Preferably, mutations in these regions maintain or enhance the avidity and/or affinity of the antibodies for the particular antigen(s), and/or epitope, to which they immunospecifically bind. Standard techniques known to those skilled in the art (e.g., immunoassays) can be used to assay the affinity of an antibody for a particular antigen.

Immunospecific polypeptides of the invention, or fragments thereof, with increased in vivo half-lives can be generated by attaching to said polypeptides or fragments to polymer molecules such as high molecular weight polyethyleneglycol (PEG). PEG can be attached to said polypeptides or fragments with or without a multifunctional linker either through site-specific conjugation of the PEG to the N- or C-terminus of said polypeptides or fragments or via epsilon-amino groups present on lysine residues. Linear or branched polymer derivatization that results in minimal loss of biological activity can be used. The degree of conjugation can be closely monitored by SDS-PAGE, and mass spectrometry to ensure proper conjugation of PEG molecules to the immunospecific polypeptides or fragments of the invention. Unreacted PEG can be separated from polypeptide-PEG conjugates by, e.g., size exclusion or ion-exchange chromatography.

For some uses, including in vivo use in humans and in vitro detection assays, it may be preferable to use chimeric or humanized molecules.

Nucleic acid sequences encoding rabbit $V_H$ or $V_L$ domains that immunospecifically bind to an antigen and/or an epitope are selected for both affinity and stability using sequential screening methods for each characteristic. Using the methods of the invention, initial pools encoding rabbit variable domains will become enriched in sequences encoding immunospecific polypeptides, e.g., rabbit variable domains, that exhibit high affinity for an antigen of interest as well as high stability (e.g., the capacity to be properly expressed and folded in recombinant systems, the capacity to resist degradation or aggregation in these systems, an to retain its functional characteristic of immunospecific binding). In certain embodiments, the polypeptides encoded by the sequences are selected for immunospecific binding to an antigen prior to being selected for stability. In other embodiments, the polypeptides encodes by the sequences are selected for stability prior to being selected for immunospecific binding to an antigen. The invention encompasses methods wherein the either or both of the binding selection and/or stability selection step(s) is repeated one or more times. The invention further encompasses methods wherein the binding selection and stability selection steps, and/or repeats thereof, are performed in any order one or more times.

5.1.1 Affinity Selection Using Phage Display

Rabbit $V_H$ or $V_L$ domains that immunospecifically bind to an antigen and/or an epitope are selected using the various phage display and panning methods known in the art. Using phage display methods, functional rabbit variable domains are displayed on the surface of phage particles which carry the polynucleotide sequences encoding them. The phage particles are then contacted with an antigen and/or epitope of interest and the particles exhibiting immunospecific binding to said antigen and/or epitope are selected or identified using methods well known in the art, e.g., using labeled antigen or antigen bound or captured to a solid surface or bead. Examples of phage display methods that can be used in accordance with the methods of the invention include those disclosed in Brinkman et al., J. Immunol. Methods, 182:41-50, 1995; Ames et al., J. Immunol. Methods, 184:177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

The phage display libraries for use in the methods of the invention may be obtained commercially or derived from the antibody repertoires of naïve or immunized rabbits as described herein and/or known in the art. As is known in the art, the polypeptide encoded by the nucleic acid in the phagemid vector, and thus expressed on the surface of the phage, may be a single rabbit $V_H$ or $V_L$ domain, may be a single chain antibody, may be a scFv or may be any fragment of the rabbit heavy or light chain. In certain embodiments, each phage particle expresses a single variable domain on its surface. In alternate embodiments, the phage particle expresses a $V_H$ and a $V_L$ domain on its surface, such that the $V_H$ and $V_L$ domains interact to form binding pair.

The phage particles used in phage display and panning methods are filamentous phage and may be selected from class I phages (e.g., fd, M13, f1, If1, ke, ZJ/Z, Ff, etc.) or class II phages (e.g., Xf, Pf1, Pf3, etc.), or derivatives thereof. The nucleotide sequences encoding the portions of the rabbit heavy and/or light chains, e.g., rabbit $V_H$ or $V_L$ domains, are expressed from a phagemid vector, which drives expression of the sequence in the host cell (i.e., bacteria) as a fusion with the gene III capsid protein (pIII) of phage fd or its counterpart in another filamentous phage. Phage display technology encompasses the use of a helper phage, or a plasmid encoding complementing phage genes, to help package the phagemid genome, wherein the pIII fusion protein is a capsid protein therefor.

Individual phage particles expressing the portions of the rabbit, heavy or light chains, and thus comprising the nucleotide sequence encoding said portions, that exhibit specificity for a desired antigen can be isolated from the library using screening methods known in the art (see, e.g., Gherardi et al., 1990, J Immunol Meth 126:61-68, hereby incorporated by reference herein in its entirety). Selection may be accomplished by anchoring the antigen and/or epitope of interest to a solid surface (e.g., culture dish, microtitre plate, chromatography beads, magnetic beads, etc.) and passing the library of phage particles over the bound antigen ad/or epitope. Those individual phage that bind are retained after washing and optionally detected by any detection system known in the art (e.g., anti-fd antibody-enzyme conjugates). In specific embodiments, the pIII fusion protein further comprises a target amino acid sequence to facilitate detection by anti-target antibody-enzyme conjugates. Bound phage particles may be removed under increasingly stringent wash conditions to select for increasing binding affinity. The stringency of the wash condition can be increased by any method known in the art, e.g., by alteration of the wash pH, by increasing the time of the wash, by adding detergent to the wash solution, etc. In specific embodiments, the set of bound phage particles is collected and re-selected for immunospecific binding to target antigen and/or epitope one or more times. Phage display selection may be performed before or after or both before and after selection of polypeptides of the invention by stability analysis.

Phage display technology can be used to increase the affinity of an immunospecific polypeptide of the invention for a target antigen and/or epitope. The technology, referred to as affinity maturation, employs mutagenesis or CDR walking and re-selection using target antigen and/or an epitope thereof to identify amino acid sequences of the invention that bind with higher affinity to the antigen when compared with the initial pool of selected sequences. Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (See Wu et al., 1998, Proc Natl. Acad. Sci. USA 95:6037; Yelton et al., 1995, J. Immunology 155:1994, each of which is hereby incorporated by reference herein in its entirety). The binding specificity of the polypeptides of the invention may be evaluated by any method known in the art for determining binding-pair interactions, including, but not limited to ELISA, western blot, surface plasmon resonance (e.g., BIAcore) and radioimmunoassay. Any method known in the art for assessing binding polypeptide specificity may be used to identify polypeptides of the invention that exhibit a Kd of greater than 0.001 nM but not greater than 5 nM, not greater than 10 nM, not greater than 15 nM, not greater than 20 nM, not greater than 25 nM, not greater than 30 nM, not greater than 35 nM, not greater than 40 nM, not greater than 45 nM, or not greater than 50 nM. In certain embodiments, the isolated $V_H$ or $V_L$ domains of the invention exhibit a Kd of no greater than 5 nM, no greater than 10 nM, no greater than 15 nM, no greater than 20 nM, no greater than 25 nM, no greater than 30 nM, no greater than 35 nM, no greater than 40 nM, no greater than 45 nM, or no greater than 50 nM as determined by BIAcore assay.

The present invention also provides for immunospecific polypeptides of the invention, or fragments thereof, that have a high binding affinity for the antigen of interest. In a specific embodiment, an immunospecific polypeptide of the present invention or fragment thereof has an association rate constant or $k_{on}$ rate (antibody (Ab)+antigen (Ag) Ab-Ag) of at least $10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7$ $M^{-1}$ $s^{-1}$, or at least $10^8$ $M^{-1}$ $s^{-1}$. In a preferred embodiment, an immunospecific polypeptide of the present invention or fragment thereof has a $k_{on}$ of at least $2\times10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7$ $M^{-1}$ $s^{-1}$, or at least $10^8$ $M^{-1}$ $s^{-1}$.

In another embodiment, an immunospecific polypeptide of the present invention or fragment thereof has a $k_{off}$ rate (antibody (Ab)+antigen (Ag) Ab-Ag) of less than $10^{-1}$ $s^{-1}$, less than $5\times10^{-1}$ $s^{-1}$, less than $10^{-2}$ $s^{-1}$, less than $5\times10^{-2}$ $s^{-1}$, less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7}$ $s^{-1}$, less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$. In a preferred embodiment, an immunospecific polypeptide of the present invention or fragment thereof has a $k_{off}$ of less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7}$ $s^{-1}$, less than $5\times10^{-7}$ $s^{-1}$, less than $10^{-8}$ $s^{-1}$, less than $5\times10^8$ $s^{-1}$, less than $10^{-9}$ $s^{-1}$, less than $5\times10^{-9}$ $s^{-1}$, or less than $10^{-10}$ $s^{-1}$.

In still other embodiments, an immunospecific polypeptide of the present invention or fragment thereof has an affinity constant or $K_a$ ($k_{on}/k_{off}$) of at least $10^2$ $M^{-1}$, at least $5\times10^2$ $M^{-1}$, at least $10^3$ $M^{-1}$, at least $5\times10^3$ $M^{-1}$, at least $10^4$ $M^{-1}$, at least $5\times10^4$ $M^{-1}$, at least $10^5$ $M^{-1}$, at least $5\times10^5$ $M^{-1}$, at least $10^6 M^{-1}$, at least $5\times10^6$ $M^{-1}$, at least $10^7$ $M^{-1}$, at least $5\times10^7$ $M^{-1}$, at least $10^8$ $M^{-1}$, at least $5\times10^8$ $M^{-1}$, at least $10^9$ $M^{-1}$, at least $5\times10^9$ at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$. In yet another embodiment, an immunospecific polypeptide of the present invention or fragment thereof has a dissociation constant or $K_d$ ($k_{off}/k_{on}$) of less than $10^{-2}$ M, less than $5\times10^{-2}$ M, less than $10^{-3}$ M, less than $5\times10^{-3}$ M, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{-11}$ M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M.

5.1.2 Solubility/Stability Selection of Immunospecific Polypeptides

Nucleotide sequences encoding rabbit $V_H$ or $V_L$ domains that exhibit high stability are selected using a modified chloramphenicol resistance assay. The assay selects for polypeptides that exhibit remain soluble, are properly folded, and resist aggregation during recombinant expression.

The method of stability selection is based on assessing solubility of the recombinant protein as expressed in *E. coli* as a fusion with chloramphenicol acetyltransferase ("CAT"), the enzyme responsible for conferring bacterial resistance to the antibiotic chloramphenicol. CAT is a highly soluble homotrimeric protein of 25 kDa molecular weight that has been shown to maintain activity when fused to a variety of other proteins (Robben et al., 1993, Gene 126:109-113). The level of activity of CAT in fusion proteins (and thus resistance to chloramphenicol), however, is significantly lower when the gene is expressed in a fusion protein with insoluble protein than when expressed as a construct with soluble protein. Accordingly, soluble forms of the polypeptides of the invention (e.g., rabbit $V_H$ and $V_L$ domains) can be selected out of a large pool of potential proteins by selection with chloramphenicol. Bacteria comprising the nucleotide sequences of the invention may be selected using liquid media or bacterial plates. The present invention encompasses methods comprising culturing said transformed bacteria on selective media comprising at least 0.1 mM, at least 0.2 mM, at least 0.4 mM, at least 0.6 mM, at least 0.8 mM, at least 1.0 mM, at least 1.2 mM, at least 1.4 mM, at least 1.6 mM, at least 1.8 mM, at least 2.0 mM, at least 2.5 mM, at least 3.0 mM, at least 5.0 mM, at least 10 mM, at least 15 mM, or at least 20 mM chloramphenicol. The bacteria may be transformed, and the DNA extracted from the selected bacteria, by any method known in the art.

The invention also encompasses other assays known in the art for evaluation of protein stability. Nonlimiting examples of such assays are single molecule force spectroscopy, assessment of alterations in intrinsic fluorescence, assessment of thermal denaturation, e.g., monitored by dynamic light scattering ("DLS"), and resistance to SDS denaturation (see, e.g., U.S. Patent Application publication 2006/0099647, hereby incorporated by reference in its entirety). The methods of the present invention further encompass determination of the Gibbs free energy of folding ($\Delta G_{N-U}$) as a method of determining stability. In certain embodiments $\Delta G_{N-U}$ of the molecules of the invention is about 1 kJ/mol, about 2 kJ/mol, about 0.4 kJ/mol, about 6 kJ/mol, about 8 kJ/mol, about 10 kJ/mol, about 12 kJ/mol, about 14 kJ/mol, about 16 kJ/mol, about 18 kJ/mol, about 20 kJ/mol, about 21 kJ/mol, about 22 kJ/mol, about 23 kJ/mol, about 24 kJ/mol, about 25 kJ/mol, about 26 kJ/mol, about 27 kJ/mol, about 28 kJ/mol, about 29 kJ/mol, about 30 kJ/mol, about 32 kJ/mol, about 34 kJ/mol, about 36 kJ/mol, about 38 kJ/mol, about 40 kJ/mol, about 45 kJ/mol, or about 50 kJ/mol.

Any other method known in the art for monitoring protein folding/unfolding may also be used in accordance with the methods of the invention.

5.2 Humanized Molecules

In preferred embodiments, the immunospecific polypeptides of the invention and/or fragments thereof are humanized. A humanized molecule of the present invention is a polypeptide comprising at least one immunoglobulin variable domain (or a variant or fragment thereof) that is capable of immunospecifically binding to a predetermined antigen and that comprises a framework region having substantially the amino acid sequence of a human immunoglobulin and a CDR having substantially the amino acid sequence of a rabbit immunoglobulin isolated and/or identified by the methods described herein. A humanized immunospecific polypeptide of the invention may comprise substantially all of at least one, or, in certain embodiments, two, variable domains in which all or substantially all of the CDR regions correspond to those of a rabbit variable domain isolated/identified by the methods of the present invention (i.e., donor domain/regions) and all or substantially all of the framework regions are those of a human immunoglobulin consensus sequence. In certain embodiments, a humanized molecule of the invention also comprises at least a portion of an immunoglobulin constant region (Fc), typically that of a human immunoglobulin. The constant domains of the humanized molecules of the invention may be selected with respect to the proposed function of the immunospecific polypeptide, e.g., antibody, in particular the effector function which may be required. In some embodiments, the constant domains of the humanized molecules of the invention are human IgA, IgE, IgG or IgM domains. In a specific embodiment, human IgG constant domains, especially of the IgG1 and IgG3 isotypes are used, when the humanized molecules of the invention are intended for therapeutic uses and antibody effector functions are desired. In alternative embodiments, IgG2 and IgG4 isotypes are used when the humanized molecule of the invention is intended for therapeutic purposes and antibody effector function is not required.

In some embodiments, the immunospecific polypeptides of the invention comprise only a heavy chain, only a light chain, only a $V_H$ domain, only a $V_L$ domain, or any combination of the above fragments and/or domains. In other embodiments, the immunospecific polypeptide, or fragment, of the invention may further comprise none, one, or one or more of the CH1, hinge, CH2, CH3, and CH4 regions of the heavy chain. In other embodiments, the immunospecific polypeptide, or fragment, of the invention does not comprise a CL domain. The immunospecific polypeptide, or fragment, of the invention may comprise a receptor antibody selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the humanized molecule, e.g., antibody, exhibit cytotoxic activity, and the class is typically $IgG_1$. In other embodiments, where such cytotoxic activity is not desirable, the constant domain may be of the $IgG_2$ class. The humanized molecule of the invention may comprise sequences from more than one class or isotype, and selecting particular constant domains to optimize desired effector functions is within the ordinary skill in the art.

The framework and CDR regions of a humanized molecule of the invention need not correspond precisely to the parental sequences, e.g., the donor rabbit CDR or the consensus framework may be mutagenized by substitution, insertion or deletion of at least one residue so that the CDR or framework residue at that site does not correspond to either the consensus or the donor molecule. Such mutations, however, are preferably not extensive. Usually, at least 75% of the humanized residues will correspond to those of the parental framework region (FR) and CDR sequences, more often 90%, and most preferably greater than 95%. Humanized molecules, in particular, antibodies, can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, Proc Natl Acad Sci USA 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, J. Immunol. 169:1119-25, Caldas et al., 2000, Protein Eng. 13:353-60, Morea et al., 2000, Methods 20:267-79, Baca et al., 1997, J. Biol. Chem. 272:10678-84, Roguska et al., 1996, Protein Eng. 9:895-904, Couto et al., 1995, Cancer Res. 55 (23 Supp):5973s-5977s, Couto et al., 1995, Cancer Res. 55:1717-22, Sandhu, 1994, Gene 150:409-10, Pedersen et al., 1994, J. Mol. Biol. 235:959-73, Jones et al., 1986, Nature 321:522-525, Riechmann et al., 1988, Nature 332:323, and Presta, 1992, Curr. Op. Struct. Biol. 2:593-596. Often, framework residues in the framework regions will be substituted with the corresponding residue from the CDR or the donor rabbit variable domain to alter, preferably improve, antigen binding (i.e., substitution the scaffold amino acid sequences and/or residues identified by the methods of the present invention). These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323, all of which are incorporated herein by reference in their entireties)). The term "humanization" also includes methods of protein and/or antibody resurfacing such as those disclosed in U.S. Pat. Nos. 5,770,196; 5,776,866; 5,821,123; and 5,896,619, each to Studnicka et al. (each of which is incorporated herein by reference in its entirety).

In some embodiments, the immunospecific polypeptides, or fragments thereof, of the invention comprise a humanized molecule wherein at least one CDR from the donor rabbit variable domain is grafted onto the recipient framework region. In other embodiments, at least two and preferably all three CDRs of the donor rabbit $V_H$ and/or $V_L$ domains are grafted onto the recipient framework regions.

5.3 Chimeric Molecules

A chimeric molecule of the invention is a molecule in which different portions of the immunospecific polypeptide are derived from different immunoglobulin molecules such as molecules having a variable region derived from a rabbit heavy chain or light chain and a human immunoglobulin constant region. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807,715, 4,816,567, and 4,816,397, which are incorporated herein by reference in their entirety. Chimeric molecules of the invention comprising one or more CDRs from the rabbit donor molecules of the invention and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, PNAS 91:969), and chain shuffling (U.S. Pat. No. 5,565,332). Each of the above-identified references is incorporated herein by reference in its entirety.

Often, framework residues in the framework regions will be substituted with the corresponding residue from the CDR rabbit donor variable domains to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al., 1988, Nature 332:323, which are incorporated herein by reference in their entireties).

5.4 Conjugate Molecules

The present invention encompasses immunospecific polypeptides, e.g., antibodies, recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. The immunospecific polypeptides of the invention may be used for example to target heterologous polypeptides to particular cell types, either in vitro or in vivo, by fusing or conjugating the heterologous polypeptides to molecules of the invention that exhibit immunospecificity for particular cell surface receptors. Alternatively or additionally, the heterologous polypeptides, in particular antigen binding heterologous polypeptides, may be used for example to target the immunospecific polypeptides of the invention to particular serum proteins or protein targets, either in vitro or in vivo, by fusing or conjugating the molecules of the invention to heterologous polypeptides that exhibit immunospecificity for particular c serum proteins or target proteins. Such fusions or conjugations result in bispecific or multispecific polypeptides of the invention. The immunospecific polypeptides of the invention fused or conjugated to heterologous polypeptides may also be used in in vitro immunoassays and purification methods using methods known in the art. See e.g., PCT Publication No. WO 93/21232; EP 439,095; Naramura et al., 1994, Immunol. Lett., 39:91-99; U.S. Pat. No. 5,474,981; Gillies et al., 1992, Proc Natl Acad Sci, 89:1428-1432; and Fell et al., 1991, J. Immunol., 146:2446-2452, each of which is incorporated herein by reference in its entirety.

Further, an immunospecific polypeptide of the invention may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin (i.e., PE-40), or diphtheria toxin, ricin, gelonin, and pokeweed antiviral protein, a protein such as tumor necrosis factor, interferons including, but not limited to, .alpha.-interferon (IFN-.alpha.), .beta.-interferon (IFN-.beta.), nerve growth factor (NGF), platelet derived growth factor (PDGF), tissue plasminogen activator (TPA); an apoptotic agent (e.g., TNF-.alpha., TNF-.beta., AIM I as disclosed in PCT Publication No. WO 97/33899), AIM II (see, e.g., PCT Publication No. WO 97/34911), Fas Ligand (Takahashi et al., 1994, J. Immunol., 6:1567-1574), and VEGI (PCT Publication No. WO 99/23105), a thrombotic agent or an anti-angiogenic agent (e.g., angiostatin or endostatin), or a biological response modifier such as, for example, a lymphokine (e.g., interleukin-1, ("IL-1"), interleukin-2 ("IL-2"), interleukin-6 ("IL-6"), granulocyte macrophage colony stimulating factor ("GM-CSF"), and granulocyte colony stimulating factor ("G-CSF")), macrophage colony stimulating factor, ("M-CSF"), or a growth factor (e.g., growth hormone ("GH"); a protease, or a ribonuclease.

Immunospecific polypeptides of the invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA, 86:821-824. Other peptide tags useful for purification include, but are not limited to, the hemagglutinin "HA" tag, which corresponds to an epitope derived from the influenza hemagglutinin protein (Wilson et al., 1984, Cell, 37:767, hereby incorporated by reference in its entirety) and the "flag" tag (Knappik et al., 1994, Biotechniques, 17(4):754-761, hereby incorporated by reference in its entirety).

The present invention further includes the use of compositions comprising heterologous polypeptides fused or conjugated to fragments of the molecules of the invention. For example, the heterologous polypeptides may be fused or conjugated to a Fab fragment, Fc fragment, Fv fragment, F(ab)$_2$ fragment, scFv, minibody, nanobody or portion thereof. Methods for fusing or conjugating polypeptides to antibody portions are known in the art. See, e.g., U.S. Pat. Nos. 5,336,603, 5,622,929, 5,359,046, 5,349,053, 5,447, 851, and 5,112,946; EP 307,434; EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341 (said references incorporated by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of the immunospecific polypeptides of the invention, e.g., antibodies, or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16:76; Hansson, et al., 1999, J. Mol. Biol. 287:265; and Lorenzo and Blasco, 1998, BioTechniques 24:308 (each of these patents and publications are hereby incorporated by reference in its entirety). Nucleic acids of the invention or fragments thereof, or the encoded polypeptides or fragments thereof, may be altered by being subjected to random mutagenesis by error-prone PCR, random nucleotide insertion or other methods prior to recombination.

The present invention also encompasses immunospecific polypeptides conjugated to a diagnostic or a therapeutic agent. Such molecules can be used diagnostically to, for example, monitor the development or progression of a disease, disorder or infection as part of a clinical testing procedure to, e.g., determine the efficacy of a given treatment regimen. Detection can be facilitated by coupling the polypeptide of the invention to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the immunospecific polypeptide of the invention or indirectly, through an intermediate (such as, for example, a linker known in the art) using techniques known in the art. See, for example, U.S. Pat. No. 4,741,900 (hereby incorporated by reference in its entirety) for metal ions which can be conjugated to antibodies for use as diagnostics according to the present invention. Such diagnosis and detection can be accomplished by coupling the polypeptide of the invention to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi) carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions. Additionally, any of the above tracer radio metals may exhibit therapeutic effect when conjugated to an immunospecific polypeptide in accordance with the methods of the invention.

An immunospecific polypeptide of the invention may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In certain embodiments, the immunospecific polypeptide of the invention can be conjugated to a therapeutic moiety such as siRNA useful for the treatment or prevention of diseases that are caused by over-expression or misexpression of genes and diseases brought about by expression of genes that contain mutations. The mechanisms of siRNA activity and it mode of use are well known in the art, see, e.g., Provost et al., 2002, EMBO J., 21: 5864-5874; Tabara et al., 2002, Cell 109:861-71; Ketting et al., 2002, Cell 110:563; and Hutvagner & Zamore, 2002, Science 297: 2056, each of which is hereby incorporated by reference herein in its entirety.

Moreover, an immunospecific polypeptide of the invention can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N", N"-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50 each incorporated by reference in their entireties.

The immunospecific polypeptide of the invention may be conjugated to a therapeutic moiety that does not alter or modify biological response, but instead functions in targeting and/or transport of the immunospecific polypeptide or fragment thereof. Nonlimiting examples of such moieties include protein A, G proteins, albumin, albumin interacting peptides (e.g., gp60, gp30, gp18; see, e.g., Schnitzer et al., 1992, J Biol Chem 34:24544-24553); and protein transduction domains (see, e.g., Bogoyevitch et al, 2002, DNA Cell Biol 12:879-894) (each of the references cited above hereby incorporated by reference herein in its entirety). Such moieties also include moties that improve or increase the serum half-life of the immunospecific polypeptides of the invention. Nonlimiting examples of moieties that increase or improve the serum half-life of polypeptides include albumin and fibronenctin, or active fragments thereof, as well as albumin and/or fibronectine binding proteins, e.g., albumin and/or fibronectin binding antibodies, or antigen binding fragments thereof (see, e.g., Holt et al., 2008, Protein Eng Des Sel 21:238-288; Weimer et al., 2008, Thromb Haemost 99:659-667; Yazaki et al., 2008, Nucl Med Biol 35:151-158; Huang et al., 2007, J Pept Sci 12:588-595; and Stork et al., 2007, Protein Eng Des Sel 20:569-576, each of which is hereby incorporated by reference in its entirety).

Techniques for conjugating such therapeutic moieties to polypeptides are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al., Immunol. Rev., 62:119-58, 1982 (each of which reference is hereby incorporated herein by reference in its entirety).

The immunospecific polypeptide of the invention, or an epitope binding fragment thereof, with or without a therapeutic moiety conjugated to it, administered alone or in combination with cytotoxic factor(s) and/or cytokine(s) can be used as a prophylactic or therapeutic.

Alternatively, an immunospecific polypeptide of the invention can be conjugated to a second antibody to form an antibody heteroconjugate as described by Segal in U.S. Pat. No. 4,676,980, which is incorporated herein by reference in its entirety.

Molecules of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The invention also encompasses the use of liposomes for prolonging or increasing the serum half-life of molecules of the invention. In certain embodiments an immunospecific molecule of the invention of the invention, e.g., comprising a $V_L$ or $V_H$ domain, may be conjugated to liposomes using previously described methods, see, e.g., Martin et al., 1982, J. Biol. Chem. 257: 286-288, which is incorporated herein by reference in its entirety. The invention thus encompasses methods of preparing liposomes with a prolonged serum half-life, i.e., enhanced circulation time, such as those disclosed in U.S. Pat. No. 5,013,556. Preferred liposomes used in the methods of the invention are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome see, e.g., Bendas et al., 2001 BioDrugs, 15(4): 215-224; Allen et al., 1987 FEBS Lett. 223: 42-6; Klibanov et al., 1990 FEBS Lett., 268: 235-7; Blum et al., 1990, Biochim. Biophys. Acta., 1029: 91-7; Torchilin et al., 1996, J. Liposome Res. 6: 99-116; Litzinger et al., 1994, Biochim. Biophys. Acta, 1190: 99-107; Maruyama et al., 1991, Chem. Pharm. Bull., 39: 1620-2; Klibanov et al., 1991, Biochim Biophys Acta, 1062; 142-8; Allen et al., 1994, Adv. Drug Deliv. Rev, 13: 285-309; all of which are incorporated herein by reference in their entirety. The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter.

5.5 Preparation and Characterization of Polypeptides of the Invention

The immunospecific polypeptides, or fragments thereof, of the invention may be characterized for specific binding to an antigen and/or epitope using any immunological or biochemical based method known in the art for characterizing binding pair interactions. Specific binding of an immunospecific polypeptide of the invention to an antigen and/or epitope may be determined for example using immunological or biochemical based methods including, but not limited to, an ELISA assay, surface plasmon resonance assays, immunoprecipitation assay, affinity chromatography, and equilibrium dialysis. Immunoassays which can be used to analyze immunospecific binding and cross-reactivity of the molecules of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

Immunospecific polypeptides, or fragments thereof, of the invention may also be assayed using any surface plasmon resonance based assays known in the art for characterizing the kinetic parameters of the interaction of the immunospecific protein with an antigen and/or epitope of interest. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al., 2000, Methods 22: 77-91; Dong et al., 2002, Review in Mol. Biotech., 82: 303-23; Fivash et al., 1998, Current Opinion in Biotechnology 9: 97-101; Rich et al., 2000, Current Opinion in Biotechnology 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety.

Briefly, SPR based assays involve immobilizing a member of a binding pair on a surface, and monitoring its interaction with the other member of the binding pair in solution in real time. SPR is based on measuring the change in refractive index of the solvent near the surface that occurs upon complex formation or dissociation. The surface onto which the immobilization occur is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Nonlimiting examples of sensor chips include those available from BIAcore AB, Inc., e.g., Sensor Chip CM5, SA, NTA, and HPA. A molecule of the invention may be immobilized onto the surface of a sensor chip using any of the immobilization methods and chemistries known in the art, including but not limited to, direct covalent coupling via amine groups, direct covalent coupling via sulfhydryl groups, biotin attachment to avidin coated surface, aldehyde coupling to carbohydrate groups, and attachment through the histidine tag with NTA chips 5.5.1 Polynucleotides Encoding the Immunospecific Polypeptides of the Invention The present invention also includes polynucleotides that encode the immunospecific polypeptides of the invention (e.g., polypeptides comprising a rabbit $V_H$ or $V_L$ domain, comprising one or more CDRs identified by the methods of the invention, comprising amino acid scaffold sequences or amino acid scaffold residues, etc.) or other immunospecific polypeptides or fragments thereof produced by the methods of the invention, and humanized versions thereof, and methods for producing same.

The methods of the invention also encompass polynucleotides that hybridize under various stringency, e.g., high stringency, intermediate or lower stringency conditions, to polynucleotides that encode an immunospecific polypeptide of the invention. The hybridization can be performed under various conditions of stringency. By way of example and not limitation, procedures using conditions of low stringency are as follows (see also Shilo and Weinberg, 1981, Proc. Natl. Acad. Sci. U.S.A. 78, 6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10⁶ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10⁶ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 mM before autoradiography. Other conditions of high stringency which may be used are well known in the art. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, .COPYRGT. 1987-1997, Current Protocols, .COPYRGT. 1994-1997 John Wiley and Sons, Inc.; see especially, Dyson, 1991, "Immobilization of nucleic acids and hybridization analysis," In: Essential Molecular Biology: A Practical Approach, Vol. 2, T. A. Brown, ed., pp. 111-156, IRL Press at Oxford University Press, Oxford, UK) (each of which is hereby incorporated by reference herein in its entirety).

The polynucleotides may be obtained, and the nucleotide sequence of the polynucleotides determined, by any method known in the art.

A polynucleotide encoding an immunospecific polypeptide of the invention may be generated from nucleic acid from a suitable source (e.g., a cDNA library generated from, or nucleic acid, preferably poly A+ RNA, isolated from, any tissue or cells expressing the rabbit antibodies, in particular, rabbit variable domains, such as plasma cells) by hybridization with immunoglobulin specific probes and/or PCR amplification using synthetic primers hybridizable to the 3' and 5' ends of the variable domain sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the immunospecific polypeptide of the invention is determined, it may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate molecules of the invention having a different amino acid sequence, for example to create amino acid substitutions, deletions, and/or insertions.

In a specific embodiment, one or more of the rabbit CDRs identified by the methods of the invention are inserted within heterologous framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the polynucleotide generated by the combination of the framework regions and CDRs encodes an immunospecific polypeptide, e.g., antibody, that specifically binds to the antigen and/or epitope of interest. Preferably, as discussed supra, one or more amino acid substitutions may be made within the framework regions, and, preferably, the amino acid substitutions improve binding of the antibodies of the invention to said antigen and/or epitope.

In another embodiment, libraries or rabbit immunoglobulins or immunoglobulin variable domains or any other rabbit libraries available in the art, can be screened by standard techniques known in the art, to clone the nucleic acids encoding the immunospecific polypeptides of the invention.

5.5.2 Recombinant Expression of Immunospecific Polypeptides of the Invention.

Once a nucleic acid sequence encoding an molecule of the invention has been obtained, the vector for the production of the immunospecific polypeptide may be produced by recombinant DNA technology using techniques well known in the art. Methods which are well known to those skilled in the art can be used to construct expression vectors containing the coding sequences of the polypeptides of the invention and appropriate transcriptional and translational control signals. These methods include, for example, in vitro recombinant DNA techniques, synthetic techniques, and in vivo genetic recombination. (See, for example, the techniques described in Sambrook et al., 1990, Molecular Cloning, A Laboratory Manual, 2d Ed., Cold Spring Harbor Laboratory, Cold Spring Harbor, N.Y. and Ausubel et al. eds., 1998, Current Protocols in Molecular Biology, John Wiley & Sons, NY).

An expression vector comprising the nucleotide sequence of an immunospecific polypeptide of the invention can be transferred to a host cell by conventional techniques (e.g., electroporation, liposomal transfection, and calcium phosphate precipitation) and the transfected cells are then cultured by conventional techniques to produce the polypeptide of the invention. In specific embodiments, the expression of the polypeptide is regulated by a constitutive, an inducible or a tissue, specific promoter.

The host cells used to express the recombinant immunospecific polypeptides of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, Gene 45:101; Cockett et al., 1990, Bio/Technology 8:2).

A variety of host-expression vector systems may be utilized to express the immunospecific polypeptides of the invention. Such host-expression systems represent vehicles by which the coding sequences of the polypeptides may be produced and subsequently purified, but also represent cells which may, when transformed or transfected with the appropriate nucleotide coding sequences, express the polypeptides of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces Pichia*) transformed with recombinant yeast expression vectors containing polypeptide coding sequences; insect cell systems infected with recombinant virus expression vectors (e.g., baculovirus) containing the polypeptide coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing polypeptide coding sequences; or mammalian cell systems (e.g., COS, CHO, BHK, 293, 293T, 3T3 cells, lymphotic cells (see U.S. Pat. No. 5,807,715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the immunospecific polypeptide being expressed. For example, when a large quantity of such a protein is to be produced, for the generation of pharmaceutical compositions of an immunospecific polypeptide of the invention, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the immunospecific polypeptide coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The immunospecific polypeptide coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the immunospecific polypeptide coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunospecific polypeptide molecule in infected hosts. (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, W138, BT483, Hs578T, HTB2, BT20 and T47D, CRL7030 and Hs578Bst.

For long-term, high-yield production of recombinant proteins, stable expression is preferred. For example, cell lines which stably express an immunospecific polypeptide of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the immunospecific polypeptide of the invention. Such engineered cell lines may be particularly useful in screening and evaluation of compounds that interact directly or indirectly with the immunospecific polypeptide of the invention.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1992, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488-505; Wu and Wu, 1991, 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1; and hygro, which confers resistance to hygromycin (Santerre et al., 1984, Gene 30:147) (each of the above references hereby incorporated in their entireties).

The expression levels of an immunospecific polypeptide of the invention can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an immunospecific polypeptide is amplifiable, increase in the level of inhibitor present in culture of host cell will increase the number of copies of the marker gene. Since the amplified region is associated with the nucleotide sequence of the immunospecific polypeptide of the invention, production of the immunospecific polypeptide will also increase (Crouse et al., 1983, Mol. Cell. Biol. 3:257) (each of the above references hereby incorporated in their entireties).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the immunospecific polypeptide of the invention has been recombinantly expressed, it may be purified by any method known in the art for purification of an immunospecific polypeptide, for example, by chromatography (e.g., ion exchange, affinity, particularly by affinity for the specific antigen after Protein A, and sizing column chromatography), centrifugation, differential solubility, or by any other standard technique for the purification of proteins.

5.6 Prophylactic and Therapeutic Methods

Immunospecific polypeptides of the present invention that function as a prophylactic and or therapeutic agents against a disease, disorder, or infection can be administered to an animal, preferably a mammal, and most preferably a human, to treat, prevent or ameliorate one or more symptoms associated with the disease, disorder, or infection. Immunospecific polypeptides of the invention can be administered in combination with one or more other prophylactic and/or therapeutic agents useful in the treatment, prevention or management of a disease, disorder, or infection. In certain embodiments, one or more immunospecific polypeptides of the invention are administered to a mammal, preferably a human, concurrently with one or more other therapeutic agents useful for the treatment of a disease. The term "concurrently" is not limited to the administration of prophylactic or therapeutic agents at exactly the same time, but rather it is meant that immunospecific polypeptides of the invention and the other agent are administered to a subject in a sequence and within a time interval such that the immunospecific polypeptides of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route.

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of disease, the route of administration, as well as age, body weight, response, and the past medical history of the patient. Suitable regimens can be selected by one skilled in the art by considering such factors and by following, for example, dosages reported in the literature, and recommended in the Physician's Desk Reference (56$^{th}$ ed., 2002).

5.7 Compositions and Methods of Administering

The invention provides methods and pharmaceutical compositions comprising the immunospecific polypeptides of the invention. The invention also provides methods of treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or conjugated molecules of the invention. In a preferred aspect, an immunospecific polypeptide or fusion protein or conjugated molecule, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human.

Various delivery systems are known and can be used to administer a composition comprising immunospecific polypeptides of the invention, e.g., encapsulation in liposomes, microparticles, microcapsules, recombinant cells capable of expressing the immunospecific polypeptide or fusion protein, receptor-mediated endocytosis (See, e.g., Wu and Wu, 1987, J. Biol. Chem. 262:4429-4432), construction of a nucleic acid as part of a retroviral or other vector, etc.

Methods of administering an immunospecific polypeptide of the invention include, but are not limited to, parenteral administration (e.g., intradermal, intramuscular, intraperitoneal, intravenous and subcutaneous), epidural, and mucosal (e.g., intranasal and oral routes). In a specific embodiment, the immunospecific polypeptides of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The immunospecific molecules of the invention may be delivered in a sustained release formulation. The formulations provide extended release and extended half-life of administered therapeutic polypeptides. Controlled release systems suitable for use include, without limitation, diffusion-controlled, solvent-controlled and chemically-controlled systems. Diffusion controlled systems include, for example reservoir devices, in which the immunospecific molecules of the invention are enclosed within a device such that release of the molecules is controlled by permeation through a difussion barrier. Common reservoir devices include, for example, membranes, capsules, microcapsules, liposomes, and hollow fibers. Monolithic (matrix) device are a second type of diffusion controlled system, wherein the immunospecific molecules are dispersed or dissolved in an rate-controlling matrix (e.g., a polymer matrix). The immunospecific molecules of the invention are homogeneously dispersed throughout a rate-controlling matrix and the rate of release is controlled by diffusion through the matrix. Polymers suitable for use in the monolithic matrix device include naturally occurring polymers, synthetic polymers and synthetically modified natural polymers, as well as polymer derivatives.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

Generally, humanized immunospecific polypeptides, e.g., antibodies, have a longer half-life within the human body than immunospecific polypeptides, e.g., antibodies from other species due to the immune response to the foreign polypeptides. Thus, lower dosages of humanized immunospecific polypeptides, e.g., antibodies, and less frequent administration is often possible. Further, the dosage and frequency of administration of immunospecific polypeptides of the invention or fragments thereof may be reduced by enhancing uptake and tissue penetration of the antibodies by modifications such as, for example conjugation to G proteins.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an immunospecific polypeptide of the invention, care must be taken to use materials to which the immunospecific polypeptide or the fusion protein does not absorb.

Treatment of a subject with a therapeutically or prophylactically effective amount of the immunospecific polypeptides of the invention can include a single treatment or, preferably, can include a series of treatments. The pharmaceutical compositions of the invention may be administered once a day, twice a day, or three times a day. In other embodiments, the pharmaceutical compositions may be administered once a week, twice a week, once every two weeks, once a month, once every six weeks, once every two months, twice a year or once per year. It will also be appreciated that the effective dosage of the antibodies used for treatment may increase or decrease over the course of a particular treatment.

5.7.1 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of the immunospecific polypeptides of the invention and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

5.7.2 Kits

The invention provides a pharmaceutical pack or kit comprising one or more containers filled with one or more of the immunospecific polypeptides of the invention. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more immunospecific polypeptides of the invention. In another embodiment, a kit further comprises one or more other prophylactic or therapeutic agents useful for the treatment of a disease, in one or more containers. In other embodiments, the prophylactic or therapeutic agent is a biological or hormonal therapeutic.

5.8 Characterization and Demonstration of Therapeutic Utility

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary such as the temporal regime of administering the prophylactic and/or therapeutic agents, and whether such agents are administered separately or as an admixture.

Once the prophylactic and/or therapeutic agents of the invention have been tested in an animal model they can be tested in clinical trials to establish their efficacy. Establishing clinical trials will be done in accordance with common methodologies known to one skilled in the art, and the optimal dosages and routes of administration as well as toxicity profiles of the compositions of the invention can be established using routine experimentation.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

6. EXAMPLES

The following methods can be used with naïve or immunized rabbits

6.1 Isolation and Characterization of Immunospecific, Stable $V_H$ and $V_L$ Domains The following method provides for the identification and isolation of distinctive rabbit variable domains which exhibit unique properties compared to human, mouse, or camel antibodies, presenting high affinity, specificity and stability 6.1.1 Materials and Methods Rabbit Immunization (Optional)

New Zealand White rabbits were immunized with purified Vif, HIV GP41, HIV integrase, TNF-alpha, vWF, or Delta4 over the course of twelve week. The rabbits were administered four subcutaneous injections at 2-3 week intervals, of 50 µg purified protein prepared in 1 ml adjuvant according to the manufacturer's directions (Ribi Immunochem Research, Hamilton, Mont.). Five days after the final boost, spleen and bone marrow were harvested and used for total RNA preparation RNA Isolation and Library Construction Tissue Samples were harvested and prepared for total RNA isolation using TRI reagent (Molecular Research Centre) according to the manufacturer's protocol. Isolated total RNA was dissolved in 500 µl of RNase-free water and concentration and purity were determined by spectrophotometry. First strand cDNA was synthesized from total RNA using an oligo (dT) primer and reverse transcriptase (Superscript; Invitrogen) using the manufacturer's protocol.

Primary amplification of the genes coding for the variable regions of the heavy chains and light chains was performed using the sense primers presented in table 1 (5' part of the variable region; FIG. 1) and the antisense primers presented in table 2 (3' part of the constant region of the heavy and light chains; FIGS. 2A-B)

TABLE 1

Sense Primers for Isolation of Rabbit VH or VL domains From cDNA Preparation

| Domain | Primer | Sequence |
|---|---|---|
| VH | SDVH1-F | 5' GGG CCC AGG CGG CC CAG TCG GTG GAG GAG TCC TGG 3' (SEQ ID NO: 10) |
|  | SDVH2-F | 5' GGG CCC AGG CGG CC CAG TCG GTG AAG GAG TCC GAG 3' (SEQ ID NO: 11) |
|  | SDVH3-F | 5' GGG CCC AGG CGG CC CAG TCG YTG GAG GAG TCC GGG 3' (SEQ ID NO: 12) |
|  | SDVH4-F | 5' GGG CCC AGG CGG CC CAG SAG CAG CTG RTG GAG TCC GG 3' (SEQ ID NO: 13) |
| VL | SDVK1-F | 5' GGG CCC AGG CGG CC GAGC TCG TGM TGA CCC AGA CTC CA 3' (SEQ ID NO: 14) |
|  | SDVK2-F | 5' GGG CCC AGG CGG CC GAGC TCG ATM TGA CCC AGA CTG CA 3' (SEQ ID NO: 15) |
|  | SDVK3-F | 5' GGG CCC AGG CGG CC GAGC TCG TGA TGA CCC AGA CTG AA 3' (SEQ ID NO: 16) |
|  | SDVλ-F | 5' GGG CCC AGG CGG CC GAGC TCG TGC TGA CTC AGT CGC CCT C 3' (SEQ ID NO: 17) |

TABLE 2

Antisense Primers for Isolation of Rabbit VH or VL domains from cDNA Preparation

| Domain | Primer | Sequence |
|---|---|---|
| VH | SDG-R | 5' CCT GGC CGG CCT GGC CAC TAG TGA CTG AYG GAG CCT TAG GTT GCC C 3' (SEQ ID NO: 18) |
| VL | SDVKj10-R | 5' CCT GGC CGG CCT GGCC TTT GAT TTC CAC ATT GGT GCC 3' (SEQ ID NO: 19) |
|  | SDVKj0-R | 5' CCT GGC CGG CCT GGCC TAG GAT CTC CAG CTC GGT CCC 3' (SEQ ID NO: 20) |
|  | SDVK42j0-R | 5' CCT GGC CGG CCT GGCC TTT GAC SAC CAC CTC GGT CCC 3' (SEQ ID NO: 21) |
|  | SDVλ-R | 5' CCT GGC CGG CCT GGC C GCCTGTGACGGTCAGCTGGGTCCC 3' (SEQ ID NO: 22) |

The primary PCR was performed in 50 µl reaction volume using 25 µmol of each primer. 2.5 µl random primed or oligo-dT cDNA was used as template (equivalent of 5 mRNA). The reaction conditions for the primary PCR were 11 min at 94° C., followed by 30/60/120 sec at 54/55/72° C. for 30 cycles, and 5 min at 72° C. All reactions were performed with 2.5 mM MgCl2, 200 µM dNTP (Roche Diagnostics, Brussels, Belgium) and 1.25 U AmpliTaq Gold DNA polymerase (Roche).

PCR products were separated on a 1% agarose gel and the DNA eluted using the QIAquick gel extraction kit or QIAEXII (Qiagen)

All primers have the SfiI site. DNA fragments were Sfi-cut, purified, and cloned into phagemid vector. The phagemid contained a suppressor stop codon and sequences encoding peptide tags for purification ($His_6$) and detection (HA).

Library Ligation and Transformation

Approximately 50 ng of linearized vector DNA (as determined by gel electrophoresis against known amounts) were ligated with approximately a 1-3 fold excess of insert in 20 µl reactions containing 1× ligase buffer (50 mM Tris pH7.5, 5 mM MgCl$_2$, 1 mM dithioerythritol, 1 mM ATP, pH 7.5) and 1 U T4 DNA ligase (Roche), for ligation of cohesive-end ligations. Ligations were incubated 16-18 h at 12-14° C.

Results of the ligations and a corresponding number of cuvettes were incubated on ice for 10 min. Simultaneously, electrocompetent E. coli were thawed on ice. 2 µl of each ligation reaction were added to the electrocompetent bacteria, transferred to a cuvette and stored on ice for 1 min. Electroporation was performed at 2.5 kV, 25 µF, and 200Ω. Cuvettes were immediately flushed with 1 ml of SOC medium at room temperature and the cultures shaken at 250 rpm for 1 h at 37° C. or 30° C. Cultures were then spread on LB agar plates containing 100 µg/ml ampicilin, 30 µg/ml kanamycin, and 17 µg/ml chloramphenicol and incubated overnight at 37° C. or 30° C.

Phagemid vector was isolated and electorporated into host cells according to manufacturer's protocols. After electroporation, 5 ml of SOC was added and cultures were shaken for 1 h at 37° C. 10 ml of SB medium/carb was then added for 1 h at 37° C. 4.5 µl of 100 mg/ml carbenicillin was next added and cultures were shaken for another 1 h at 37° C. before adding 1 ml of VSCM13 (helper phage; 10$^{13}$ pfu/ml) to each 15 ml culture. A total of 170 ml SB medium/carb added to the cultures, which were shaken for 2 h at 37° C. 280 µl of 50 mg/ml kanamycin was added and the cultures continued shaking O/N at 37° C. On the following morning, the cultures were centrifuged and the phage supernatants precipitated by adding 25 ml of PEG-8000 (polyethylene glycol)/NaCl and incubation on ice for 30 min. Phage was centrifuged from the supernatant and pellets were resuspended in 2 ml of TBS/BSA 1%, spun down and filtered through a 0.2 µm filter into a sterile tube.

Library Panning

Immobilized antigens (Vif, Gp41, Integrase, TNF-alpha, vWF, Delta4) were used to pan the phage expression library for immunospecific binding. Antigen was bound to a microtitre plate by incubation overnight O/N at 4° C. Plates were then washed and blocked with TBS/BSA 3% for 1 h at 37° C. 500 of freshly prepared phage library was added to each well and incubated for 2 h at 37° C. Panning consisted of several rounds of binding phage to an antigen immobilized to the well of an ELISA plate, washing, elution by trypsinization (cleaves the antibody fragment off the phage surface), and reamplification. During each round, specific binding clones were selected and amplified. These clones predominated after 3 or 4 rounds.

Wells were washed with 150 µl TBS/0.5% Tween 20. Washing steps were increased from 5 in the first round to 10 in the second round and 15 in the third and fourth round. If further rounds of panning were desired, phage eluates were transferred to 2 ml E. coli cultures that had been prepared by inoculation with 2 µl of ER2537 and incubated while shaking for 2 h at 37° C. until O.D=1. The elutate exposed cultures were incubated for 15 min at RT. 6 ml of prewarmed SB medium/carb was added and shaken 1 h at 37° C. followed by the addition of 1 ml of VCSM13 (helper phage) and 91 ml of prewarmed SB medium/carb. Cultures were shaken for 2 h at 37° C., followed by the addition of 1400 of 50 mg/ml kanamycin and then shaken O/N at 37° C. Antigen coated plates were prepared as described for the next round of panning. Panning of second round was then repeated following the same protocol.

After panning, the pooled phage were tested by binding to antigen coated plates (prepared as described) and detected by HRP-conjugated anti-HA (1:2000) to assess whether it was worthwhile to continue with the analysis of single clones.

Construction of CAT-fusion Single Domain Antibody Libraries

The CAT gene was amplified from pCAT (Stratagene) by PCR and inserted into pET-derived plasmid using EcoRI and SphI restriction sites to create the pE-CAT. The 5'PCR primer originally used to clone the variable domains was also designed to contain two sequential and different SfiI cloning sites, and an amber codon (TAG) just before the beginning of the CAT gene. To clone our single-domain antibody libraries fused into the CAT gene, SDVH and SDVL fragments were generated by PCR from each p-SDVH (plasmid expressing VH domains) and pSDVL (plasmid expressing VL domains) library vectors or from phagemid vectors selected by panning. The resulting SDVH and SDVL PCR fragments were gel-purified, digested with the restriction endonuclease SfiI, and cloned independently into the appropriately SfiI cut vector pE-CAT. The pSDVH-CAT and pSDVL-CAT constructs are under the control of the strong Lac promoter that also includes an N-terminal His$_6$ affinity tag and the ampicillin resistance gene. Alternatively, SDVH or SDVL fragments may be cloned into readily available vectors designed to express cloned sequences as fusion proteins with CAT, e.g., the PCFN1 vector (see Maxwell, et al., 1999, J Prot Sci 8:1908-1911, incorporated herein by reference in its entirety; FIG. 5).

Chloramphenicol Resistance Analysis

Chloramphenicol resistance assays were performed by transforming ER2738 cells (New England Biolabs, Inc) with each single-domain CAT-fusion library. The transformation mixtures were inoculated into 5 mL of SOC and incubated at 37° C. for 1 hour. Next, 10 ml of SB medium with 3 µl of 100 mg/ml ampicillin was added to each library. A total of 15 ml of each culture was shaken for 1 hour at 37° C. Subsequently 4.5 µl of 100 mg/ml ampicillin was added and cultures shaken for one hour at 37° C. Then, 85 ml of SB medium with 85 µl of 100 mg/ml ampicillin Was added and cultures grown overnight at 37° C. The following day, 600 µl of each culture was used to inoculate 20 ml of SB medium containing 100 µg/ml of ampicillin. Expression of CAT-fusion single-domain proteins was induced by addition of 0.5 mM IPTG when the optical density of cultures reached 0.9 (at 600 nM). After 2 hours of incubation at 37° C., 100 µl aliquots of each library were plated on agar plates with IPTG (200 µg/ml) and various concentrations of chloramphenicol. Plates were incubated at 37° C. for 16-20 hours. The level of resistance was quantified as the highest level of chloramphenicol at which colonies appeared after the 37° C. incubation period.

Stability Analysis

Confirmation of the stability of clones selected by panning and/or chloramphenicol resistance assays (or combinations of both) was performed by monitoring the unfolding transition in response to heat or increasing concentration of guanidium chloride (GdmCl) by intrinsic fluorescence. Expressed and isolated clones were diluted to a concentration of 6 µM. Intrinsic fluorescence was determined at a wavelength of 280 or 295 nm, with emission spectra recoded from 310 to 440 nm. Fluorescence spectra were corrected for background fluorescence of the solution. FIG. 6A depectis the representative unfolding transition curve of a $V_L$ domain of the invention in response to increasing heat. FIG. 6B depectis the representative unfolding transition curve of a $V_L$ domain of the invention in response to increasing concentrations of GdmCl; prior to fluorescence measurement, 6 µM samples of protein were incubated overnight at 25° C. for each concentration of GdmCl.

Sequence Analysis

Vector clones selected by panning and/or chloramphenicol resistance, or combinations of both, were inoculated into culture, and the cultures were induced with 1 mM IPTG (isopropyl-β-D-thiogalactopyranoside) and tested for binding. DNA fingerprinting (analysis of different sizes of fragments after amplification by PCR), and AluI analysis (enzyme which digests DNA in several sequences) of antibody fragments encoding PCR products were performed in parallel to test for diversity among the clones. Selected clones were then subjected to DNA sequence analysis and expressed without gene III product for further analysis.

6.1.2 Results

Heavy Chain Variable Domain

Tables 3-6 present representative framework sequences of rabbit heavy chain variable domains selected by the stability assay and/or the stability assay with phage panning. Sequence analysis of selected clones relative to initial pools indicated that the following sequences provide enhanced stability and/or affinity: for the VH FR1 domain, QEQLM-ETESGGGAEGGLVKPGASLTLTCTAS (SEQ ID NO:57); for the VH FR2 domain, WVRQAPGKGLEWIG (SEQ ID NO:69); for the VH FR3 domain, YATWVNGRFTLSR-DIDQSTGCLQLNSLTAADTATYYCAR (SEQ ID NO:95); and for the VH FR4 domain, WGQGTLVTVSS (SEQ ID NO:139).

Additional point mutation studies indicated that the presence of one or more of the following amino acid residues, conferred enhanced stability and/or affinity to the $V_H$ domain: a phenylalanine at position 46 (within the FR2 domain), a glutamic acid at position 53 (within the FR2 domain), an arginine at position 54 (within the FR2 domain), a glycine at position 56 (within the FR2 domain), an alanine at position 58 (within the FR2 domain), and an arginine at position 126 (within the FR4 domain). Analysis and point mutation studies within the CDR domains also indicated that the presence of a cysteine at position 44 (the final CDR1 residue) and/or a cysteine at position 59 (the first residue in CDR2) conferred enhanced stability and/or affinity. It is believed that these cysteines act to stabilize the three-dimensional structure of the domain, Amino acid positions are according to the positions within the sequence alignments presented in FIG. 3.

TABLE 3

Amino Acid Sequences of $V_H$ FR1 domains selected by methods of the invention

| SEQ ID NO | ALIGNMENT POSITION 1-31 |
|---|---|
| 23 | QQQLV--ESGGR----LVKPDFTLTITCTVS |
| 24 | -QSVE--ESGGG----LVTPGTPLTLTCTVS |
| 25 | -QSLE--ESGGG----LVQPGGSLKVSCKAS |
| 26 | -QSLE--ESGGR----LVTPGTPLTLTCTVS |
| 27 | QQQLM--KSGGG----LVQPGGSLTLSCKAS |
| 28 | -QSLE--ESGGR----LVTPGGSLTPTCTVS |
| 29 | -QSVE--ESGGR----LVKPDETLTLTCTVS |
| 30 | -QSVE--ESRGR----LVTPGTPLTLTCTVS |
| 31 | QEQLV--ESGGG----LVQPGGSLKLSCKAS |

TABLE 3-continued

Amino Acid Sequences of $V_H$ FR1 domains selected by methods of the invention

| SEQ ID NO | ALIGNMENT POSITION 1-31 |
|---|---|
| 32 | QQQLV--ESGGG----LVQPGGSLKLSCKAS |
| 33 | -QSMK--ESEGR----LVTPGGSLTLTCTVS |
| 34 | -QSVE--ESRGR----LVTPGGSLTLTCTVS |
| 35 | -QSVE--ESGGG----LVQPGGSLKVSCKAP |
| 36 | -QSLE--ESGGR----LVTPGGSLTLTCTVS |
| 37 | -QSVE--ESGGR----LVTPGGSLTLTCTVS |
| 38 | QEQLM--ESGGG----LVQPGGSLTLSCKAS |
| 39 | -QSLE--ESGGR----LVTPGTPLTLTCTAS |
| 40 | QQQLV--ESGGG----LVQPGGSLTLSCKAS |
| 41 | -QSVE--ESGGR----LVTPGTPLTLTCTVS |
| 42 | -QSVE--ESRGG----LVQPGGSLKVSCKAS |
| 43 | -QSVE--ESRGG----LFKPTDTLTLTCTVS |
| 44 | -QSVE--ESGGR----LISPGGSLTLTCTVS |
| 45 | -QSLE--ESGGR----LVKPDETLTLTCTVS |
| 46 | -QSvE--ESRGR----LVTPGTPLTLTCTAS |
| 47 | -QSVE--ESRGR----LVKPDETLTLTCTVS |
| 48 | -QSVE--ESRGD----LVKPEGSLTLTCTAS |
| 49 | -QSLE--ESGGR----LVTPGTPLTLTCTIS |
| 50 | -QSLE--ESGGR----LVTLGTPLTLTCTVS |
| 51 | -QSLE--ESWGR----LVKPDETLTITCTVS |
| 52 | -QSVE--ESGGG----LVQPGGSLKLSCKAS |
| 53 | QEQLV--ESGGG----LVKPEGSLTLTCKAS |
| 54 | -QSVE--ESGGN----LVTPGTPLTLTCTVS |
| 55 | QQQLM--ESGGG----LVQPGGSLKLSCKAS |
| 56 | QEQLMETESGGGAEGGLVKPGGSLELCCKAS |
| 57 | QEQLMETESGGGAEGGLVKPGASLTLTCTAS |
| 58 | --QSLE-ESGGR----LVTPGTPLTLTCTVS |
| 59 | --QSVE-ESRGD----LVKPGASLTLTCTAS |
| 60 | --QSVE-ESGGR----LITPGGSLTLTCTAS |
| 61 | --QSLE-ESGGD----LVKPGASLTLTCTAS |
| 62 | --QSVE-ESRGR----LVTPGTPLTLTCTVS |
| 63 | QEQLMETESGGG----LVKPGASLTLTCTAS |
| 64 | --QSLE-ESGGD----LVQPGASLTLTCTAS |
| 65 | -QQQLV-ESGGD----LVKPEGSLTLTCTAS |
| 66 | --QSLE-ESGGD----LVKPEGSLTLTCTAS |

TABLE 4

Amino Acid Sequences of V$_H$ FR2 domains selected by methods of the invention

| SEQ ID NO | ALIGNMENT POSITION 45-58 |
|---|---|
| 67 | WVRQAPGEGLEWIG |
| 68 | WVRQAPGKGLQYIG |
| 69 | WVRQAPGKGLEWIG |
| 70 | WVRQAPGKGLDWIG |
| 71 | WVRQAPGEGLDWIG |
| 72 | WVRQAPGKGLEYIG |
| 73 | WGRQAPREGLEWIG |
| 74 | WVRQAPGKRLEWIG |
| 75 | WVRQAPGKGLEWVA |
| 76 | WVRQAPEKGLEWIG |
| 77 | WVRQAPGKGLEWIA |
| 78 | WFRQAPGKGLEWIA |
| 79 | WFRQAPGKGLEWIG |
| 80 | WFRQAPGKELEWIG |
| 81 | WFRQAPGLGREWIG |
| 82 | WFRQAPGLGLEGIG |
| 83 | WVRQAPGKELEWIG |
| 84 | WVRQAPGKEREWIG |
| 85 | WVRQAPGKELEGIG |
| 86 | WVRQAPGKGREWIG |
| 87 | WVRQAPGKGREGIG |
| 88 | WVRQAPGKGLEGIG |
| 89 | WFRQAPGKEREWIG |
| 90 | WFRQAPGKELEGIG |
| 91 | WFRQAPGKGREGIG |
| 92 | WVRQAPGKEREGIG |
| 93 | WFRQAPGKEREGIG |

TABLE 5

Amino Acid Sequences of V$_H$ FR3 domains selected by methods of the invention

| SEQ ID NO | ALIGNMENT POSITION 70-110 |
|---|---|
| 94 | YASWAKGRFTIS-KTSSTTVDLKITSP--TTEDTATYFCAR |
| 95 | YATWVNGRFTLSRDIDQSTGCLQLNSL--TAADTATYYCAR |
| 96 | YATWAKGRFTIS-KTS-TTVNLQMETTSLTTEDTATFFCAR |
| 97 | YATWAKGRFTIS-KTSSTTVTLQMETTSLTAADTATYFCAR |
| 98 | YASWAKGRFTIS-KTS-TTVDLKITSP--TTEDTATYFCAS |
| 99 | YASWAEGRFSIS-KASSTTVTLQMETTSLTAADTATYFCAR |
| 100 | YANWAKGRFTIS-KTS-TTVDLKITSP--TTEDTATYFCVR |
| 101 | YASWPQGRFTIS-VTSSTTVTLQNETTSLTAADTATYFCAK |
| 102 | YASWAKGRFTIS-QTS-TTVDLKITSP--TTEDTATYFCAR |
| 103 | YATWAKGRFTIS-KPSSTTVTLQMETTSLTAADTATYFCAR |
| 104 | YANWAKGRFTIA-KTSSTTVTLQMETTSLTAADTATYFCAR |
| 105 | YASWAKGRFTIS-KTS-TTVDLKITSP--TTEDTATYFCAR |
| 106 | YPSWVDGRFTIS-KTS-TTVDLKITSP--TTEDTATYFCAR |
| 107 | YADWVTGRFTISSHNAQNTLYLQLNSL--TAADTATYFCAR |
| 108 | YANWAKGRCTIS-KTS-TTVDLKITSP--TTEDTATYFCAP |
| 109 | YATWVNGRLTISSHNAQNTLYLQLNSL--TAADTATYFCAR |
| 110 | YANWAKGRFTIS-KTP-TTVDLKINSP--TTEDTATYFCAR |
| 111 | YADWAKGRFTIS-KTS-TTVDLKITSP--TTEDTATYFCAR |
| 112 | YADWAKGRFTIS-KTS-TTMDLKITSP--TTEDTATYFCGR |
| 113 | YASWVNGRFTISSRNAQNTLYLQLNSL--TAADTATYFCAR |
| 114 | YASWVNGRFTISSDNAQNTVDLQLNSL--TAADTATYFCAR |
| 115 | YANWAKGRFTSS-KTS-TTVDLKITSP--TTEDTATYFCAR |
| 116 | YANWAKGRFTIS-KTS-TTVDLEIASP--TTEDTATYFCVR |
| 117 | YASWAEGRFTIS-KASSTTVDLKMTSL--TTEDTATYFCAR |
| 118 | YANWAKGRFTIS-RTS-TTVDLKMTSL--TTEDTATYFCAR |
| 119 | YASWAKGRFTIS-KTSSTTVDLEMTSL--TTEDTATYFCAR |
| 120 | YANWAKGRFTIS-KASSTTVELKMTGL--TTEDTATYFCAR |
| 121 | YASWVNGRFTISSHNAQNTLYLQLNSL--TAADTATYFCAR |
| 122 | YANWARGRFTIS-RTS-TTVDLEITSP--TTEDTATYFCGR |

TABLE 5-continued

Amino Acid Sequences of $V_H$ FR3 domains selected by methods of the invention

| SEQ ID NO | ALIGNMENT POSITION 70-110 |
|---|---|
| 123 | YASWVNGRFTISRTS--TTVDLKMTSL--TTEDTATYFCIR |
| 124 | YARWAKDRVTISKTS--TTVDLKITSP--TTEDTATYFCAR |
| 125 | YANWAKGRFTISKTS--TTVDLEIISP--TKEDTATYFCAT |
| 126 | YANWAKGRFTISKAS--TTVDLKITSP--TTEDTATYFCVR |
| 127 | YANWARGRFTISKTS--TTVDLKMTSP--TTEDTAIYFCAR |
| 128 | YATWAKGRFTISKTS--TTVDLKVTSP--TTEDTATYFCAS |
| 129 | YPSWAEGRFTISKTS--TTVDLKIASP--ATEDTATYFCAR |
| 130 | YASWAKGRFTISRTS--TTADLRITSP--TIEDTATYFCAR |
| 131 | YANWAKGRFTISKTS--TTVDLKMTSL--TAADTATYFCAR |
| 132 | YATWAKGRFTTSKTSS-TTVDLKMTSL--TTEDTATYFCTR |
| 133 | YANWAKGRFTIS-RTS-TTVDLKMTSP--TTEDTATYFCIR |
| 134 | YASWAEGRFTIS-RTS-TTVDLKMTSP--TTEDTATYFCAR |
| 135 | YASWAKGPFTIS-KTS-TTVDLKMTSP--TTEDMATYFCAR |
| 136 | YASWAKGRFTIS-KTS-TTVDLKTTSP--ITEDTATYFCIR |
| 137 | YASWVNGRFTISSDNAQNTVDLQMNSL--TAADTATYFCAR |
| 138 | YANWVNGRFTISLDNAQNTVFLQMTSL--TAADTATYFCAR |

TABLE 6

Amino Acid Sequences of $V_H$ FR4 domains selected by methods of the invention

| SEQ ID NO | ALIGNMENT POSITION 126-136 |
|---|---|
| 139 | WGQGTLVTVSS |
| 140 | WGPGTLVTVSS |
| 141 | WGQGILVTVSS |
| 142 | WGQGALVTVSS |
| 143 | WGPGTLVTISS |
| 144 | WGQGTLVTASS |
| 145 | WGPGTLVAVSS |
| 146 | WGQGTRVTVSS |
| 147 | WGPGTLVTGSS |

TABLE 6-continued

Amino Acid Sequences of $V_H$ FR4 domains selected by methods of the invention

| SEQ ID NO | ALIGNMENT POSITION 126-136 |
|---|---|
| 148 | WGQGSLVTISS |
| 149 | RGQGSLVTISS |

Light Chain Variable Domain

Tables 7-10 present representative sequences of rabbit light chain variable framework domains selected by stability assay and phage panning. Sequence analysis of selected clones relative to initial pools indicated that the following sequences provide enhanced stability and/or affinity, for the VL FR1 domain, ELVLTQTPPSLSASVGETVRIRC (SEQ ID NO:150) or ELVLTQTPSSVSAAVGGTVTINC (SEQ ID NO:155); for the VL FR2 domain, WYQQKPEKPPTLLIS (SEQ ID NO:174) or WYQQKPGQRPKLLIY(SEQ ID NO:181); for the VL FR3 domain, GVPPRFSGSGSGT-DYTLTIGGVQAEDVATYYC (SEQ ID NO:183) or GVSS-RFKGSGSGTQFTLTISGVQCADAATYYC (SEQ ID NO:205); and for the VL FR4 domain, FGAGTNVEIK (SEQ ID NO:206) or FAFGGGTELEIL (SEQ ID NO:210).

Additional point mutation studies indicated that the presence of a phenylalanine at position 39 (within the FR2 domain) and/or the presence of a lysine at position 42 (within the FR2 domain) and/or the presence of a cysteine at position 91 (the final FR3 residue) conferred enhanced stability and/or affinity to the $V_L$ domain. Amino acid positions are according to the positions within the sequence alignments presented in FIG. 4.

TABLE 7

Amino Acid Sequences of $V_L$ FR1 domains selected by methods of the invention

| SEQ ID NO | ALIGNMENT POSITION 1-23 |
|---|---|
| 150 | ELVLTQTPPSLSASVGETVRIRC |
| 151 | ELDMTQTPASVSEPVGGTVTIKC |
| 152 | ELVLTQTPSPVSAAVGGTVTIKC |
| 153 | ELDLTQTPASVSEPVGGTVTIKC |
| 154 | ELVLTQTPSSASEPVGGTATIKC |
| 155 | ELVLTQTPSSVSAAVGGTVTINC |
| 156 | ELDMTQTPASVSAAVGGTVTINC |
| 157 | ELDLTQTPASVEVAVGGTVTINC |
| 158 | ELDMTQTPSSVSAAVGGTVTINC |
| 159 | ELVMTQTPASVSAAVGGTVTINC |
| 160 | ELVMTQTPASVEAAVGDSVTINC |
| 161 | ELVLTQTPASVSEPVGGTVTIKC |
| 162 | ELVLTQTPSPVSAAVGGTVTISC |
| 163 | ELVMTQTESPVSAPVGGTVTIKC |
| 164 | ELVLTQTPSSKSVPVGETVTINC |
| 165 | ELDMTQTPSSKSVPVRGTVSISC |
| 166 | ELVLTQSPSSKSVPVGDTVTINC |

TABLE 7-continued

Amino Acid Sequences of $V_L$ FR1 domains selected by methods of the invention

| SEQ ID NO | ALIGNMENT POSITION 1-23 |
|---|---|
| 167 | ELDLTQTPPSLSASVGETVRIRC |
| 168 | ELDLTQTPASVEAAVGGTVTIKC |
| 169 | ELVMTQTPSPVSAAVGGTVTISC |
| 170 | ELVLTQTPSSKSVPVGDTVIINC |
| 171 | ELVLTQSPS-VSGAVGGTVIINC |
| 172 | ELVLTQTPSSVEAAVGGTVTIKC |
| 173 | ELVLTQTPASVEAAVGGTVTIKC |

TABLE 8

Amino Acid Sequences of $V_L$ FR2 domains selected by methods of the invention

| SEQ ID NO | ALIGNMENT POSITION 38-52 |
|---|---|
| 174 | WYQQKPEKPPTLLIS |
| 175 | WYQQKPGQPPKLLIY |
| 176 | WYQQKPGQPPKRLIY |
| 177 | WYQLKPGQPPKLLIY |
| 178 | WYQQKPGQPPKPLIY |
| 179 | WFQQKPGQPPKLLIY |
| 180 | WYQQKPGKPPTLLIS |
| 181 | WYQQKPGQRPKLLIY |
| 182 | WYQQKAGKPPTLLIY |

TABLE 9

Amino Acid Sequences of $V_L$ FR3 domains selected by methods of the invention

| SEQ ID NO | ALIGNMENT POSITION 60-91 |
|---|---|
| 183 | GVPPRFSGSGSGTDYTLTIGGVQAEDVATYYC |
| 184 | GVSSRFKGSGSGTEFTLTISGVQCDDAATYYC |
| 185 | GVSSRFKGSRSGTEYTLTISDLECADAATYYC |
| 186 | GVSSRFKGSGSGTEFTLTISDVQCDDAATYYC |

TABLE 9-continued

Amino Acid Sequences of $V_L$ FR3 domains selected by methods of the invention

| SEQ ID NO | ALIGNMENT POSITION 60-91 |
|---|---|
| 187 | GVPSRFKGSGSGTEFTLTISDLECADAATYYC |
| 188 | GVPSRFRGSGSGTEFTLTISGMKAEDAATYYC |
| 189 | GVSSRFKGSGSGTQFTLTISDLECDDAATYYC |
| 190 | GVPSRFKGSGSGTEYTLTISGVECDDAATYYC |
| 191 | GVPPRFSGSGAGTQFTLTISDLECDDAATYYC |
| 192 | GVPSRFKGSGSGAQFTLTISDLECDDAATYYC |
| 193 | GVPSRFKGSGSGTQFTLTISDLECDDAATYYC |
| 194 | GVPSRFKGSGSGTEFTLTISGVQCDDAATYFC |
| 195 | GVPSRFKGSGSGTQFTLTISDVVCDDAATYYC |
| 196 | GVPSRFKGSGSGTDFTLTISSVECDDAATYYC |
| 197 | GVPSRFSGSGSGTQFTLTISDLECDDAATYYC |
| 198 | GVPPRFSGSGSGADYTLTIGGVQAEDAATYYC |
| 199 | GVPSRFKGSGSGTQFTLTISDVQCDDAATYYC |
| 200 | GVSSRFKGSGSGTQFTLTINDLECDDAATYYC |
| 201 | GVPSRFKGSGSGTQFTLTISDVVCDDAATYGC |
| 202 | GVPSRFKGSGSGTQFTLTISGVQCDDAATYYC |
| 203 | GVPSRFSGSGSGTEFTLTINDLDCDDAATYYC |
| 204 | GVPSRFKGSGSGTQFTLTISDLECADAATYYC |
| 205 | GVSSRFKGSGSGTQFTLTISGVQCADAATYYC |

TABLE 10

Amino Acid Sequences of VL FR4 domains selected by methods of the invention

| SEQ ID NO | ALIGNMENT POSITION 106-116B |
|---|---|
| 206 | F--GAGTNVEIK- |
| 207 | F--GGGTEVVVK- |
| 208 | F--GGGTELEIL- |
| 209 | F--GGGTQLTVTG |
| 210 | FAFGGGTELEIL- |

The invention claimed is:

1. A method for obtaining a DNA sequence encoding a rabbit $V_L$ or $V_H$ domain that immunospecifically binds to an antigen and that exhibits thermal or chemical stability, said method comprising:

a) selecting from a phage expression library a first set of DNA sequences that encode $V_H$ or $V_L$ domains that immunospecifically bind to said antigen, said phage expression library prepared from DNA sequences that encode $V_H$ or $V_L$ domains and that were obtained from a biological sample of a rabbit containing cells that express immunoglobulins; and b) expressing said first set of DNA sequences, or a subset thereof, in bacteria as a fusion protein with CAT, selecting bacteria showing greater resistance to chloramphenicol over a range of 0.1 mM to 20 mM chloramphenicol, at 37° C., due to CAT expression, and obtaining a second set of DNA sequences encoding amino acid sequences corresponding to rabbit $V_H$ or $V_L$ domains from the selected bacteria, said second set being a subset of said first set or of the subset thereof and encoding amino acid sequences exhibiting greater thermal or chemical stability than amino acid sequences encoded by DNA sequences of said first set, or the subset thereof, that were not selected in said second set;

wherein said second set provides said DNA sequence encoding said rabbit $V_L$ or $V_H$ domain that immunospecifically binds to said antigen and that exhibits greater thermal or chemical stability than rabbit $V_H$ or $V_L$ domains encoded by DNA sequences of said first set, or the subset thereof, not selected in said second set; and wherein said rabbit $V_L$ domain comprises at least one selected from the group consisting of a $V_L$ FR1 domain having the amino acid sequence ELVLTQTPPSLSASVGETVRIRC (SEQ ID NO: 150); a $V_L$ FR1 domain having the amino acid sequence ELVLTQTPSSVSAAVGGTVTINC (SEQ ID NO: 155); a $V_L$ FR2 domain having the amino acid sequence WYQQKPEKPPTLLIS (SEQ ID NO: 174);

a V_FR2 domain having the amino acid sequence WYQQKPGQRPKLLIY (SEQ ID NO: 181); a $V_L$ FR3 domain having the amino acid sequence GVPPRFSGSGSGTDYTLTIGGVQAEDVATYYC (SEQ ID NO: 183); a $V_L$ FR3 domain having the amino acid sequence GVSSRFKGSGSGTQFTLTISGVQCADAATYYC (SEQ ID NO: 205); a $V_L$ FR4 domain having the amino acid sequence FAFGGGTELEIL (SEQ ID NO:210); and a $V_L$ FR4 domain having the amino acid sequence FGAGTNVEIK (SEQ ID NO: 206); or wherein said rabbit $V_H$ domain comprises at least one selected from the group consisting of a $V_H$ FR1 domain having the amino acid sequence QEQLMETESGGGAEGGLVKPGASLTLTCTAS (SEQ ID NO: 57); a $V_H$ FR2 domain having the amino acid sequence WVRQAPGKGLEWIG (SEQ ID NO: 69); a $V_H$ FR3 domain having the amino acid sequence YATWVNGRFTLSRDIDQSTGCLQLNSLTAADTATYYCAR (SEQ ID NO: 95); and a $V_H$ FR4 domain having the amino acid sequence WGQGTLVTVSS (SEQ ID NO: 139).

2. The method of claim 1, wherein obtaining said DNA sequence, encoding said rabbit $V_H$ or $V_L$ domain that immunospecifically binds to said antigen, further comprises DNA sequence analysis of DNA sequences of said selected bacteria of step (b).

3. A method for obtaining a DNA sequence encoding a rabbit $V_L$ or $V_H$ domain that immunospecifically binds to an antigen and that exhibits thermal or chemical stability, said method comprising:

a) expressing a first set of sequences of DNA that encode $V_H$ or $V_L$ domains in bacteria as a fusion protein with CAT, wherein said DNA sequences were obtained from a biological sample of a rabbit containing cells that express immunoglobulins;

b) selecting bacteria showing greater resistance to chloramphenicol over a range of 0.1 mM to 20 mM chloramphenicol, at 37° C., due to CAT expression, and obtaining a second set of DNA sequences encoding amino acid sequences corresponding to rabbit $V_H$ or $V_L$ domains from the selected bacteria, said second set being a subset of said first set and encoding amino acid sequences exhibiting greater thermal or chemical stability than amino acid sequences encoded by DNA sequences of said first set not selected in said second set; and c) selecting from a phage expression library a third set of DNA sequences that encode $V_H$ or $V_L$ domains that immunospecifically bind to said antigen, wherein said library is prepared from said second set of DNA sequences, or a subset thereof; said third set being a subset of said second set or of the subset thereof;

wherein said third set provides said DNA sequence encoding said rabbit $V_L$ or $V_H$ domain that immunospecifically binds to said antigen and that exhibits greater thermal or chemical stability than rabbit $V_H$ or $V_L$ domains encoded by DNA sequences of said first set not selected in said second set and wherein said rabbit $V_L$ domain comprises at least one selected from the group consisting of a $V_L$ FR1 domain having the amino acid sequence ELVLTQTPPSLSASVGETVRIRC (SEQ ID NO: 150); a $V_L$ FR1 domain having the amino acid sequence ELVLTQTPSSVSAAVGGTVTINC (SEQ ID NO: 155); a $V_L$ FR2 domain having the amino acid sequence WYQQKPEKPPTLLIS (SEQ ID NO: 174); a $V_T$ FR2 domain having the amino acid sequence WYQQKPGQRPKLLIY (SEQ ID NO: 181); a $V_L$ FR3 domain having the amino acid sequence GVPPRFSGSGSGTDYTLTIGGVQAEDVATYYC (SEQ ID NO: 183); a $V_L$ FR3 domain having the amino acid sequence GVSSRFKGSGSGTQFTLTISGVQCADAATYYC (SEQ ID NO: 205); a $V_L$ FR4 domain having the amino acid sequence FAFGGGTELEIL (SEQ ID NO:210); and a $V_L$ FR4 domain having the amino acid sequence FGAGTNVEIK (SEQ ID NO: 206); or wherein said rabbit $V_{HS}$ domain comprises at least one selected from the group consisting of a $V_H$ FR1 domain having the amino acid sequence QEQLMETESGGGAEGGLVKPGASLTLTCTAS (SEQ ID NO: 57); a $V_H$ FR2 domain having the amino acid sequence WVRQAPGKGLEWIG (SEQ ID NO: 69); a $V_H$ FR3 domain having the amino acid sequence YATWVNGRFTLSRDIDQSTGCLQLNSLTAADTATYYCAR (SEQ ID NO: 95); and a $V_H$ FR4 domain having the amino acid sequence WGQGTLVTVSS (SEQ ID NO: 139).

4. The method of claim 3, wherein obtaining said DNA sequence, encoding said rabbit $V_H$ or $V_L$ domain that immunospecifically binds to said antigen, further comprises DNA sequence analysis of DNA sequences selected from said phage expression library of step (c).

5. The method of claim 1 or 3, wherein said rabbit biological sample is from a rabbit that has been immunized with said antigen.

6. The method of claim 1 or 3, wherein, step a) is repeated one or more times or step c) is repeated one or more times.

7. The method of claim 1 or 3 wherein said biological sample comprises plasma cells, lymphoid tissue, spleen tissue, lymph node tissue, bone marrow tissue, or appendix tissue.

8. The method of claim 1 or 3 wherein said antigen is not immunogenic in mice or rats.

9. The method of claim 1 or 3, wherein said recombinant $V_H$ or $V_L$ domain exhibits a Kd for said antigen greater than 0.001 nM but no greater than 50 nM.

10. The method of claim 9, wherein the recombinant $V_H$ or $V_L$ domain exhibits a Kd for said antigen greater than 0.001 nM but no greater than 20 nM.

11. The method of claim 1 or 3, wherein said chloramphenicol concentration is 2.0 mM at 37° C. and said bacteria is *E. coli*.

12. The method of claim 1 or 3, wherein said chloramphenicol concentration is 2.5 mM at 37° C. and said bacteria is *E. coli*.

13. The method of claim 1 or 3, wherein said chloramphenicol concentration is 3.0 mM at 37° C. and said bacteria is *E. coli*.

14. The method of claim 1 or 3, wherein said chloramphenicol concentration is 5.0 mM at 37° C. and said bacteria is *E. coli*.

15. The method of claim 1 or 3, wherein said chloramphenicol concentration is 10.0 mM at 37° C. and said bacteria is *E. coli*.

16. The method of claim 1 or 3, wherein said chloramphenicol concentration is 15.0 mM at 37° C. and said bacteria is *E. coli*.

17. The method of claim 1 or 3, wherein said chloramphenicol concentration is 20.0 mM at 37° C. and said bacteria is *E. coli*.

18. The method of claim 1 or 3, wherein said chloramphenicol concentration is 1.8 mM at 37° C. and said bacteria is *E. coli*.

* * * * *

SEQUENCE LISTING

<160> NUMBER OF SEQ ID NOS: 210

<210> SEQ ID NO 1
<211> LENGTH: 120
<212> TYPE: PRT
<213> ORGANISM: Oryctolagus

<400> SEQUENCE: 1

Gln Gln Gln Leu Val Glu Ser Gly Gly Arg Leu Val Lys Pro Asp Glu
1               5                   10                  15

Thr Leu Thr Ile Thr Cys Thr Val Ser Gly Ile Asp Leu Ser Ser Asn
            20                  25                  30

Ala Met Asn Trp Val Arg Gln Ala Pro Gly Glu Gly Leu Glu Trp Ile
            35                  40                  45

Gly Thr Ile Ser Thr Gly Gly Ser Thr Tyr Tyr Ala Ser Trp Ala Lys
50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Ala
            85                  90                  95

Leu Tyr Ala Gly Ser Thr Thr Gly Ser Pro Phe Asn Leu Trp Gly Gln
            100                 105                 110

Gly Thr Leu Val Thr Val Ser Ser
            115                 120

<210> SEQ ID NO 2
<211> LENGTH: 120
<212> TYPE: PRT
<213> ORGANISM: Oryctolagus

<400> SEQUENCE: 2

Gln Ser Val Glu Glu Ser Arg Gly Arg Leu Val Thr Pro Gly Thr Pro
1               5                   10                  15

Leu Thr Leu Thr Cys Thr Ala Ser Gly Phe Ser Leu Asn Ser Gly Tyr
            20                  25                  30

Met Glu Thr Ile Trp Val Arg Gln Ala Pro Gly Lys Gly Leu Glu Tyr
            35                  40                  45

Ile Gly Ile Ile Tyr Thr Gly Asp Ser Ala Ser Tyr Ala Ser Trp Ala
50                  55                  60

Lys Gly Arg Phe Thr Ile Ser Lys Thr Ser Ser Thr Thr Val Asp Leu
65                  70                  75                  80

Lys Ile Thr Ser Pro Thr Thr Glu Asp Thr Ala Thr Tyr Phe Cys Ala
            85                  90                  95

Arg Arg Gly Tyr Asn Ser Gly Trp Gly Ala Glu Asn Leu Trp Gly Gln
            100                 105                 110

Gly Thr Leu Val Thr Val Ser Ser
            115                 120

<210> SEQ ID NO 3
<211> LENGTH: 126
<212> TYPE: PRT
<213> ORGANISM: Oryctolagus

<400> SEQUENCE: 3

Gln Glu Gln Leu Met Glu Thr Glu Ser Gly Gly Ala Glu Gly Gly
1               5                   10                  15

Leu Val Lys Pro Gly Gly Ser Leu Glu Leu Cys Cys Lys Ala Ser Gly
            20                  25                  30

Phe Ser Leu Ser Ile Asn Tyr Trp Ile Cys Trp Val Arg Gln Ala Pro
            35                  40                  45

Gly Lys Gly Leu Glu Trp Ile Gly Cys Val Tyr Thr Asp Asp Gly Ser
50                  55                  60

Thr Tyr Tyr Ala Thr Trp Val Asn Gly Arg Phe Thr Leu Ser Arg Asp
65                  70                  75                  80

Ile Asp Gln Ser Thr Gly Cys Leu Gln Leu Asn Ser Leu Thr Ala Ala
            85                  90                  95

```
Asp Thr Ala Thr Tyr Tyr Cys Ala Arg Lys Glu Tyr Val Tyr Ser Thr
                100                 105                 110

Tyr Asn Phe Trp Gly Gln Gly Thr Leu Val Thr Val Ser Ser
            115                 120                 125

<210> SEQ ID NO 4
<211> LENGTH: 124
<212> TYPE: PRT
<213> ORGANISM: Oryctolagus

<400> SEQUENCE: 4

Gln Glu Gln Leu Val Glu Ser Gly Gly Gly Leu Val Lys Pro Glu Gly
1               5                   10                  15

Ser Leu Thr Leu Thr Cys Lys Ala Ser Gly Ile Asp Phe Ser Asn Tyr
            20                  25                  30

Gly Ile Ser Trp Val Arg Gln Ala Pro Gly Lys Gly Leu Glu Trp Val
        35                  40                  45

Ala Tyr Ile Tyr Pro Asp Tyr Gly Thr Thr Asp Tyr Ala Asn Trp Val
    50                  55                  60

Asn Gly Arg Phe Thr Ile Ser Leu Asp Asn Ala Gln Asn Thr Val Phe
65                  70                  75                  80

Leu Gln Met Thr Ser Leu Thr Ala Ala Asp Thr Ala Thr Tyr Phe Cys
                85                  90                  95

Ala Arg Asp Gly Gly Tyr Asp Asp Tyr Asn Asp Trp Gly Tyr Phe Asn
                100                 105                 110

Leu Trp Gly Pro Gly Thr Leu Val Thr Val Ser Ser
            115                 120

<210> SEQ ID NO 5
<211> LENGTH: 123
<212> TYPE: PRT
<213> ORGANISM: Oryctolagus

<400> SEQUENCE: 5

Gln Ser Leu Glu Glu Ser Gly Gly Gly Leu Val Gln Pro Glu Gly Ser
1               5                   10                  15

Leu Thr Leu Thr Cys Thr Ala Ser Gly Phe Thr Ile Ser Asn Ser Tyr
            20                  25                  30

Tyr Met Glu Thr Cys Trp Val Arg Gln Ala Pro Gly Lys Gly Leu Glu
        35                  40                  45

Trp Ile Gly Cys Ile Tyr Ala Gly Ser Ser Gly Ile Gly Tyr Tyr Ala
    50                  55                  60

Ser Trp Ala Glu Gly Arg Phe Ser Ile Ser Lys Ala Ser Ser Thr Thr
65                  70                  75                  80

Val Thr Leu Gln Met Glu Thr Ser Leu Thr Ala Ala Asp Thr Ala
                85                  90                  95

Thr Tyr Phe Cys Ala Arg Pro Val Gly Tyr Gly Gly Phe Trp Asp Leu
                100                 105                 110

Trp Gly Pro Gly Thr Leu Val Thr Val Ser Ser
            115                 120

<210> SEQ ID NO 6
<211> LENGTH: 107
<212> TYPE: PRT
<213> ORGANISM: Oryctolagus
```

```
<400> SEQUENCE: 6

Glu Leu Val Leu Thr Gln Thr Pro Ser Leu Ser Ala Ser Val Gly
1               5                   10                  15

Glu Thr Val Arg Ile Arg Cys Leu Ala Ser Glu Asp Ile Tyr Ser Gly
                20                  25                  30

Ile Ser Trp Tyr Gln Gln Lys Pro Glu Lys Pro Pro Thr Leu Leu Ile
            35                  40                  45

Ser Gly Ala Ser Asn Leu Glu Ala Gly Val Pro Pro Arg Phe Ser Gly
        50                  55                  60

Ser Gly Ser Gly Thr Asp Tyr Thr Leu Thr Ile Gly Gly Val Gln Ala
65                  70                  75                  80

Glu Asp Val Ala Thr Tyr Tyr Cys Leu Gly Ser Tyr Ser Gly Ser Ala
                85                  90                  95

Asp Phe Gly Ala Gly Thr Asn Val Glu Ile Lys
            100                 105

<210> SEQ ID NO 7
<211> LENGTH: 114
<212> TYPE: PRT
<213> ORGANISM: Oryctolagus

<400> SEQUENCE: 7

Glu Leu Val Leu Thr Gln Ser Pro Ser Ser Lys Ser Val Pro Val Gly
1               5                   10                  15

Asp Thr Val Thr Ile Asn Cys Gln Ala Ser Glu Ser Val Ala Gly Gly
                20                  25                  30

Asn Arg Leu Ser Trp Tyr Gln Gln Lys Pro Gly Gln Pro Pro Lys Leu
            35                  40                  45

Leu Ile Tyr Arg Ala Ser Asn Leu Ala Ser Gly Val Pro Ser Arg Phe
        50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Gly Tyr Asp Cys
                85                  90                  95

Ser Ser Ala Asp Cys Ser Ala Phe Gly Gly Gly Thr Gln Leu Thr Val
            100                 105                 110

Thr Gly

<210> SEQ ID NO 8
<211> LENGTH: 109
<212> TYPE: PRT
<213> ORGANISM: Oryctolagus

<400> SEQUENCE: 8

Glu Leu Val Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Asn Asn
                20                  25                  30

Asn Gln Leu Ser Trp Phe Gln Gln Lys Pro Gly Gln Pro Pro Lys Leu
            35                  40                  45

Leu Ile Tyr Glu Ala Ser Lys Leu Ala Ser Gly Val Pro Ser Arg Phe
        50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Ala Tyr Ser His
                85                  90                  95
```

Val His Ala Phe Gly Gly Gly Thr Glu Leu Glu Ile Leu
            100                 105

<210> SEQ ID NO 9
<211> LENGTH: 109
<212> TYPE: PRT
<213> ORGANISM: Oryctolagus

<400> SEQUENCE: 9

Glu Leu Val Leu Thr Gln Ser Pro Ser Val Ser Ala Val Gly Gly
1               5                   10                  15

Thr Val Ile Ile Asn Cys Gln Thr Ser Glu Ser Ile Ser Asn Trp Leu
            20                  25                  30

Ala Trp Tyr Gln Gln Lys Pro Gly Gln Pro Pro Lys Leu Leu Ile Tyr
        35                  40                  45

Asp Ala Ser Lys Leu Ala Ser Gly Val Pro Ser Arg Phe Lys Gly Ser
    50                  55                  60

Gly Ser Gly Thr Gln Phe Thr Leu Thr Ile Ser Gly Val Gln Cys Asp
65                  70                  75                  80

Asp Ala Ala Thr Tyr Tyr Cys Gln Gly Gly Tyr Ser Gly Ala Thr Asn
                85                  90                  95

Asn Ala Phe Gly Gly Gly Thr Gln Leu Thr Val Thr Gly
            100                 105

<210> SEQ ID NO 10
<211> LENGTH: 35
<212> TYPE: DNA
<213> ORGANISM: Artificial Sequence
<220> FEATURE:
<223> OTHER INFORMATION: Synthetic primer

<400> SEQUENCE: 10
gggcccaggc ggcccagtcg gtggaggagt cctgg                              35

<210> SEQ ID NO 11
<211> LENGTH: 35
<212> TYPE: DNA
<213> ORGANISM: Artificial Sequence
<220> FEATURE:
<223> OTHER INFORMATION: Synthetic primer

<400> SEQUENCE: 11
gggcccaggc ggcccagtcg gtgaaggagt ccgag                              35

<210> SEQ ID NO 12
<211> LENGTH: 35
<212> TYPE: DNA
<213> ORGANISM: Artificial Sequence
<220> FEATURE:
<223> OTHER INFORMATION: Synthetic primer

<400> SEQUENCE: 12
gggcccaggc ggcccagtcg ytggaggagt ccggg                              35

<210> SEQ ID NO 13
<211> LENGTH: 37
<212> TYPE: DNA
<213> ORGANISM: Artificial Sequence
<220> FEATURE:
<223> OTHER INFORMATION: Synthetic primer

<400> SEQUENCE: 13
gggcccaggc ggcccagsag cagctgrtgg agtccgg                                    37

<210> SEQ ID NO 14
<211> LENGTH: 38
<212> TYPE: DNA
<213> ORGANISM: Artificial Sequence
<220> FEATURE:
<223> OTHER INFORMATION: Synthetic primer

<400> SEQUENCE: 14
gggcccaggc ggccgagctc gtgmtgaccc agactcca                                   38

<210> SEQ ID NO 15
<211> LENGTH: 38
<212> TYPE: DNA
<213> ORGANISM: Artificial Sequence
<220> FEATURE:
<223> OTHER INFORMATION: Synthetic primer

<400> SEQUENCE: 15
gggcccaggc ggccgagctc gatmtgaccc agactcca                                   38

<210> SEQ ID NO 16
<211> LENGTH: 38
<212> TYPE: DNA
<213> ORGANISM: Artificial Sequence
<220> FEATURE:
<223> OTHER INFORMATION: Synthetic primer

<400> SEQUENCE: 16
gggcccaggc ggccgagctc gtgatgaccc agactgaa                                   38

<210> SEQ ID NO 17
<211> LENGTH: 40
<212> TYPE: DNA
<213> ORGANISM: Artificial Sequence
<220> FEATURE:
<223> OTHER INFORMATION: Synthetic primer

<400> SEQUENCE: 17
gggcccaggc ggccgagctc gtgctgactc agtcgccctc                                 40

<210> SEQ ID NO 18
<211> LENGTH: 46
<212> TYPE: DNA
<213> ORGANISM: Artificial Sequence
<220> FEATURE:
<223> OTHER INFORMATION: Synthetic primer

<400> SEQUENCE: 18
cctggccggc ctggccacta gtgactgayg gagccttagg ttgccc                          46

<210> SEQ ID NO 19
<211> LENGTH: 37
<212> TYPE: DNA
<213> ORGANISM: Artificial Sequence
<220> FEATURE:
<223> OTHER INFORMATION: Synthetic primer

<400> SEQUENCE: 19
cctggccggc ctggcctttg atttccacat tggtgcc                                    37

<210> SEQ ID NO 20
<211> LENGTH: 37
<212> TYPE: DNA
<213> ORGANISM: Artificial Sequence

```
<220> FEATURE:
<223> OTHER INFORMATION: Synthetic primer

<400> SEQUENCE: 20
cctggccggc ctggcctagg atctccagct cggtccc                              37

<210> SEQ ID NO 21
<211> LENGTH: 37
<212> TYPE: DNA
<213> ORGANISM: Artificial Sequence
<220> FEATURE:
<223> OTHER INFORMATION: Synthetic primer

<400> SEQUENCE: 21
cctggccggc ctggcctttg acsaccacct cggtccc                              37

<210> SEQ ID NO 22
<211> LENGTH: 40
<212> TYPE: DNA
<213> ORGANISM: Artificial Sequence
<220> FEATURE:
<223> OTHER INFORMATION: Synthetic primer

<400> SEQUENCE: 22
cctggccggc ctggccgcct gtgacggtca gctgggtccc                           40

<210> SEQ ID NO 23
<211> LENGTH: 25
<212> TYPE: PRT
<213> ORGANISM: Oryctolagus

<400> SEQUENCE: 23
```

Gln Gln Gln Leu Val Glu Ser Gly Gly Arg Leu Val Lys Pro Asp Glu
1               5                   10                  15

Thr Leu Thr Ile Thr Cys Thr Val Ser
            20                  25

```
<210> SEQ ID NO 24
<211> LENGTH: 24
<212> TYPE: PRT
<213> ORGANISM: Oryctolagus

<400> SEQUENCE: 24
```

Gln Ser Val Glu Glu Ser Gly Gly Gly Leu Val Thr Pro Gly Thr Pro
1               5                   10                  15

Leu Thr Leu Thr Cys Thr Val Ser
            20

```
<210> SEQ ID NO 25
<211> LENGTH: 24
<212> TYPE: PRT
<213> ORGANISM: Oryctolagus

<400> SEQUENCE: 25
```

Gln Ser Leu Glu Glu Ser Gly Gly Gly Leu Val Gln Pro Gly Gly Ser
1               5                   10                  15

Leu Lys Val Ser Cys Lys Ala Ser
            20

```
<210> SEQ ID NO 26
<211> LENGTH: 24
<212> TYPE: PRT
<213> ORGANISM: Oryctolagus
```

```
<400> SEQUENCE: 26

Gln Ser Leu Glu Glu Ser Gly Gly Arg Leu Val Thr Pro Gly Thr Pro
1               5                   10                  15

Leu Thr Leu Thr Cys Thr Val Ser
            20

<210> SEQ ID NO 27
<211> LENGTH: 25
<212> TYPE: PRT
<213> ORGANISM: Oryctolagus

<400> SEQUENCE: 27

Gln Gln Gln Leu Met Lys Ser Gly Gly Gly Leu Val Gln Pro Gly Gly
1               5                   10                  15

Ser Leu Thr Leu Ser Cys Lys Ala Ser
            20                  25

<210> SEQ ID NO 28
<211> LENGTH: 24
<212> TYPE: PRT
<213> ORGANISM: Oryctolagus

<400> SEQUENCE: 28

Gln Ser Leu Glu Glu Ser Gly Gly Arg Leu Val Thr Pro Gly Gly Ser
1               5                   10                  15

Leu Thr Pro Thr Cys Thr Val Ser
            20

<210> SEQ ID NO 29
<211> LENGTH: 24
<212> TYPE: PRT
<213> ORGANISM: Oryctolagus

<400> SEQUENCE: 29

Gln Ser Val Glu Glu Ser Gly Gly Arg Leu Val Lys Pro Asp Glu Thr
1               5                   10                  15

Leu Thr Leu Thr Cys Thr Val Ser
            20

<210> SEQ ID NO 30
<211> LENGTH: 24
<212> TYPE: PRT
<213> ORGANISM: Oryctolagus

<400> SEQUENCE: 30

Gln Ser Val Glu Glu Ser Arg Gly Arg Leu Val Thr Pro Gly Thr Pro
1               5                   10                  15

Leu Thr Leu Thr Cys Thr Val Ser
            20

<210> SEQ ID NO 31
<211> LENGTH: 25
<212> TYPE: PRT
<213> ORGANISM: Oryctolagus

<400> SEQUENCE: 31

Gln Glu Gln Leu Val Glu Ser Gly Gly Gly Leu Val Gln Pro Gly Gly
1               5                   10                  15

Ser Leu Lys Leu Ser Cys Lys Ala Ser
            20                  25
```

```
<210> SEQ ID NO 32
<211> LENGTH: 25
<212> TYPE: PRT
<213> ORGANISM: Oryctolagus

<400> SEQUENCE: 32

Gln Gln Gln Leu Val Glu Ser Gly Gly Gly Leu Val Gln Pro Gly Gly
1               5                   10                  15

Ser Leu Lys Leu Ser Cys Lys Ala Ser
            20                  25

<210> SEQ ID NO 33
<211> LENGTH: 24
<212> TYPE: PRT
<213> ORGANISM: Oryctolagus

<400> SEQUENCE: 33

Gln Ser Met Lys Glu Ser Glu Gly Arg Leu Val Thr Pro Gly Gly Ser
1               5                   10                  15

Leu Thr Leu Thr Cys Thr Val Ser
            20

<210> SEQ ID NO 34
<211> LENGTH: 24
<212> TYPE: PRT
<213> ORGANISM: Oryctolagus

<400> SEQUENCE: 34

Gln Ser Val Glu Glu Ser Arg Gly Arg Leu Val Thr Pro Gly Gly Ser
1               5                   10                  15

Leu Thr Leu Thr Cys Thr Val Ser
            20

<210> SEQ ID NO 35
<211> LENGTH: 24
<212> TYPE: PRT
<213> ORGANISM: Oryctolagus

<400> SEQUENCE: 35

Gln Ser Val Glu Glu Ser Gly Gly Gly Leu Val Gln Pro Gly Gly Ser
1               5                   10                  15

Leu Lys Val Ser Cys Lys Ala Pro
            20

<210> SEQ ID NO 36
<211> LENGTH: 24
<212> TYPE: PRT
<213> ORGANISM: Oryctolagus

<400> SEQUENCE: 36

Gln Ser Leu Glu Glu Ser Gly Gly Arg Leu Val Thr Pro Gly Gly Ser
1               5                   10                  15

Leu Thr Leu Thr Cys Thr Val Ser
            20

<210> SEQ ID NO 37
<211> LENGTH: 24
<212> TYPE: PRT
<213> ORGANISM: Oryctolagus

<400> SEQUENCE: 37

Gln Ser Val Glu Glu Ser Gly Gly Arg Leu Val Thr Pro Gly Gly Ser
1               5                   10                  15
```

```
Leu Thr Leu Thr Cys Thr Val Ser
            20

<210> SEQ ID NO 38
<211> LENGTH: 25
<212> TYPE: PRT
<213> ORGANISM: Oryctolagus

<400> SEQUENCE: 38

Gln Glu Gln Leu Met Glu Ser Gly Gly Gly Leu Val Gln Pro Gly Gly
1               5                  10                  15

Ser Leu Thr Leu Ser Cys Lys Ala Ser
            20                  25

<210> SEQ ID NO 39
<211> LENGTH: 24
<212> TYPE: PRT
<213> ORGANISM: Oryctolagus

<400> SEQUENCE: 39

Gln Ser Leu Glu Glu Ser Gly Gly Arg Leu Val Thr Pro Gly Thr Pro
1               5                  10                  15

Leu Thr Leu Thr Cys Thr Ala Ser
            20

<210> SEQ ID NO 40
<211> LENGTH: 25
<212> TYPE: PRT
<213> ORGANISM: Oryctolagus

<400> SEQUENCE: 40

Gln Gln Gln Leu Val Glu Ser Gly Gly Gly Leu Val Gln Pro Gly Gly
1               5                  10                  15

Ser Leu Thr Leu Ser Cys Lys Ala Ser
            20                  25

<210> SEQ ID NO 41
<211> LENGTH: 24
<212> TYPE: PRT
<213> ORGANISM: Oryctolagus

<400> SEQUENCE: 41

Gln Ser Val Glu Glu Ser Gly Gly Arg Leu Val Thr Pro Gly Thr Pro
1               5                  10                  15

Leu Thr Leu Thr Cys Thr Val Ser
            20

<210> SEQ ID NO 42
<211> LENGTH: 24
<212> TYPE: PRT
<213> ORGANISM: Oryctolagus

<400> SEQUENCE: 42

Gln Ser Val Glu Glu Ser Arg Gly Gly Leu Val Gln Pro Gly Gly Ser
1               5                  10                  15

Leu Lys Val Ser Cys Lys Ala Ser
            20

<210> SEQ ID NO 43
<211> LENGTH: 24
<212> TYPE: PRT
<213> ORGANISM: Oryctolagus
```

<400> SEQUENCE: 43

Gln Ser Val Glu Glu Ser Arg Gly Gly Leu Phe Lys Pro Thr Asp Thr
1               5                   10                  15

Leu Thr Leu Thr Cys Thr Val Ser
            20

<210> SEQ ID NO 44
<211> LENGTH: 24
<212> TYPE: PRT
<213> ORGANISM: Oryctolagus

<400> SEQUENCE: 44

Gln Ser Val Glu Glu Ser Gly Gly Arg Leu Ile Ser Pro Gly Gly Ser
1               5                   10                  15

Leu Thr Leu Thr Cys Thr Val Ser
            20

<210> SEQ ID NO 45
<211> LENGTH: 24
<212> TYPE: PRT
<213> ORGANISM: Oryctolagus

<400> SEQUENCE: 45

Gln Ser Leu Glu Glu Ser Gly Gly Arg Leu Val Lys Pro Asp Glu Thr
1               5                   10                  15

Leu Thr Leu Thr Cys Thr Val Ser
            20

<210> SEQ ID NO 46
<211> LENGTH: 24
<212> TYPE: PRT
<213> ORGANISM: Oryctolagus

<400> SEQUENCE: 46

Gln Ser Val Glu Glu Ser Arg Gly Arg Leu Val Thr Pro Gly Thr Pro
1               5                   10                  15

Leu Thr Leu Thr Cys Thr Ala Ser
            20

<210> SEQ ID NO 47
<211> LENGTH: 24
<212> TYPE: PRT
<213> ORGANISM: Oryctolagus

<400> SEQUENCE: 47

Gln Ser Val Glu Glu Ser Arg Gly Arg Leu Val Lys Pro Asp Glu Thr
1               5                   10                  15

Leu Thr Leu Thr Cys Thr Val Ser
            20

<210> SEQ ID NO 48
<211> LENGTH: 24
<212> TYPE: PRT
<213> ORGANISM: Oryctolagus

<400> SEQUENCE: 48

Gln Ser Val Glu Glu Ser Arg Gly Asp Leu Val Lys Pro Glu Gly Ser
1               5                   10                  15

Leu Thr Leu Thr Cys Thr Ala Ser
            20

<210> SEQ ID NO 49
<211> LENGTH: 24
<212> TYPE: PRT
<213> ORGANISM: Oryctolagus

<400> SEQUENCE: 49

Gln Ser Leu Glu Glu Ser Gly Gly Arg Leu Val Thr Pro Gly Thr Pro
1               5                   10                  15

Leu Thr Leu Thr Cys Thr Ile Ser
            20

<210> SEQ ID NO 50
<211> LENGTH: 24
<212> TYPE: PRT
<213> ORGANISM: Oryctolagus

<400> SEQUENCE: 50

Gln Ser Leu Glu Glu Ser Gly Gly Arg Leu Val Thr Leu Gly Thr Pro
1               5                   10                  15

Leu Thr Leu Thr Cys Thr Val Ser
            20

<210> SEQ ID NO 51
<211> LENGTH: 24
<212> TYPE: PRT
<213> ORGANISM: Oryctolagus

<400> SEQUENCE: 51

Gln Ser Leu Glu Glu Ser Trp Gly Arg Leu Val Lys Pro Asp Glu Thr
1               5                   10                  15

Leu Thr Ile Thr Cys Thr Val Ser
            20

<210> SEQ ID NO 52
<211> LENGTH: 24
<212> TYPE: PRT
<213> ORGANISM: Oryctolagus

<400> SEQUENCE: 52

Gln Ser Val Glu Glu Ser Gly Gly Gly Leu Val Gln Pro Gly Gly Ser
1               5                   10                  15

Leu Lys Leu Ser Cys Lys Ala Ser
            20

<210> SEQ ID NO 53
<211> LENGTH: 25
<212> TYPE: PRT
<213> ORGANISM: Oryctolagus

<400> SEQUENCE: 53

Gln Glu Gln Leu Val Glu Ser Gly Gly Gly Leu Val Lys Pro Glu Gly
1               5                   10                  15

Ser Leu Thr Leu Thr Cys Lys Ala Ser
            20                  25

<210> SEQ ID NO 54
<211> LENGTH: 24
<212> TYPE: PRT
<213> ORGANISM: Oryctolagus

<400> SEQUENCE: 54

Gln Ser Val Glu Glu Ser Gly Gly Asn Leu Val Thr Pro Gly Thr Pro

```
1               5                   10                  15
Leu Thr Leu Thr Cys Thr Val Ser
            20

<210> SEQ ID NO 55
<211> LENGTH: 25
<212> TYPE: PRT
<213> ORGANISM: Oryctolagus

<400> SEQUENCE: 55

Gln Gln Gln Leu Met Glu Ser Gly Gly Gly Leu Val Gln Pro Gly Gly
1               5                   10                  15

Ser Leu Lys Leu Ser Cys Lys Ala Ser
            20                  25

<210> SEQ ID NO 56
<211> LENGTH: 31
<212> TYPE: PRT
<213> ORGANISM: Oryctolagus

<400> SEQUENCE: 56

Gln Glu Gln Leu Met Glu Thr Glu Ser Gly Gly Gly Ala Glu Gly Gly
1               5                   10                  15

Leu Val Lys Pro Gly Gly Ser Leu Glu Leu Cys Cys Lys Ala Ser
            20                  25                  30

<210> SEQ ID NO 57
<211> LENGTH: 31
<212> TYPE: PRT
<213> ORGANISM: Oryctolagus

<400> SEQUENCE: 57

Gln Glu Gln Leu Met Glu Thr Glu Ser Gly Gly Gly Ala Glu Gly Gly
1               5                   10                  15

Leu Val Lys Pro Gly Ala Ser Leu Thr Leu Thr Cys Thr Ala Ser
            20                  25                  30

<210> SEQ ID NO 58
<211> LENGTH: 24
<212> TYPE: PRT
<213> ORGANISM: Oryctolagus

<400> SEQUENCE: 58

Gln Ser Leu Glu Glu Ser Gly Gly Arg Leu Val Thr Pro Gly Thr Pro
1               5                   10                  15

Leu Thr Leu Thr Cys Thr Val Ser
            20

<210> SEQ ID NO 59
<211> LENGTH: 24
<212> TYPE: PRT
<213> ORGANISM: Oryctolagus

<400> SEQUENCE: 59

Gln Ser Val Glu Glu Ser Arg Gly Asp Leu Val Lys Pro Gly Ala Ser
1               5                   10                  15

Leu Thr Leu Thr Cys Thr Ala Ser
            20

<210> SEQ ID NO 60
<211> LENGTH: 24
<212> TYPE: PRT
```

<213> ORGANISM: Oryctolagus

<400> SEQUENCE: 60

Gln Ser Val Glu Glu Ser Gly Gly Arg Leu Ile Thr Pro Gly Gly Ser
1               5                   10                  15
Leu Thr Leu Thr Cys Thr Val Ser
            20

<210> SEQ ID NO 61
<211> LENGTH: 24
<212> TYPE: PRT
<213> ORGANISM: Oryctolagus

<400> SEQUENCE: 61

Gln Ser Leu Glu Glu Ser Gly Gly Asp Leu Val Lys Pro Gly Ala Ser
1               5                   10                  15
Leu Thr Leu Thr Cys Thr Ala Ser
            20

<210> SEQ ID NO 62
<211> LENGTH: 24
<212> TYPE: PRT
<213> ORGANISM: Oryctolagus

<400> SEQUENCE: 62

Gln Ser Val Glu Glu Ser Arg Gly Arg Leu Val Thr Pro Gly Thr Pro
1               5                   10                  15
Leu Thr Leu Thr Cys Thr Val Ser
            20

<210> SEQ ID NO 63
<211> LENGTH: 27
<212> TYPE: PRT
<213> ORGANISM: Oryctolagus

<400> SEQUENCE: 63

Gln Glu Gln Leu Met Glu Thr Glu Ser Gly Gly Gly Leu Val Lys Pro
1               5                   10                  15
Gly Ala Ser Leu Thr Leu Thr Cys Thr Ala Ser
            20                  25

<210> SEQ ID NO 64
<211> LENGTH: 24
<212> TYPE: PRT
<213> ORGANISM: Oryctolagus

<400> SEQUENCE: 64

Gln Ser Leu Glu Glu Ser Gly Gly Asp Leu Val Gln Pro Gly Ala Ser
1               5                   10                  15
Leu Thr Leu Thr Cys Thr Ala Ser
            20

<210> SEQ ID NO 65
<211> LENGTH: 25
<212> TYPE: PRT
<213> ORGANISM: Oryctolagus

<400> SEQUENCE: 65

Gln Gln Gln Leu Val Glu Ser Gly Gly Asp Leu Val Lys Pro Glu Gly
1               5                   10                  15
Ser Leu Thr Leu Thr Cys Thr Ala Ser
            20                  25

```
<210> SEQ ID NO 66
<211> LENGTH: 24
<212> TYPE: PRT
<213> ORGANISM: Oryctolagus

<400> SEQUENCE: 66

Gln Ser Leu Glu Glu Ser Gly Gly Asp Leu Val Lys Pro Glu Gly Ser
1               5                   10                  15

Leu Thr Leu Thr Cys Thr Ala Ser
            20

<210> SEQ ID NO 67
<211> LENGTH: 14
<212> TYPE: PRT
<213> ORGANISM: Oryctolagus

<400> SEQUENCE: 67

Trp Val Arg Gln Ala Pro Gly Glu Gly Leu Glu Trp Ile Gly
1               5                   10

<210> SEQ ID NO 68
<211> LENGTH: 14
<212> TYPE: PRT
<213> ORGANISM: Oryctolagus

<400> SEQUENCE: 68

Trp Val Arg Gln Ala Pro Gly Lys Gly Leu Gln Tyr Ile Gly
1               5                   10

<210> SEQ ID NO 69
<211> LENGTH: 14
<212> TYPE: PRT
<213> ORGANISM: Oryctolagus

<400> SEQUENCE: 69

Trp Val Arg Gln Ala Pro Gly Lys Gly Leu Glu Trp Ile Gly
1               5                   10

<210> SEQ ID NO 70
<211> LENGTH: 14
<212> TYPE: PRT
<213> ORGANISM: Oryctolagus

<400> SEQUENCE: 70

Trp Val Arg Gln Ala Pro Gly Lys Gly Leu Asp Trp Ile Gly
1               5                   10

<210> SEQ ID NO 71
<211> LENGTH: 14
<212> TYPE: PRT
<213> ORGANISM: Oryctolagus

<400> SEQUENCE: 71

Trp Val Arg Gln Ala Pro Gly Glu Gly Leu Asp Trp Ile Gly
1               5                   10

<210> SEQ ID NO 72
<211> LENGTH: 14
<212> TYPE: PRT
<213> ORGANISM: Oryctolagus

<400> SEQUENCE: 72

Trp Val Arg Gln Ala Pro Gly Lys Gly Leu Glu Tyr Ile Gly
```

```
1               5                   10
```

<210> SEQ ID NO 73
<211> LENGTH: 14
<212> TYPE: PRT
<213> ORGANISM: Oryctolagus

<400> SEQUENCE: 73

```
Trp Gly Arg Gln Ala Pro Arg Glu Gly Leu Glu Trp Ile Gly
1               5                   10
```

<210> SEQ ID NO 74
<211> LENGTH: 14
<212> TYPE: PRT
<213> ORGANISM: Oryctolagus

<400> SEQUENCE: 74

```
Trp Val Arg Gln Ala Pro Gly Lys Arg Leu Glu Trp Ile Gly
1               5                   10
```

<210> SEQ ID NO 75
<211> LENGTH: 14
<212> TYPE: PRT
<213> ORGANISM: Oryctolagus

<400> SEQUENCE: 75

```
Trp Val Arg Gln Ala Pro Gly Lys Gly Leu Glu Trp Val Ala
1               5                   10
```

<210> SEQ ID NO 76
<211> LENGTH: 14
<212> TYPE: PRT
<213> ORGANISM: Oryctolagus

<400> SEQUENCE: 76

```
Trp Val Arg Gln Ala Pro Glu Lys Gly Leu Glu Trp Ile Gly
1               5                   10
```

<210> SEQ ID NO 77
<211> LENGTH: 14
<212> TYPE: PRT
<213> ORGANISM: Oryctolagus

<400> SEQUENCE: 77

```
Trp Val Arg Gln Ala Pro Gly Lys Gly Leu Glu Trp Ile Ala
1               5                   10
```

<210> SEQ ID NO 78
<211> LENGTH: 14
<212> TYPE: PRT
<213> ORGANISM: Oryctolagus

<400> SEQUENCE: 78

```
Trp Phe Arg Gln Ala Pro Gly Lys Gly Leu Glu Trp Ile Ala
1               5                   10
```

<210> SEQ ID NO 79
<211> LENGTH: 14
<212> TYPE: PRT
<213> ORGANISM: Artificial Sequence
<220> FEATURE:
<223> OTHER INFORMATION: Oryctolagus

<400> SEQUENCE: 79

```
Trp Phe Arg Gln Ala Pro Gly Lys Gly Leu Glu Trp Ile Gly
```

<210> SEQ ID NO 80
<211> LENGTH: 14
<212> TYPE: PRT
<213> ORGANISM: Artificial Sequence
<220> FEATURE:
<223> OTHER INFORMATION: Oryctolagus

<400> SEQUENCE: 80

Trp Phe Arg Gln Ala Pro Gly Lys Glu Leu Glu Trp Ile Gly
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Oryctolagus

<400> SEQUENCE: 81

Trp Phe Arg Gln Ala Pro Gly Lys Gly Arg Glu Trp Ile Gly
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Oryctolagus

<400> SEQUENCE: 82

Trp Phe Arg Gln Ala Pro Gly Lys Gly Leu Glu Gly Ile Gly
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Oryctolagus

<400> SEQUENCE: 83

Trp Val Arg Gln Ala Pro Gly Lys Glu Leu Glu Trp Ile Gly
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Oryctolagus

<400> SEQUENCE: 84

Trp Val Arg Gln Ala Pro Gly Lys Glu Arg Glu Trp Ile Gly
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Oryctolagus

<400> SEQUENCE: 85

Trp Val Arg Gln Ala Pro Gly Lys Glu Leu Glu Gly Ile Gly
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Oryctolagus

<400> SEQUENCE: 86

Trp Val Arg Gln Ala Pro Gly Lys Gly Arg Glu Trp Ile Gly
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Oryctolagus

<400> SEQUENCE: 87

Trp Val Arg Gln Ala Pro Gly Lys Gly Arg Glu Gly Ile Gly
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Oryctolagus

<400> SEQUENCE: 88

Trp Val Arg Gln Ala Pro Gly Lys Gly Leu Glu Gly Ile Gly
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Oryctolagus

<400> SEQUENCE: 89

Trp Phe Arg Gln Ala Pro Gly Lys Glu Arg Glu Trp Ile Gly
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Oryctolagus

<400> SEQUENCE: 90

Trp Phe Arg Gln Ala Pro Gly Lys Glu Leu Glu Gly Ile Gly
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Oryctolagus

<400> SEQUENCE: 91

Trp Phe Arg Gln Ala Pro Gly Lys Gly Arg Glu Gly Ile Gly
1               5                   10

```
<210> SEQ ID NO 92
<211> LENGTH: 14
<212> TYPE: PRT
<213> ORGANISM: Artificial Sequence
<220> FEATURE:
<223> OTHER INFORMATION: Oryctolagus

<400> SEQUENCE: 92

Trp Val Arg Gln Ala Pro Gly Lys Glu Arg Glu Gly Ile Gly
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Oryctolagus

<400> SEQUENCE: 93

Trp Phe Arg Gln Ala Pro Gly Lys Glu Arg Glu Gly Ile Gly
1               5                   10

<210> SEQ ID NO 94
<211> LENGTH: 38
<212> TYPE: PRT
<213> ORGANISM: Oryctolagus

<400> SEQUENCE: 94

Tyr Ala Ser Trp Ala Lys Gly Arg Phe Thr Ile Ser Lys Thr Ser Ser
1               5                   10                  15

Thr Thr Val Asp Leu Lys Ile Thr Ser Pro Thr Thr Glu Asp Thr Ala
            20                  25                  30

Thr Tyr Phe Cys Ala Arg
        35

<210> SEQ ID NO 95
<211> LENGTH: 39
<212> TYPE: PRT
<213> ORGANISM: Oryctolagus

<400> SEQUENCE: 95

Tyr Ala Thr Trp Val Asn Gly Arg Phe Thr Leu Ser Arg Asp Ile Asp
1               5                   10                  15

Gln Ser Thr Gly Cys Leu Gln Leu Asn Ser Leu Thr Ala Ala Asp Thr
            20                  25                  30

Ala Thr Tyr Tyr Cys Ala Arg
        35

<210> SEQ ID NO 96
<211> LENGTH: 39
<212> TYPE: PRT
<213> ORGANISM: Oryctolagus

<400> SEQUENCE: 96

Tyr Ala Thr Trp Ala Lys Gly Arg Phe Thr Ile Ser Lys Thr Ser Thr
1               5                   10                  15

Thr Val Asn Leu Gln Met Glu Thr Thr Ser Leu Thr Thr Glu Asp Thr
            20                  25                  30

Ala Thr Phe Phe Cys Ala Arg
        35

<210> SEQ ID NO 97
```

```
<211> LENGTH: 40
<212> TYPE: PRT
<213> ORGANISM: Oryctolagus

<400> SEQUENCE: 97

Tyr Ala Thr Trp Ala Lys Gly Arg Phe Thr Ile Ser Lys Thr Ser Ser
1               5                   10                  15

Thr Thr Val Thr Leu Gln Met Glu Thr Thr Ser Leu Thr Ala Ala Asp
            20                  25                  30

Thr Ala Thr Tyr Phe Cys Ala Arg
        35                  40

<210> SEQ ID NO 98
<211> LENGTH: 37
<212> TYPE: PRT
<213> ORGANISM: Oryctolagus

<400> SEQUENCE: 98

Tyr Ala Ser Trp Ala Lys Gly Arg Phe Thr Ile Ser Lys Thr Ser Thr
1               5                   10                  15

Thr Val Asp Leu Lys Ile Thr Ser Pro Thr Thr Glu Asp Thr Ala Thr
            20                  25                  30

Tyr Phe Cys Ala Ser
        35

<210> SEQ ID NO 99
<211> LENGTH: 40
<212> TYPE: PRT
<213> ORGANISM: Oryctolagus

<400> SEQUENCE: 99

Tyr Ala Ser Trp Ala Glu Gly Arg Phe Ser Ile Ser Lys Ala Ser Ser
1               5                   10                  15

Thr Thr Val Thr Leu Gln Met Glu Thr Thr Ser Leu Thr Ala Ala Asp
            20                  25                  30

Thr Ala Thr Tyr Phe Cys Ala Arg
        35                  40

<210> SEQ ID NO 100
<211> LENGTH: 37
<212> TYPE: PRT
<213> ORGANISM: Oryctolagus

<400> SEQUENCE: 100

Tyr Ala Asn Trp Ala Lys Gly Arg Phe Thr Ile Ser Lys Thr Ser Thr
1               5                   10                  15

Thr Val Asp Leu Lys Ile Thr Ser Pro Thr Thr Glu Asp Thr Ala Thr
            20                  25                  30

Tyr Phe Cys Val Arg
        35

<210> SEQ ID NO 101
<211> LENGTH: 40
<212> TYPE: PRT
<213> ORGANISM: Oryctolagus

<400> SEQUENCE: 101

Tyr Ala Ser Trp Pro Gln Gly Arg Phe Thr Ile Ser Val Thr Ser Ser
1               5                   10                  15

Thr Thr Val Thr Leu Gln Met Glu Thr Thr Ser Leu Thr Ala Ala Asp
            20                  25                  30
```

-continued

```
Thr Ala Thr Tyr Phe Cys Ala Lys
        35                  40

<210> SEQ ID NO 102
<211> LENGTH: 37
<212> TYPE: PRT
<213> ORGANISM: Oryctolagus

<400> SEQUENCE: 102

Tyr Ala Ser Trp Ala Lys Gly Arg Phe Thr Ile Ser Gln Thr Ser Thr
1               5                   10                  15

Thr Val Asp Leu Lys Ile Thr Ser Pro Thr Thr Glu Asp Thr Ala Thr
            20                  25                  30

Tyr Phe Cys Ala Arg
        35

<210> SEQ ID NO 103
<211> LENGTH: 40
<212> TYPE: PRT
<213> ORGANISM: Oryctolagus

<400> SEQUENCE: 103

Tyr Ala Thr Trp Ala Lys Gly Arg Phe Thr Ile Ser Lys Pro Ser Ser
1               5                   10                  15

Thr Thr Val Thr Leu Gln Met Glu Thr Thr Ser Leu Thr Ala Ala Asp
            20                  25                  30

Thr Ala Thr Tyr Phe Cys Ala Arg
        35                  40

<210> SEQ ID NO 104
<211> LENGTH: 40
<212> TYPE: PRT
<213> ORGANISM: Oryctolagus

<400> SEQUENCE: 104

Tyr Ala Asn Trp Ala Lys Gly Arg Phe Thr Ile Ala Lys Thr Ser Ser
1               5                   10                  15

Thr Thr Val Thr Leu Gln Met Glu Thr Thr Ser Leu Thr Ala Ala Asp
            20                  25                  30

Thr Ala Thr Tyr Phe Cys Ala Arg
        35                  40

<210> SEQ ID NO 105
<211> LENGTH: 37
<212> TYPE: PRT
<213> ORGANISM: Oryctolagus

<400> SEQUENCE: 105

Tyr Ala Ser Trp Ala Lys Gly Arg Phe Thr Ile Ser Lys Thr Ser Thr
1               5                   10                  15

Thr Val Asp Leu Lys Ile Thr Ser Pro Thr Thr Glu Asp Thr Ala Thr
            20                  25                  30

Tyr Phe Cys Ala Arg
        35

<210> SEQ ID NO 106
<211> LENGTH: 37
<212> TYPE: PRT
<213> ORGANISM: Oryctolagus

<400> SEQUENCE: 106
```

```
<210> SEQ ID NO 107
<211> LENGTH: 39
<212> TYPE: PRT
<213> ORGANISM: Oryctolagus

<400> SEQUENCE: 107

Tyr Pro Ser Trp Val Asp Gly Arg Phe Thr Ile Ser Lys Thr Ser Thr
1               5                   10                  15

Thr Val Asp Leu Lys Ile Thr Ser Pro Thr Thr Glu Asp Thr Ala Thr
            20                  25                  30

Tyr Phe Cys Ala Arg
        35

<210> SEQ ID NO 107
<211> LENGTH: 39
<212> TYPE: PRT
<213> ORGANISM: Oryctolagus

<400> SEQUENCE: 107

Tyr Ala Asp Trp Val Thr Gly Arg Phe Thr Ile Ser Ser His Asn Ala
1               5                   10                  15

Gln Asn Thr Leu Tyr Leu Gln Leu Asn Ser Leu Thr Ala Ala Asp Thr
            20                  25                  30

Ala Thr Tyr Phe Cys Ala Arg
        35

<210> SEQ ID NO 108
<211> LENGTH: 37
<212> TYPE: PRT
<213> ORGANISM: Oryctolagus

<400> SEQUENCE: 108

Tyr Ala Asn Trp Ala Lys Gly Arg Cys Thr Ile Ser Lys Thr Ser Thr
1               5                   10                  15

Thr Val Asp Leu Lys Ile Thr Ser Pro Thr Thr Glu Asp Thr Ala Thr
            20                  25                  30

Tyr Phe Cys Ala Pro
        35

<210> SEQ ID NO 109
<211> LENGTH: 39
<212> TYPE: PRT
<213> ORGANISM: Oryctolagus

<400> SEQUENCE: 109

Tyr Ala Thr Trp Val Asn Gly Arg Leu Thr Ile Ser Ser His Asn Ala
1               5                   10                  15

Gln Asn Thr Leu Tyr Leu Gln Leu Asn Ser Leu Thr Ala Ala Asp Thr
            20                  25                  30

Ala Thr Tyr Phe Cys Ala Arg
        35

<210> SEQ ID NO 110
<211> LENGTH: 37
<212> TYPE: PRT
<213> ORGANISM: Oryctolagus

<400> SEQUENCE: 110

Tyr Ala Asn Trp Ala Lys Gly Arg Phe Thr Ile Ser Lys Thr Pro Thr
1               5                   10                  15

Thr Val Asp Leu Lys Ile Asn Ser Pro Thr Thr Glu Asp Thr Ala Thr
            20                  25                  30

Tyr Phe Cys Ala Arg
        35
```

```
<210> SEQ ID NO 111
<211> LENGTH: 37
<212> TYPE: PRT
<213> ORGANISM: Oryctolagus

<400> SEQUENCE: 111

Tyr Ala Asp Trp Ala Lys Gly Arg Phe Thr Ile Ser Lys Thr Ser Thr
1               5                   10                  15

Thr Val Asp Leu Lys Ile Thr Ser Pro Thr Thr Glu Asp Thr Ala Thr
            20                  25                  30

Tyr Phe Cys Ala Arg
        35

<210> SEQ ID NO 112
<211> LENGTH: 37
<212> TYPE: PRT
<213> ORGANISM: Oryctolagus

<400> SEQUENCE: 112

Tyr Ala Asp Trp Ala Lys Gly Arg Phe Thr Ile Ser Lys Thr Ser Thr
1               5                   10                  15

Thr Met Asp Leu Lys Ile Thr Ser Pro Thr Thr Glu Asp Thr Ala Thr
            20                  25                  30

Tyr Phe Cys Gly Arg
        35

<210> SEQ ID NO 113
<211> LENGTH: 39
<212> TYPE: PRT
<213> ORGANISM: Oryctolagus

<400> SEQUENCE: 113

Tyr Ala Ser Trp Val Asn Gly Arg Phe Thr Ile Ser Ser Arg Asn Ala
1               5                   10                  15

Gln Asn Thr Leu Tyr Leu Gln Leu Asn Ser Leu Thr Ala Ala Asp Thr
            20                  25                  30

Ala Thr Tyr Phe Cys Ala Arg
        35

<210> SEQ ID NO 114
<211> LENGTH: 39
<212> TYPE: PRT
<213> ORGANISM: Oryctolagus

<400> SEQUENCE: 114

Tyr Ala Ser Trp Val Asn Gly Arg Phe Thr Ile Ser Ser Asp Asn Ala
1               5                   10                  15

Gln Asn Thr Val Asp Leu Gln Leu Asn Ser Leu Thr Ala Ala Asp Thr
            20                  25                  30

Ala Thr Tyr Phe Cys Ala Arg
        35

<210> SEQ ID NO 115
<211> LENGTH: 37
<212> TYPE: PRT
<213> ORGANISM: Oryctolagus

<400> SEQUENCE: 115

Tyr Ala Asn Trp Ala Lys Gly Arg Phe Thr Ser Ser Lys Thr Ser Thr
1               5                   10                  15

Thr Val Asp Leu Lys Ile Thr Ser Pro Thr Thr Glu Asp Thr Ala Thr
```

```
                    20                  25                  30

Tyr Phe Cys Ala Arg
        35

<210> SEQ ID NO 116
<211> LENGTH: 37
<212> TYPE: PRT
<213> ORGANISM: Oryctolagus

<400> SEQUENCE: 116

Tyr Ala Asn Trp Ala Lys Gly Arg Phe Thr Ile Ser Lys Thr Ser Thr
1               5                  10                  15

Thr Val Asp Leu Glu Ile Ala Ser Pro Thr Thr Glu Asp Thr Ala Thr
                    20                  25                  30

Tyr Phe Cys Val Arg
        35

<210> SEQ ID NO 117
<211> LENGTH: 38
<212> TYPE: PRT
<213> ORGANISM: Oryctolagus

<400> SEQUENCE: 117

Tyr Ala Ser Trp Ala Glu Gly Arg Phe Thr Ile Ser Lys Ala Ser Ser
1               5                  10                  15

Thr Thr Val Asp Leu Lys Met Thr Ser Leu Thr Thr Glu Asp Thr Ala
                    20                  25                  30

Thr Tyr Phe Cys Ala Arg
        35

<210> SEQ ID NO 118
<211> LENGTH: 37
<212> TYPE: PRT
<213> ORGANISM: Oryctolagus

<400> SEQUENCE: 118

Tyr Ala Asn Trp Ala Lys Gly Arg Phe Thr Ile Ser Arg Thr Ser Thr
1               5                  10                  15

Thr Val Asp Leu Lys Met Thr Ser Leu Thr Thr Glu Asp Thr Ala Thr
                    20                  25                  30

Tyr Phe Cys Ala Arg
        35

<210> SEQ ID NO 119
<211> LENGTH: 38
<212> TYPE: PRT
<213> ORGANISM: Oryctolagus

<400> SEQUENCE: 119

Tyr Ala Ser Trp Ala Lys Gly Arg Phe Thr Ile Ser Lys Thr Ser Ser
1               5                  10                  15

Thr Thr Val Asp Leu Glu Met Thr Ser Leu Thr Thr Glu Asp Thr Ala
                    20                  25                  30

Thr Tyr Phe Cys Ala Arg
        35

<210> SEQ ID NO 120
<211> LENGTH: 38
<212> TYPE: PRT
<213> ORGANISM: Oryctolagus
```

```
<400> SEQUENCE: 120

Tyr Ala Asn Trp Ala Lys Gly Arg Phe Thr Ile Ser Lys Ala Ser Ser
1               5                   10                  15

Thr Thr Val Glu Leu Lys Met Thr Gly Leu Thr Thr Glu Asp Thr Ala
            20                  25                  30

Thr Tyr Phe Cys Ala Arg
        35

<210> SEQ ID NO 121
<211> LENGTH: 39
<212> TYPE: PRT
<213> ORGANISM: Oryctolagus

<400> SEQUENCE: 121

Tyr Ala Ser Trp Val Asn Gly Arg Phe Thr Ile Ser Ser His Asn Ala
1               5                   10                  15

Gln Asn Thr Leu Tyr Leu Gln Leu Asn Ser Leu Thr Ala Ala Asp Thr
            20                  25                  30

Ala Thr Tyr Phe Cys Ala Arg
        35

<210> SEQ ID NO 122
<211> LENGTH: 37
<212> TYPE: PRT
<213> ORGANISM: Oryctolagus

<400> SEQUENCE: 122

Tyr Ala Asn Trp Ala Arg Gly Arg Phe Thr Ile Ser Arg Thr Ser Thr
1               5                   10                  15

Thr Val Asp Leu Glu Ile Thr Ser Pro Thr Thr Glu Asp Thr Ala Thr
            20                  25                  30

Tyr Phe Cys Gly Arg
        35

<210> SEQ ID NO 123
<211> LENGTH: 37
<212> TYPE: PRT
<213> ORGANISM: Oryctolagus

<400> SEQUENCE: 123

Tyr Ala Ser Trp Val Asn Gly Arg Phe Thr Ile Ser Arg Thr Ser Thr
1               5                   10                  15

Thr Val Asp Leu Lys Met Thr Ser Leu Thr Thr Glu Asp Thr Ala Thr
            20                  25                  30

Tyr Phe Cys Ile Arg
        35

<210> SEQ ID NO 124
<211> LENGTH: 37
<212> TYPE: PRT
<213> ORGANISM: Oryctolagus

<400> SEQUENCE: 124

Tyr Ala Arg Trp Ala Lys Asp Arg Val Thr Ile Ser Lys Thr Ser Thr
1               5                   10                  15

Thr Val Asp Leu Lys Ile Thr Ser Pro Thr Thr Glu Asp Thr Ala Thr
            20                  25                  30

Tyr Phe Cys Ala Arg
        35
```

<210> SEQ ID NO 125
<211> LENGTH: 37
<212> TYPE: PRT
<213> ORGANISM: Oryctolagus

<400> SEQUENCE: 125

Tyr Ala Asn Trp Ala Lys Gly Arg Phe Thr Ile Ser Lys Thr Ser Thr
1               5                   10                  15

Thr Val Asp Leu Glu Ile Ile Ser Pro Thr Lys Glu Asp Thr Ala Thr
            20                  25                  30

Tyr Phe Cys Ala Thr
        35

<210> SEQ ID NO 126
<211> LENGTH: 37
<212> TYPE: PRT
<213> ORGANISM: Oryctolagus

<400> SEQUENCE: 126

Tyr Ala Asn Trp Ala Lys Gly Arg Phe Thr Ile Ser Lys Ala Ser Thr
1               5                   10                  15

Thr Val Asp Leu Lys Ile Thr Ser Pro Thr Thr Glu Asp Thr Ala Thr
            20                  25                  30

Tyr Phe Cys Val Arg
        35

<210> SEQ ID NO 127
<211> LENGTH: 37
<212> TYPE: PRT
<213> ORGANISM: Oryctolagus

<400> SEQUENCE: 127

Tyr Ala Asn Trp Ala Arg Gly Arg Phe Thr Ile Ser Lys Thr Ser Thr
1               5                   10                  15

Thr Val Asp Leu Lys Met Thr Ser Pro Thr Thr Glu Asp Thr Ala Ile
            20                  25                  30

Tyr Phe Cys Ala Arg
        35

<210> SEQ ID NO 128
<211> LENGTH: 37
<212> TYPE: PRT
<213> ORGANISM: Oryctolagus

<400> SEQUENCE: 128

Tyr Ala Thr Trp Ala Lys Gly Arg Phe Thr Ile Ser Lys Thr Ser Thr
1               5                   10                  15

Thr Val Asp Leu Lys Val Thr Ser Pro Thr Thr Glu Asp Thr Ala Thr
            20                  25                  30

Tyr Phe Cys Ala Ser
        35

<210> SEQ ID NO 129
<211> LENGTH: 37
<212> TYPE: PRT
<213> ORGANISM: Oryctolagus

<400> SEQUENCE: 129

Tyr Pro Ser Trp Ala Glu Gly Arg Phe Thr Ile Ser Lys Thr Ser Thr
1               5                   10                  15

Thr Val Asp Leu Lys Ile Ala Ser Pro Ala Thr Glu Asp Thr Ala Thr
            20                  25                  30

Tyr Phe Cys Ala Arg
        35

<210> SEQ ID NO 130
<211> LENGTH: 37
<212> TYPE: PRT
<213> ORGANISM: Oryctolagus

<400> SEQUENCE: 130

Tyr Ala Ser Trp Ala Lys Gly Arg Phe Thr Ile Ser Arg Thr Ser Thr
1               5                   10                  15

Thr Ala Asp Leu Arg Ile Thr Ser Pro Thr Ile Glu Asp Thr Ala Thr
            20                  25                  30

Tyr Phe Cys Ala Arg
        35

<210> SEQ ID NO 131
<211> LENGTH: 37
<212> TYPE: PRT
<213> ORGANISM: Oryctolagus

<400> SEQUENCE: 131

Tyr Ala Asn Trp Ala Lys Gly Arg Phe Thr Ile Ser Lys Thr Ser Thr
1               5                   10                  15

Thr Val Asp Leu Lys Met Thr Ser Leu Thr Ala Ala Asp Thr Ala Thr
            20                  25                  30

Tyr Phe Cys Ala Arg
        35

<210> SEQ ID NO 132
<211> LENGTH: 38
<212> TYPE: PRT
<213> ORGANISM: Oryctolagus

<400> SEQUENCE: 132

Tyr Ala Thr Trp Ala Lys Gly Arg Phe Thr Ile Ser Lys Thr Ser Ser
1               5                   10                  15

Thr Thr Val Asp Leu Lys Met Thr Ser Leu Thr Thr Glu Asp Thr Ala
            20                  25                  30

Thr Tyr Phe Cys Thr Arg
        35

<210> SEQ ID NO 133
<211> LENGTH: 37
<212> TYPE: PRT
<213> ORGANISM: Oryctolagus

<400> SEQUENCE: 133

Tyr Ala Asn Trp Ala Lys Gly Arg Phe Thr Ile Ser Arg Thr Ser Thr
1               5                   10                  15

Thr Val Asp Leu Lys Met Thr Ser Pro Thr Thr Glu Asp Thr Ala Thr
            20                  25                  30

Tyr Phe Cys Ile Arg
        35

<210> SEQ ID NO 134
<211> LENGTH: 37
<212> TYPE: PRT
<213> ORGANISM: Oryctolagus

<400> SEQUENCE: 134

Tyr Ala Ser Trp Ala Glu Gly Arg Phe Thr Ile Ser Arg Thr Ser Thr
1               5                   10                  15

Thr Val Asp Leu Lys Met Thr Ser Pro Thr Thr Glu Asp Thr Ala Thr
            20                  25                  30

Tyr Phe Cys Ala Arg
            35

<210> SEQ ID NO 135
<211> LENGTH: 37
<212> TYPE: PRT
<213> ORGANISM: Oryctolagus

<400> SEQUENCE: 135

Tyr Ala Ser Trp Ala Lys Gly Pro Phe Thr Ile Ser Lys Thr Ser Thr
1               5                   10                  15

Thr Val Asp Leu Lys Met Thr Ser Pro Thr Thr Glu Asp Met Ala Thr
            20                  25                  30

Tyr Phe Cys Ala Arg
            35

<210> SEQ ID NO 136
<211> LENGTH: 37
<212> TYPE: PRT
<213> ORGANISM: Oryctolagus

<400> SEQUENCE: 136

Tyr Ala Ser Trp Ala Lys Gly Arg Phe Thr Ile Ser Lys Thr Ser Thr
1               5                   10                  15

Thr Val Asp Leu Lys Ile Thr Ser Pro Ile Thr Glu Asp Thr Ala Thr
            20                  25                  30

Tyr Phe Cys Ile Arg
            35

<210> SEQ ID NO 137
<211> LENGTH: 39
<212> TYPE: PRT
<213> ORGANISM: Oryctolagus

<400> SEQUENCE: 137

Tyr Ala Ser Trp Val Asn Gly Arg Phe Thr Ile Ser Ser Asp Asn Ala
1               5                   10                  15

Gln Asn Thr Val Asp Leu Gln Met Asn Ser Leu Thr Ala Ala Asp Thr
            20                  25                  30

Ala Thr Tyr Phe Cys Ala Arg
            35

<210> SEQ ID NO 138
<211> LENGTH: 39
<212> TYPE: PRT
<213> ORGANISM: Oryctolagus

<400> SEQUENCE: 138

Tyr Ala Asn Trp Val Asn Gly Arg Phe Thr Ile Ser Leu Asp Asn Ala
1               5                   10                  15

Gln Asn Thr Val Phe Leu Gln Met Thr Ser Leu Thr Ala Ala Asp Thr
            20                  25                  30

Ala Thr Tyr Phe Cys Ala Arg
            35

<210> SEQ ID NO 139
<211> LENGTH: 11
<212> TYPE: PRT
<213> ORGANISM: Oryctolagus

<400> SEQUENCE: 139

Trp Gly Gln Gly Thr Leu Val Thr Val Ser Ser
1               5                   10

<210> SEQ ID NO 140
<211> LENGTH: 11
<212> TYPE: PRT
<213> ORGANISM: Oryctolagus

<400> SEQUENCE: 140

Trp Gly Pro Gly Thr Leu Val Thr Val Ser Ser
1               5                   10

<210> SEQ ID NO 141
<211> LENGTH: 11
<212> TYPE: PRT
<213> ORGANISM: Oryctolagus

<400> SEQUENCE: 141

Trp Gly Gln Gly Ile Leu Val Thr Val Ser Ser
1               5                   10

<210> SEQ ID NO 142
<211> LENGTH: 11
<212> TYPE: PRT
<213> ORGANISM: Oryctolagus

<400> SEQUENCE: 142

Trp Gly Gln Gly Ala Leu Val Thr Val Ser Ser
1               5                   10

<210> SEQ ID NO 143
<211> LENGTH: 11
<212> TYPE: PRT
<213> ORGANISM: Oryctolagus

<400> SEQUENCE: 143

Trp Gly Pro Gly Thr Leu Val Thr Ile Ser Ser
1               5                   10

<210> SEQ ID NO 144
<211> LENGTH: 11
<212> TYPE: PRT
<213> ORGANISM: Oryctolagus

<400> SEQUENCE: 144

Trp Gly Gln Gly Thr Leu Val Thr Ala Ser Ser
1               5                   10

<210> SEQ ID NO 145
<211> LENGTH: 11
<212> TYPE: PRT
<213> ORGANISM: Oryctolagus

<400> SEQUENCE: 145

Trp Gly Pro Gly Thr Leu Val Ala Val Ser Ser
1               5                   10

<210> SEQ ID NO 146
<211> LENGTH: 11
<212> TYPE: PRT
<213> ORGANISM: Oryctolagus

<400> SEQUENCE: 146

Trp Gly Gln Gly Thr Arg Val Thr Val Ser Ser
1               5                   10

<210> SEQ ID NO 147
<211> LENGTH: 11
<212> TYPE: PRT
<213> ORGANISM: Oryctolagus

<400> SEQUENCE: 147

Trp Gly Pro Gly Thr Leu Val Thr Gly Ser Ser
1               5                   10

<210> SEQ ID NO 148
<211> LENGTH: 11
<212> TYPE: PRT
<213> ORGANISM: Oryctolagus

<400> SEQUENCE: 148

Trp Gly Gln Gly Ser Leu Val Thr Ile Ser Ser
1               5                   10

<210> SEQ ID NO 149
<211> LENGTH: 11
<212> TYPE: PRT
<213> ORGANISM: Oryctolagus

<400> SEQUENCE: 149

Arg Gly Gln Gly Ser Leu Val Thr Ile Ser Ser
1               5                   10

<210> SEQ ID NO 150
<211> LENGTH: 23
<212> TYPE: PRT
<213> ORGANISM: Oryctolagus

<400> SEQUENCE: 150

Glu Leu Val Leu Thr Gln Thr Pro Ser Leu Ser Ala Ser Val Gly
1               5                   10                  15

Glu Thr Val Arg Ile Arg Cys
            20

<210> SEQ ID NO 151
<211> LENGTH: 23
<212> TYPE: PRT
<213> ORGANISM: Oryctolagus

<400> SEQUENCE: 151

Glu Leu Asp Met Thr Gln Thr Pro Ala Ser Val Ser Glu Pro Val Gly
1               5                   10                  15

Gly Thr Val Thr Ile Lys Cys
            20

<210> SEQ ID NO 152
<211> LENGTH: 23
<212> TYPE: PRT
<213> ORGANISM: Oryctolagus -continued

```
<400> SEQUENCE: 152

Glu Leu Val Leu Thr Gln Thr Pro Ser Pro Val Ser Ala Ala Val Gly
1               5                   10                  15

Gly Thr Val Thr Ile Lys Cys
            20

<210> SEQ ID NO 153
<211> LENGTH: 23
<212> TYPE: PRT
<213> ORGANISM: Oryctolagus

<400> SEQUENCE: 153

Glu Leu Asp Leu Thr Gln Thr Pro Ala Ser Val Ser Glu Pro Val Gly
1               5                   10                  15

Gly Thr Val Thr Ile Lys Cys
            20

<210> SEQ ID NO 154
<211> LENGTH: 23
<212> TYPE: PRT
<213> ORGANISM: Oryctolagus

<400> SEQUENCE: 154

Glu Leu Val Leu Thr Gln Thr Pro Ser Ser Ala Ser Glu Pro Val Gly
1               5                   10                  15

Gly Thr Ala Thr Ile Lys Cys
            20

<210> SEQ ID NO 155
<211> LENGTH: 23
<212> TYPE: PRT
<213> ORGANISM: Oryctolagus

<400> SEQUENCE: 155

Glu Leu Val Leu Thr Gln Thr Pro Ser Ser Val Ser Ala Ala Val Gly
1               5                   10                  15

Gly Thr Val Thr Ile Asn Cys
            20

<210> SEQ ID NO 156
<211> LENGTH: 23
<212> TYPE: PRT
<213> ORGANISM: Oryctolagus

<400> SEQUENCE: 156

Glu Leu Asp Met Thr Gln Thr Pro Ala Ser Val Ser Ala Ala Val Gly
1               5                   10                  15

Gly Thr Val Thr Ile Asn Cys
            20

<210> SEQ ID NO 157
<211> LENGTH: 23
<212> TYPE: PRT
<213> ORGANISM: Oryctolagus

<400> SEQUENCE: 157

Glu Leu Asp Leu Thr Gln Thr Pro Ala Ser Val Glu Val Ala Val Gly
1               5                   10                  15

Gly Thr Val Thr Ile Asn Cys
            20
```

<210> SEQ ID NO 158
<211> LENGTH: 23
<212> TYPE: PRT
<213> ORGANISM: Oryctolagus

<400> SEQUENCE: 158

Glu Leu Asp Met Thr Gln Thr Pro Ser Ser Val Ser Ala Ala Val Gly
1               5                   10                  15

Gly Thr Val Thr Ile Asn Cys
            20

<210> SEQ ID NO 159
<211> LENGTH: 23
<212> TYPE: PRT
<213> ORGANISM: Oryctolagus

<400> SEQUENCE: 159

Glu Leu Val Met Thr Gln Thr Pro Ala Ser Val Ser Ala Ala Val Gly
1               5                   10                  15

Gly Thr Val Thr Ile Asn Cys
            20

<210> SEQ ID NO 160
<211> LENGTH: 23
<212> TYPE: PRT
<213> ORGANISM: Oryctolagus

<400> SEQUENCE: 160

Glu Leu Val Met Thr Gln Thr Pro Ala Ser Val Glu Ala Ala Val Gly
1               5                   10                  15

Asp Ser Val Thr Ile Asn Cys
            20

<210> SEQ ID NO 161
<211> LENGTH: 23
<212> TYPE: PRT
<213> ORGANISM: Oryctolagus

<400> SEQUENCE: 161

Glu Leu Val Leu Thr Gln Thr Pro Ala Ser Val Ser Glu Pro Val Gly
1               5                   10                  15

Gly Thr Val Thr Ile Lys Cys
            20

<210> SEQ ID NO 162
<211> LENGTH: 23
<212> TYPE: PRT
<213> ORGANISM: Oryctolagus

<400> SEQUENCE: 162

Glu Leu Val Leu Thr Gln Thr Pro Ser Pro Val Ser Ala Ala Val Gly
1               5                   10                  15

Gly Thr Val Thr Ile Ser Cys
            20

<210> SEQ ID NO 163
<211> LENGTH: 23
<212> TYPE: PRT
<213> ORGANISM: Oryctolagus

```
<400> SEQUENCE: 163

Glu Leu Val Met Thr Gln Thr Glu Ser Pro Val Ser Ala Pro Val Gly
1               5                   10                  15

Gly Thr Val Thr Ile Lys Cys
            20

<210> SEQ ID NO 164
<211> LENGTH: 23
<212> TYPE: PRT
<213> ORGANISM: Oryctolagus

<400> SEQUENCE: 164

Glu Leu Val Leu Thr Gln Thr Pro Ser Ser Lys Ser Val Pro Val Gly
1               5                   10                  15

Glu Thr Val Thr Ile Asn Cys
            20

<210> SEQ ID NO 165
<211> LENGTH: 23
<212> TYPE: PRT
<213> ORGANISM: Oryctolagus

<400> SEQUENCE: 165

Glu Leu Asp Met Thr Gln Thr Pro Ser Ser Lys Ser Val Pro Val Arg
1               5                   10                  15

Gly Thr Val Ser Ile Ser Cys
            20

<210> SEQ ID NO 166
<211> LENGTH: 23
<212> TYPE: PRT
<213> ORGANISM: Oryctolagus

<400> SEQUENCE: 166

Glu Leu Val Leu Thr Gln Ser Pro Ser Ser Lys Ser Val Pro Val Gly
1               5                   10                  15

Asp Thr Val Thr Ile Asn Cys
            20

<210> SEQ ID NO 167
<211> LENGTH: 23
<212> TYPE: PRT
<213> ORGANISM: Oryctolagus

<400> SEQUENCE: 167

Glu Leu Asp Leu Thr Gln Thr Pro Pro Ser Leu Ser Ala Ser Val Gly
1               5                   10                  15

Glu Thr Val Arg Ile Arg Cys
            20

<210> SEQ ID NO 168
<211> LENGTH: 23
<212> TYPE: PRT
<213> ORGANISM: Oryctolagus

<400> SEQUENCE: 168

Glu Leu Asp Leu Thr Gln Thr Pro Ala Ser Val Glu Ala Ala Val Gly
1               5                   10                  15

Gly Thr Val Thr Ile Lys Cys
            20
```

<210> SEQ ID NO 169
<211> LENGTH: 23
<212> TYPE: PRT
<213> ORGANISM: Oryctolagus

<400> SEQUENCE: 169

Glu Leu Val Met Thr Gln Thr Pro Ser Pro Val Ser Ala Ala Val Gly
1               5                   10                  15

Gly Thr Val Thr Ile Ser Cys
            20

<210> SEQ ID NO 170
<211> LENGTH: 23
<212> TYPE: PRT
<213> ORGANISM: Oryctolagus

<400> SEQUENCE: 170

Glu Leu Val Leu Thr Gln Thr Pro Ser Ser Lys Ser Val Pro Val Gly
1               5                   10                  15

Asp Thr Val Ile Ile Asn Cys
            20

<210> SEQ ID NO 171
<211> LENGTH: 22
<212> TYPE: PRT
<213> ORGANISM: Oryctolagus

<400> SEQUENCE: 171

Glu Leu Val Leu Thr Gln Ser Pro Ser Val Ser Gly Ala Val Gly Gly
1               5                   10                  15

Thr Val Ile Ile Asn Cys
            20

<210> SEQ ID NO 172
<211> LENGTH: 23
<212> TYPE: PRT
<213> ORGANISM: Oryctolagus

<400> SEQUENCE: 172

Glu Leu Val Leu Thr Gln Thr Pro Ser Ser Val Glu Ala Ala Val Gly
1               5                   10                  15

Gly Thr Val Thr Ile Lys Cys
            20

<210> SEQ ID NO 173
<211> LENGTH: 23
<212> TYPE: PRT
<213> ORGANISM: Oryctolagus

<400> SEQUENCE: 173

Glu Leu Val Leu Thr Gln Thr Pro Ala Ser Val Glu Ala Ala Val Gly
1               5                   10                  15

Gly Thr Val Thr Ile Lys Cys
            20

<210> SEQ ID NO 174
<211> LENGTH: 15
<212> TYPE: PRT
<213> ORGANISM: Oryctolagus

<400> SEQUENCE: 174

Trp Tyr Gln Gln Lys Pro Glu Lys Pro Pro Thr Leu Leu Ile Ser
1               5                   10                  15

<210> SEQ ID NO 175
<211> LENGTH: 15
<212> TYPE: PRT
<213> ORGANISM: Oryctolagus

<400> SEQUENCE: 175

Trp Tyr Gln Gln Lys Pro Gly Gln Pro Pro Lys Leu Leu Ile Tyr
1               5                   10                  15

<210> SEQ ID NO 176
<211> LENGTH: 15
<212> TYPE: PRT
<213> ORGANISM: Oryctolagus

<400> SEQUENCE: 176

Trp Tyr Gln Gln Lys Pro Gly Gln Pro Pro Lys Arg Leu Ile Tyr
1               5                   10                  15

<210> SEQ ID NO 177
<211> LENGTH: 15
<212> TYPE: PRT
<213> ORGANISM: Oryctolagus

<400> SEQUENCE: 177

Trp Tyr Gln Leu Lys Pro Gly Gln Pro Pro Lys Leu Leu Ile Tyr
1               5                   10                  15

<210> SEQ ID NO 178
<211> LENGTH: 15
<212> TYPE: PRT
<213> ORGANISM: Oryctolagus

<400> SEQUENCE: 178

Trp Tyr Gln Gln Lys Pro Gly Gln Pro Pro Lys Pro Leu Ile Tyr
1               5                   10                  15

<210> SEQ ID NO 179
<211> LENGTH: 15
<212> TYPE: PRT
<213> ORGANISM: Oryctolagus

<400> SEQUENCE: 179

Trp Phe Gln Gln Lys Pro Gly Gln Pro Pro Lys Leu Leu Ile Tyr
1               5                   10                  15

<210> SEQ ID NO 180
<211> LENGTH: 15
<212> TYPE: PRT
<213> ORGANISM: Oryctolagus

<400> SEQUENCE: 180

Trp Tyr Gln Gln Lys Pro Gly Lys Pro Pro Thr Leu Leu Ile Ser
1               5                   10                  15

<210> SEQ ID NO 181
<211> LENGTH: 15
<212> TYPE: PRT
<213> ORGANISM: Oryctolagus

<400> SEQUENCE: 181

Trp Tyr Gln Gln Lys Pro Gly Gln Arg Pro Lys Leu Leu Ile Tyr
1               5                   10                  15

<210> SEQ ID NO 182
<211> LENGTH: 15

<212> TYPE: PRT
<213> ORGANISM: Oryctolagus

<400> SEQUENCE: 182

Trp Tyr Gln Gln Lys Ala Gly Lys Pro Pro Thr Leu Leu Ile Tyr
1               5                   10                  15

<210> SEQ ID NO 183
<211> LENGTH: 32
<212> TYPE: PRT
<213> ORGANISM: Oryctolagus

<400> SEQUENCE: 183

Gly Val Pro Pro Arg Phe Ser Gly Ser Gly Ser Gly Thr Asp Tyr Thr
1               5                   10                  15

Leu Thr Ile Gly Gly Val Gln Ala Glu Asp Val Ala Thr Tyr Tyr Cys
            20                  25                  30

<210> SEQ ID NO 184
<211> LENGTH: 32
<212> TYPE: PRT
<213> ORGANISM: Oryctolagus

<400> SEQUENCE: 184

Gly Val Ser Ser Arg Phe Lys Gly Ser Gly Ser Gly Thr Glu Phe Thr
1               5                   10                  15

Leu Thr Ile Ser Gly Val Gln Cys Asp Asp Ala Ala Thr Tyr Tyr Cys
            20                  25                  30

<210> SEQ ID NO 185
<211> LENGTH: 32
<212> TYPE: PRT
<213> ORGANISM: Oryctolagus

<400> SEQUENCE: 185

Gly Val Ser Ser Arg Phe Lys Gly Ser Arg Ser Gly Thr Glu Tyr Thr
1               5                   10                  15

Leu Thr Ile Ser Asp Leu Glu Cys Ala Asp Ala Ala Thr Tyr Tyr Cys
            20                  25                  30

<210> SEQ ID NO 186
<211> LENGTH: 32
<212> TYPE: PRT
<213> ORGANISM: Oryctolagus

<400> SEQUENCE: 186

Gly Val Ser Ser Arg Phe Lys Gly Ser Gly Ser Gly Thr Glu Phe Thr
1               5                   10                  15

Leu Thr Ile Ser Asp Val Gln Cys Asp Asp Ala Ala Thr Tyr Tyr Cys
            20                  25                  30

<210> SEQ ID NO 187
<211> LENGTH: 32
<212> TYPE: PRT
<213> ORGANISM: Oryctolagus

<400> SEQUENCE: 187

Gly Val Pro Ser Arg Phe Lys Gly Ser Gly Ser Gly Thr Glu Phe Thr
1               5                   10                  15

Leu Thr Ile Ser Asp Leu Glu Cys Ala Asp Ala Ala Thr Tyr Tyr Cys
            20                  25                  30

```
<210> SEQ ID NO 188
<211> LENGTH: 32
<212> TYPE: PRT
<213> ORGANISM: Oryctolagus

<400> SEQUENCE: 188

Gly Val Pro Ser Arg Phe Arg Gly Ser Gly Ser Gly Thr Glu Phe Thr
1               5                   10                  15

Leu Thr Ile Ser Gly Met Lys Ala Glu Asp Ala Ala Thr Tyr Tyr Cys
            20                  25                  30

<210> SEQ ID NO 189
<211> LENGTH: 32
<212> TYPE: PRT
<213> ORGANISM: Oryctolagus

<400> SEQUENCE: 189

Gly Val Ser Ser Arg Phe Lys Gly Ser Gly Ser Gly Thr Gln Phe Thr
1               5                   10                  15

Leu Thr Ile Ser Asp Leu Glu Cys Asp Asp Ala Ala Thr Tyr Tyr Cys
            20                  25                  30

<210> SEQ ID NO 190
<211> LENGTH: 32
<212> TYPE: PRT
<213> ORGANISM: Oryctolagus

<400> SEQUENCE: 190

Gly Val Pro Ser Arg Phe Lys Gly Ser Gly Ser Gly Thr Glu Tyr Thr
1               5                   10                  15

Leu Thr Ile Ser Gly Val Glu Cys Asp Asp Ala Ala Thr Tyr Tyr Cys
            20                  25                  30

<210> SEQ ID NO 191
<211> LENGTH: 32
<212> TYPE: PRT
<213> ORGANISM: Oryctolagus

<400> SEQUENCE: 191

Gly Val Pro Pro Arg Phe Ser Gly Ser Gly Ala Gly Thr Gln Phe Thr
1               5                   10                  15

Leu Thr Ile Ser Asp Leu Glu Cys Asp Asp Ala Ala Thr Tyr Tyr Cys
            20                  25                  30

<210> SEQ ID NO 192
<211> LENGTH: 32
<212> TYPE: PRT
<213> ORGANISM: Oryctolagus

<400> SEQUENCE: 192

Gly Val Pro Ser Arg Phe Lys Gly Ser Gly Ser Gly Ala Gln Phe Thr
1               5                   10                  15

Leu Thr Ile Ser Asp Leu Glu Cys Asp Asp Ala Ala Thr Tyr Tyr Cys
            20                  25                  30

<210> SEQ ID NO 193
<211> LENGTH: 32
<212> TYPE: PRT
<213> ORGANISM: Oryctolagus

<400> SEQUENCE: 193

Gly Val Pro Ser Arg Phe Lys Gly Ser Gly Ser Gly Thr Gln Phe Thr
1               5                   10                  15
```

Leu Thr Ile Ser Asp Leu Glu Cys Asp Asp Ala Ala Thr Tyr Tyr Cys
            20                  25                  30

<210> SEQ ID NO 194
<211> LENGTH: 32
<212> TYPE: PRT
<213> ORGANISM: Oryctolagus

<400> SEQUENCE: 194

Gly Val Pro Ser Arg Phe Lys Gly Ser Gly Ser Gly Thr Glu Phe Thr
1               5                   10                  15

Leu Thr Ile Ser Gly Val Gln Cys Asp Asp Ala Ala Thr Tyr Phe Cys
            20                  25                  30

<210> SEQ ID NO 195
<211> LENGTH: 32
<212> TYPE: PRT
<213> ORGANISM: Oryctolagus

<400> SEQUENCE: 195

Gly Val Pro Ser Arg Phe Lys Gly Ser Gly Ser Gly Thr Gln Phe Thr
1               5                   10                  15

Leu Thr Ile Ser Asp Val Val Cys Asp Asp Ala Ala Thr Tyr Tyr Cys
            20                  25                  30

<210> SEQ ID NO 196
<211> LENGTH: 32
<212> TYPE: PRT
<213> ORGANISM: Oryctolagus

<400> SEQUENCE: 196

Gly Val Pro Ser Arg Phe Lys Gly Ser Gly Ser Gly Thr Asp Phe Thr
1               5                   10                  15

Leu Thr Ile Ser Ser Val Glu Cys Asp Asp Ala Ala Thr Tyr Tyr Cys
            20                  25                  30

<210> SEQ ID NO 197
<211> LENGTH: 32
<212> TYPE: PRT
<213> ORGANISM: Oryctolagus

<400> SEQUENCE: 197

Gly Val Pro Ser Arg Phe Ser Gly Ser Gly Ser Gly Thr Gln Phe Thr
1               5                   10                  15

Leu Thr Ile Ser Asp Leu Glu Cys Asp Asp Ala Ala Thr Tyr Tyr Cys
            20                  25                  30

<210> SEQ ID NO 198
<211> LENGTH: 32
<212> TYPE: PRT
<213> ORGANISM: Oryctolagus

<400> SEQUENCE: 198

Gly Val Pro Pro Arg Phe Ser Gly Ser Gly Ser Gly Ala Asp Tyr Thr
1               5                   10                  15

Leu Thr Ile Gly Gly Val Gln Ala Glu Asp Ala Ala Thr Tyr Tyr Cys
            20                  25                  30

<210> SEQ ID NO 199
<211> LENGTH: 32
<212> TYPE: PRT
<213> ORGANISM: Oryctolagus

```
<400> SEQUENCE: 199

Gly Val Pro Ser Arg Phe Lys Gly Ser Gly Ser Gly Thr Gln Phe Thr
1               5                   10                  15

Leu Thr Ile Ser Asp Val Gln Cys Asp Asp Ala Ala Thr Tyr Tyr Cys
            20                  25                  30

<210> SEQ ID NO 200
<211> LENGTH: 32
<212> TYPE: PRT
<213> ORGANISM: Oryctolagus

<400> SEQUENCE: 200

Gly Val Ser Ser Arg Phe Lys Gly Ser Gly Ser Gly Thr Gln Phe Thr
1               5                   10                  15

Leu Thr Ile Asn Asp Leu Glu Cys Asp Asp Ala Ala Thr Tyr Tyr Cys
            20                  25                  30

<210> SEQ ID NO 201
<211> LENGTH: 32
<212> TYPE: PRT
<213> ORGANISM: Oryctolagus

<400> SEQUENCE: 201

Gly Val Pro Ser Arg Phe Lys Gly Ser Gly Ser Gly Thr Gln Phe Thr
1               5                   10                  15

Leu Thr Ile Ser Asp Val Val Cys Asp Asp Ala Ala Thr Tyr Gly Cys
            20                  25                  30

<210> SEQ ID NO 202
<211> LENGTH: 32
<212> TYPE: PRT
<213> ORGANISM: Oryctolagus

<400> SEQUENCE: 202

Gly Val Pro Ser Arg Phe Lys Gly Ser Gly Ser Gly Thr Gln Phe Thr
1               5                   10                  15

Leu Thr Ile Ser Gly Val Gln Cys Asp Asp Ala Ala Thr Tyr Tyr Cys
            20                  25                  30

<210> SEQ ID NO 203
<211> LENGTH: 32
<212> TYPE: PRT
<213> ORGANISM: Oryctolagus

<400> SEQUENCE: 203

Gly Val Pro Ser Arg Phe Ser Gly Ser Gly Ser Gly Thr Glu Phe Thr
1               5                   10                  15

Leu Thr Ile Asn Asp Leu Asp Cys Asp Asp Ala Ala Thr Tyr Tyr Cys
            20                  25                  30

<210> SEQ ID NO 204
<211> LENGTH: 32
<212> TYPE: PRT
<213> ORGANISM: Oryctolagus

<400> SEQUENCE: 204

Gly Val Pro Ser Arg Phe Lys Gly Ser Gly Ser Gly Thr Gln Phe Thr
1               5                   10                  15

Leu Thr Ile Ser Asp Leu Glu Cys Ala Asp Ala Ala Thr Tyr Tyr Cys
            20                  25                  30
```

```
<210> SEQ ID NO 205
<211> LENGTH: 32
<212> TYPE: PRT
<213> ORGANISM: Oryctolagus

<400> SEQUENCE: 205

Gly Val Ser Ser Arg Phe Lys Gly Ser Gly Ser Gly Thr Gln Phe Thr
1               5                   10                  15

Leu Thr Ile Ser Gly Val Gln Cys Ala Asp Ala Ala Thr Tyr Tyr Cys
            20                  25                  30

<210> SEQ ID NO 206
<211> LENGTH: 10
<212> TYPE: PRT
<213> ORGANISM: Oryctolagus

<400> SEQUENCE: 206

Phe Gly Ala Gly Thr Asn Val Glu Ile Lys
1               5                   10

<210> SEQ ID NO 207
<211> LENGTH: 10
<212> TYPE: PRT
<213> ORGANISM: Oryctolagus

<400> SEQUENCE: 207

Phe Gly Gly Gly Thr Glu Val Val Val Lys
1               5                   10

<210> SEQ ID NO 208
<211> LENGTH: 10
<212> TYPE: PRT
<213> ORGANISM: Oryctolagus

<400> SEQUENCE: 208

Phe Gly Gly Gly Thr Glu Leu Glu Ile Leu
1               5                   10

<210> SEQ ID NO 209
<211> LENGTH: 11
<212> TYPE: PRT
<213> ORGANISM: Oryctolagus

<400> SEQUENCE: 209

Phe Gly Gly Gly Thr Gln Leu Thr Val Thr Gly
1               5                   10

<210> SEQ ID NO 210
<211> LENGTH: 12
<212> TYPE: PRT
<213> ORGANISM: Oryctolagus

<400> SEQUENCE: 210

Phe Ala Phe Gly Gly Gly Thr Glu Leu Glu Ile Leu
1               5                   10
```